United States Patent
Gerlach et al.

(10) Patent No.: US 11,795,147 B2
(45) Date of Patent: Oct. 24, 2023

(54) MODULATORS OF COMPLEX I

(71) Applicant: Boehringer Ingelheim International GmbH, Ingelheim am Rhein (DE)

(72) Inventors: Kai Gerlach, Mittelbiberach (DE); Christian Eickmeier, Mittelbiberach (DE); Jan Magnus Kriegl, Ulm (DE); Lothar Kussmaul, Schemmerhofen (DE); Klaus Rudolf, Warthausen (DE); Bernhard Schmid, Ingoldingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/002,937

(22) Filed: Aug. 26, 2020

(65) Prior Publication Data
US 2021/0061761 A1 Mar. 4, 2021

(30) Foreign Application Priority Data

Aug. 26, 2019 (EP) .................. 19193570

(51) Int. Cl.
*C07D 207/38* (2006.01)
*C07D 403/04* (2006.01)
*C07D 471/08* (2006.01)
*C07D 491/044* (2006.01)
*C07D 498/10* (2006.01)

(52) U.S. Cl.
CPC ......... *C07D 207/38* (2013.01); *C07D 403/04* (2013.01); *C07D 471/08* (2013.01); *C07D 491/044* (2013.01); *C07D 498/10* (2013.01)

(58) Field of Classification Search
CPC .. C07D 213/80; C07D 207/38; C07D 403/04; C07D 471/08; C07D 491/044; C07D 498/10; A61K 31/5377; A61K 31/366; A61K 31/40; A61K 31/535
See application file for complete search history.

(56) References Cited

U.S. PATENT DOCUMENTS 7,476,663 B2  1/2009  Pfau et al.
8,207,179 B2  6/2012  Engelhardt et al.

FOREIGN PATENT DOCUMENTS

| EP | 1790641 A1 | 5/2007 |
|---|---|---|
| JP | 2018127429 A | 8/2018 |
| WO | 2004060376 A1 | 7/2004 |
| WO | 2005111029 A1 | 11/2005 |
| WO | 2006072350 A1 | 7/2006 |
| WO | 2008076356 A1 | 6/2008 |
| WO | 2008152014 A2 | 12/2008 |
| WO | 2010068520 A2 | 6/2010 |
| WO | 2011052950 A2 | 5/2011 |
| WO | 2017098733 A1 | 6/2017 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003], Retrieved from the internet, URL;http;//www.cnn/com/2003/HEALTH/conditions/09/24/alzheimers.drug.ap/index.html>.*
Tan, Shirlee et al. "The Regulation of Reactive Oxygen Species Production during Programmed Cell Death" (1998) The Journal of Cell Biology, vol. 141, No. 6, 1423-1432.
International Search Report and Written Opinion for corresponding application, PCT/EP2020/0739988, dated Oct. 23, 2020.

* cited by examiner

*Primary Examiner* — Rebecca L Anderson
(74) *Attorney, Agent, or Firm* — Philip I. Datlow

(57) ABSTRACT

The present invention describes compounds modulating the function of mitochondrial complex I (NADH-quinone oxidoreductase) having formula (I)

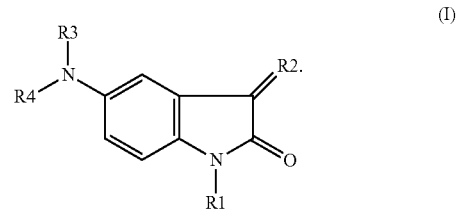

7 Claims, No Drawings

MODULATORS OF COMPLEX I

The present invention relates to compounds having formula (I)

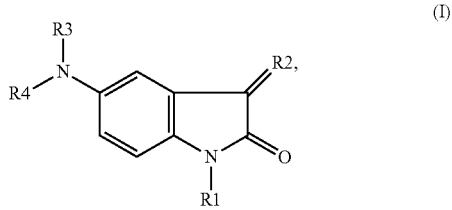

their pharmaceutical compositions, and their use in therapy. Unexpectedly, said compounds modulate the function of the mitochondrial complex I (NADH-quinone oxidoreductase) allowing the treatment or prevention of conditions having an association with Complex I NADH-quinone oxidoreductase mediated oxidative stress.

Oxidative stress reflects the imbalance between the generation and detoxification of Reactive Oxygen Species (ROS), which can cause toxic effects through the increased concentration of ROS, through disruption in cellular signaling and/or through damaging/oxidation of proteins, DNA or lipids. Oxidative stress is suspected to be important in many diseases.

A variety of enzymes generate reactive oxygen species (ROS) in cells. One major source of ROS is oxidative phosphorylation via Complex I. The enzyme is a protein complex, encoded by 39 nuclear and 7 mitochondrial genes which is expressed ubiquitously and transfers electrons from NADH to Ubiquinone, coupled to translocation of protons necessary for ATP synthesis.

Since NADH-oxidation is much faster than reduction of Ubiquinone, the enzyme is reduced under physiological conditions and electron leakage (i.e. production of the negatively charged superoxide $O_2^{\bullet-}$ radical) occurs at the NADH-binding site. In consequence a low efficiency of UQ reduction is coupled to increased $O_2^{\bullet-}$ formation, which can be observed in several diseases such as Leigh syndrome, LHON disease, AMD or Parkinson's disease among others.

The cytotoxic $O_2^{\bullet-}$ generated by Complex I is detoxified mainly by the mitochondrial superoxide dismutase (SOD2), generating hydrogen peroxide which is detoxified by a variety of enzymes, such as Catalase, Glutathionperoxidase(s), Thioreredoxin(s) etc. Given the central importance of Complex I in oxidative phosphorylation and redox homeostasis, identification of agents that can inhibit ROS formation are of great interest as possible therapeutic agents.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, (O)$_2$S, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-C1-3-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk (*) may be used in sub-formulas to indicate the bond which is connected to the core molecule as defined.

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

The term "alkyl", either apart or in combination with another radical, denotes an acyclic, saturated, branched or linear hydrocarbon radical with 1 to 6 C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH$ (CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "cycloalkyl", either apart or in combination with another radical denotes a cyclic, saturated, unbranched hydrocarbon radical with 3 to 8 C atoms, preferably 3 to 5 C atoms. For example the term $C_{3-8}$-cycloalkyl includes cyclopropyl, cyclobutyl, cyclopentyl, cyclohexyl, cycloheptyl, and cyclooctyl and the term $C_{3-5}$-cycloalkyl cyclopropyl, cyclobutyl and cyclopentyl.

By the term "halo" added to an "alkyl" or "cycloalkyl" group (saturated or unsaturated) is such an alkyl or cycloalkyl group wherein one or more hydrogen atoms are replaced by a halogen atom selected from among fluorine, chlorine or bromine, preferably fluorine and chlorine, particularly preferred is fluorine. Examples include: H₂FC—, HF₂C—, F₃C—.

The term "aryl" as used herein, either apart or in combination with another radical, denotes a carbocyclic aromatic monocyclic group containing 6 carbon atoms which is optionally further fused to a second five- or six-membered, carbocyclic group which is optionally aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring systems including aromatic ring system containing one or more heteroatoms selected from N, O or S(O)r, wherein r=0, 1 or 2, consisting of 3 to 14 ring atoms, wherein none of the heteroatoms is part of the aromatic ring. The term "heterocyclyl" is intended to include all possible isomeric forms.

Thus, the term "heterocyclyl" includes the following exemplary structures which are not depicted as radicals as each form is optionally attached through a covalent bond to any atom so long as appropriate valences are maintained:

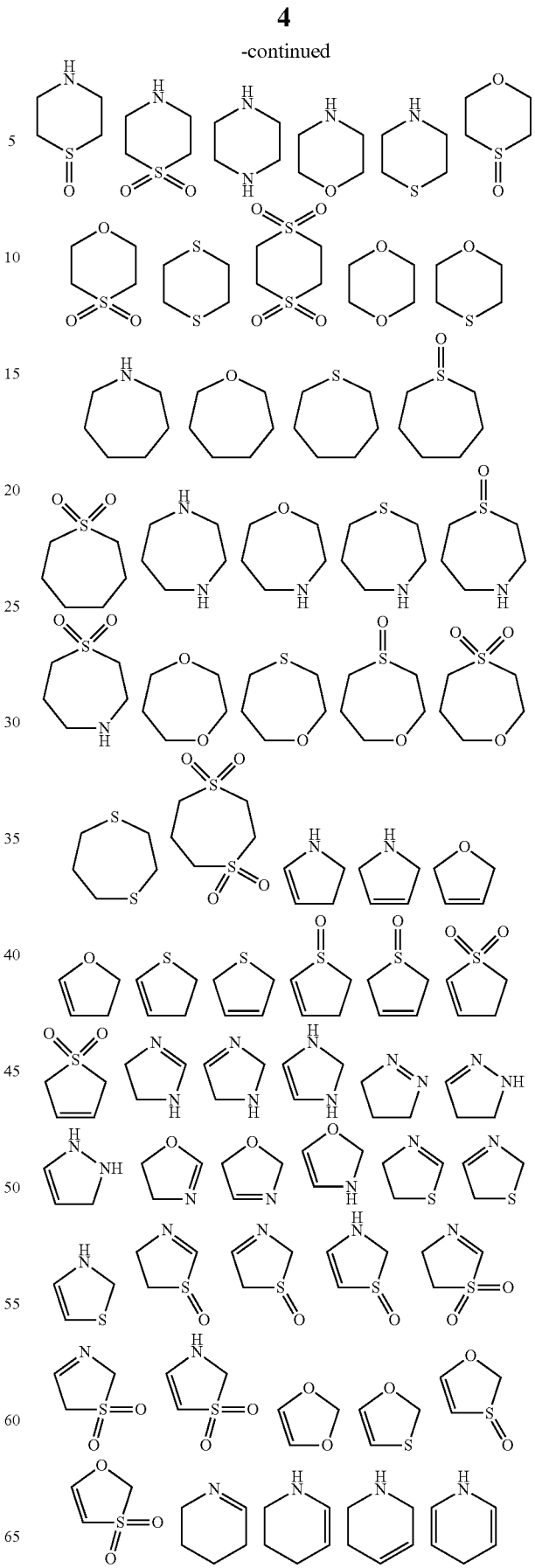

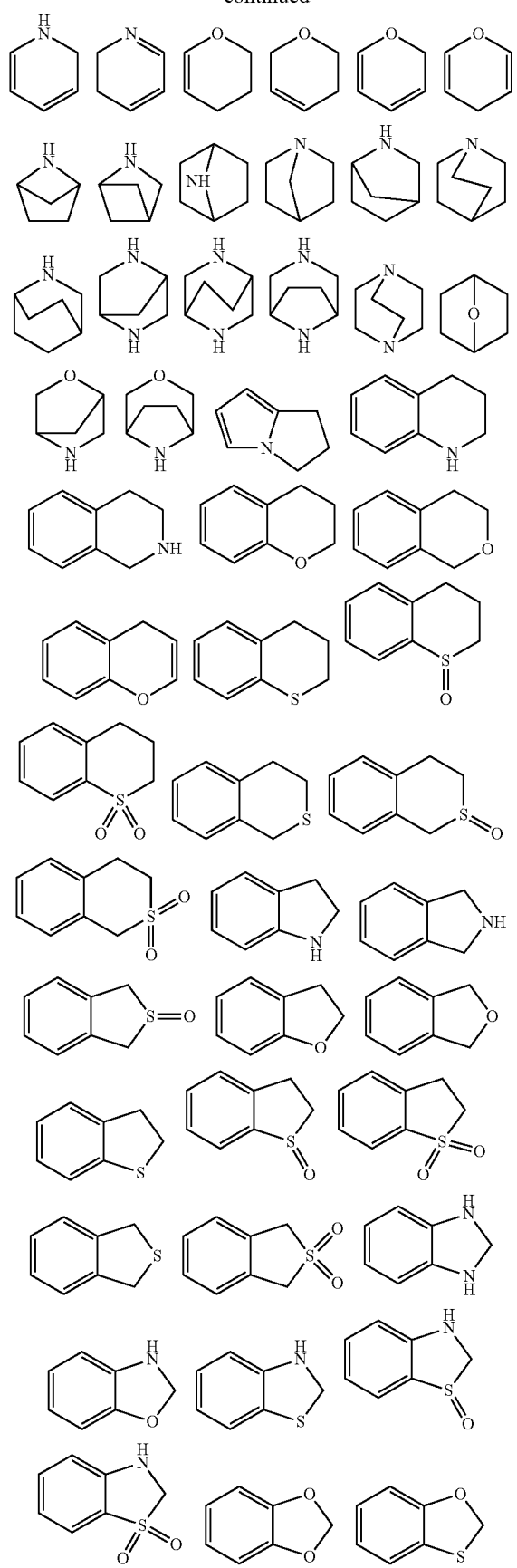
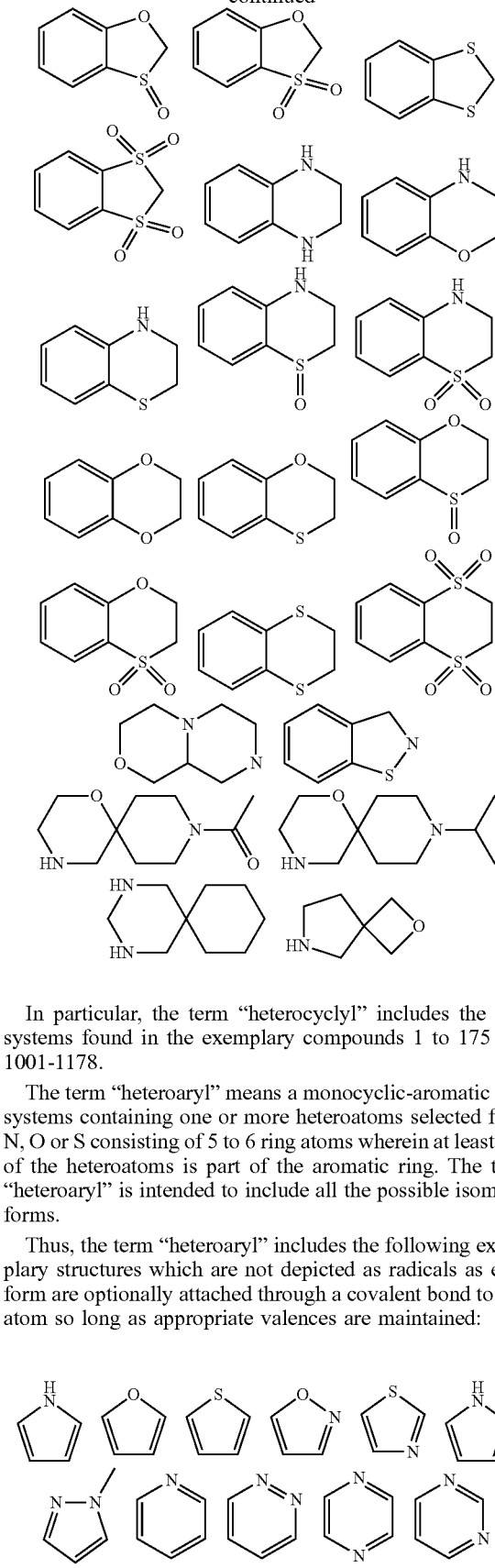

In particular, the term "heterocyclyl" includes the ring systems found in the exemplary compounds 1 to 175 and 1001-1178.

The term "heteroaryl" means a monocyclic-aromatic ring systems containing one or more heteroatoms selected from N, O or S consisting of 5 to 6 ring atoms wherein at least one of the heteroatoms is part of the aromatic ring. The term "heteroaryl" is intended to include all the possible isomeric forms.

Thus, the term "heteroaryl" includes the following exemplary structures which are not depicted as radicals as each form are optionally attached through a covalent bond to any atom so long as appropriate valences are maintained:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Many of the terms given above may be used repeatedly in the definition of a formula or group and in each case have one of the meanings given above, independently of one another.

A compound of the present invention or a salt thereof is described by formula (I)
wherein:

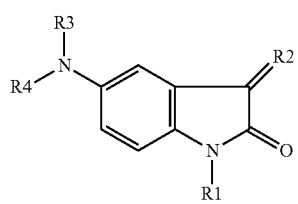

(I)

R1 is $C_{1-4}$-alkyl unsubstituted or substituted with MeO; unsubstituted tetrahydropyranyl, tetrahydrofuranyl, oxetanyl, dioxepanyl, pyrrolidinyl or piperidinyl; or pyrrolidinyl or piperidinyl with the nitrogen substituted by methyl, isopropyl, oxetanyl, ethoxcarbonyl, acetyl, or trifluoroacetyl;

R2 is a 5-, 6- or 7-membered unsubstituted or substituted ring containing 1 or 2 heteroatoms selected from 0 or N, or an unsubstituted or substituted spirocyclic heterocyclyl group containing 1 to 3 heteroatoms selected from N or O consisting of 4 to 11 ring atoms, the ring or spirocyclic heterocyclyl group being bound in formula (I) by a C═C double bond, and in which ring or spirocyclic heterocyclyl group one N-atom can be substituted by methyl, isopropyl, acetyl, benzyloxycarbonyl, phenyl, oxetanyl or tetrahydropyranyl, and in which one or more C-atoms can be substituted by -methyl or —OH;

R3 or R4 are independently from one another
hydrogen; $C_{1-6}$-alkyl, unsubstituted or substituted with one or more F, methoxy, $C_{3-8}$-cycloalkyl unsubstituted or substituted with one or more F; aryl; heteroaryl consisting of 5 to 6 ring atoms such as unsubstituted or substituted 5-pyrazolyl, or heterocyclyl consisting of 3 to 6 ring atoms, selected from the group consisting of oxetanyl, tetrahydropyranyl and pyrrolidinyl, said heterocyclyl being unsubstituted or substituted with $C_{1-6}$-alkyl, acetyl, tetrahydrofuranyl, oxetanyl; or hydroxyethylacetyl;

or R3 and R4 together with the attached N form a heterocyclyl ring selected from the group consisting of morpholinyl and pyrrolidinyl, both unsubstituted or substituted with $C_{1-6}$-alkyl, F, or hydroxyl.

Representative embodiments of Rlin formula (I) are

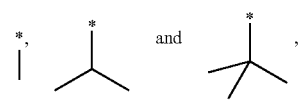

unsubstituted or substituted with MeO;

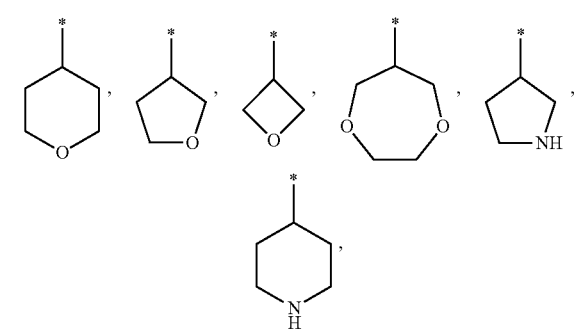

unsubstituted or the nitrogen substituted with

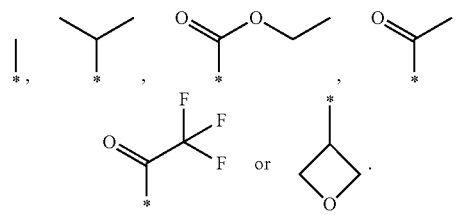

Representative embodiments of the structural element
$\dfrac{R2}{//}$ in formula (I) are
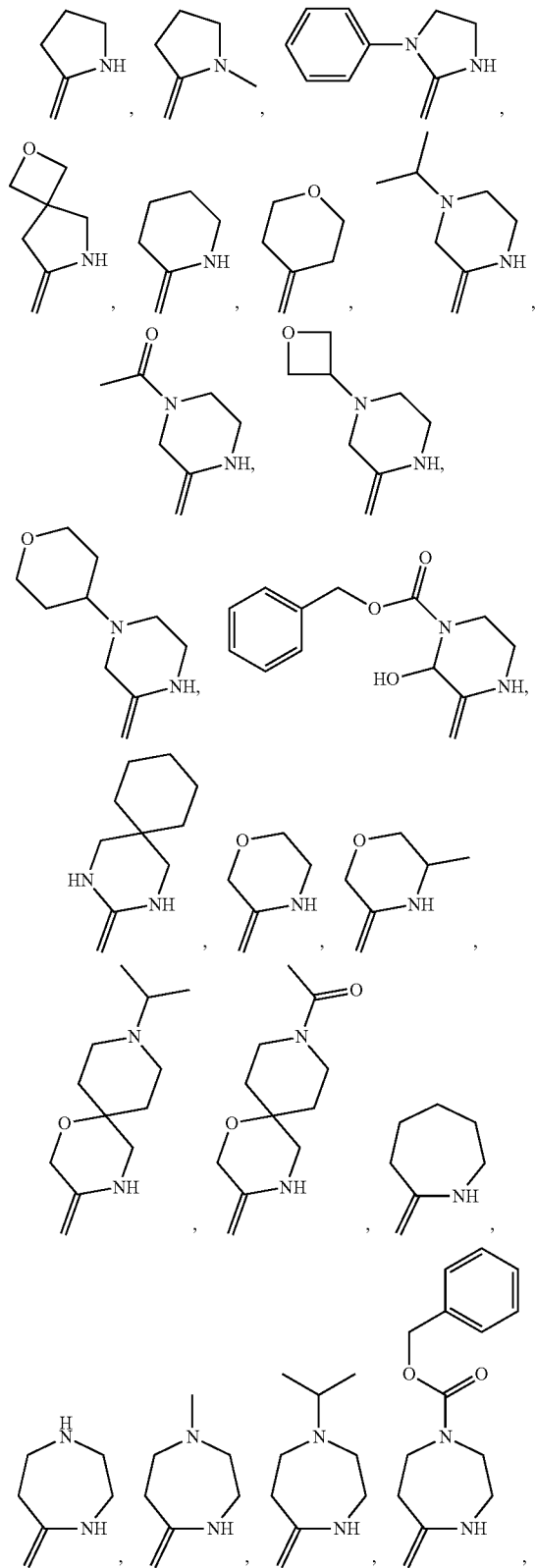
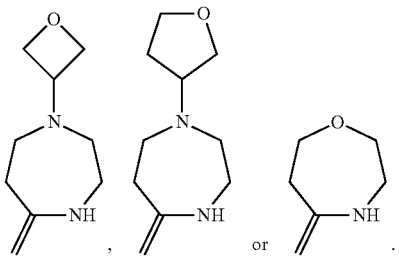
Representative embodiments of the amino group containing R3 and R4 in formula (I) are
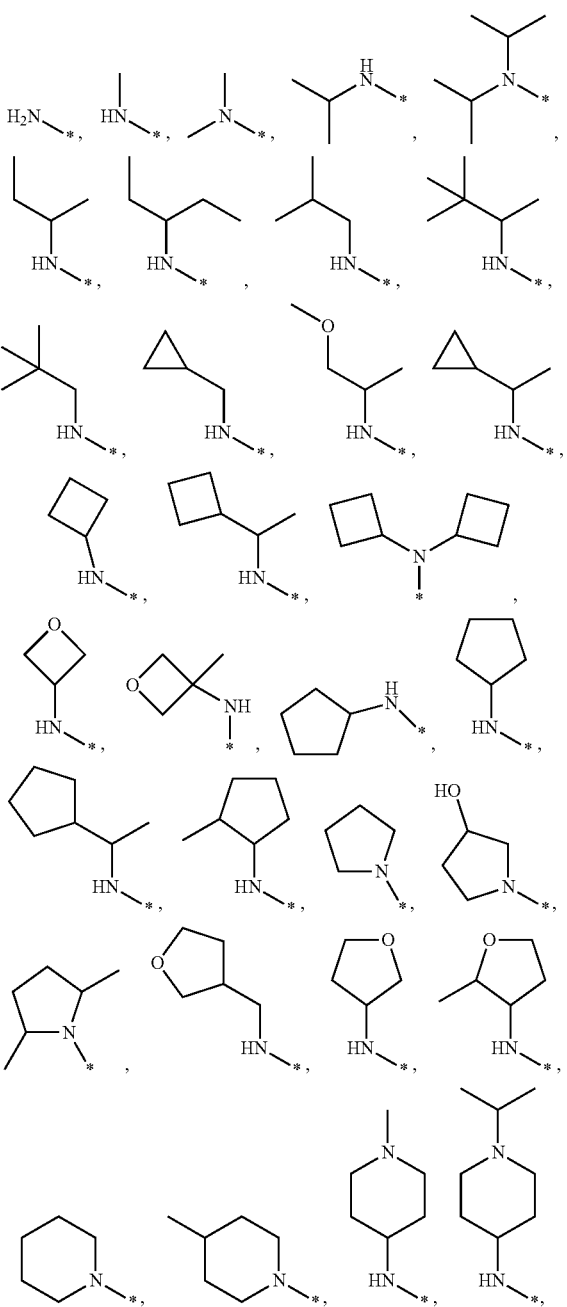

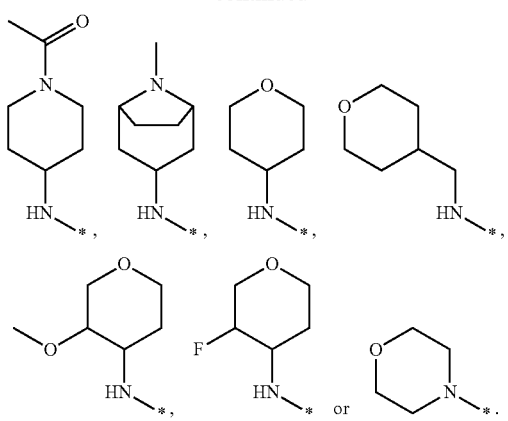

Individual embodiments of R1 in formula (I) are

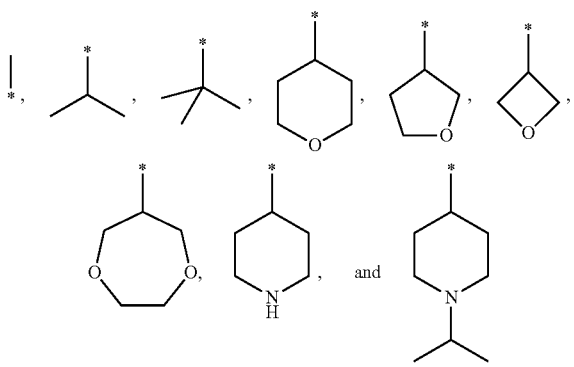

Preferred embodiments of R1 in formula (I) are tetrahydropyranyl and dioxepanyl.

An individual embodiment of the structural element
R2
∥ bound by a C═C double bond in formula (I) is a 6- or 7-membered ring containing 2 heteroatoms selected from O or N in which one or both N-atoms can be substituted by methyl, isopropyl, acetyl, benzyloxycarbonyl, phenyl, oxetanyl or tetrahydropyranyl, and in which one or more C-atoms can be substituted by -methyl or —OH Other individual embodiments of $\overset{R2}{\text{∥}}$ in formula (I) are

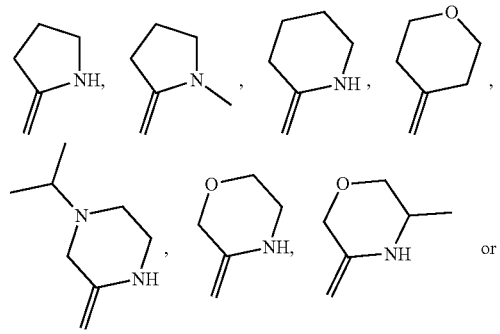

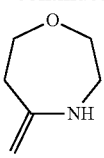

Individual embodiments of the amino group containing R3 and R4 in formula (I) encompass hydrogen as R3 while R4 is iso-propyl, cyclobutyl or cyclopentyl unsubstituted or substituted with fluorine (F).

Other individual embodiments of the amino group containing R3 and R4 in formula (I) are

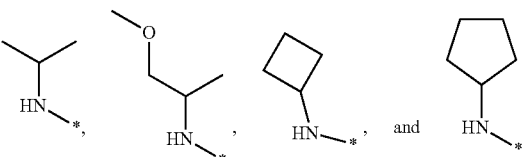

unsubstituted or substituted with one or more F.

Compounds according to the invention can be prepared with a method, wherein in a first step the compound (2-Fluoro-5-nitro-phenyl)-acetic acid (compound II)

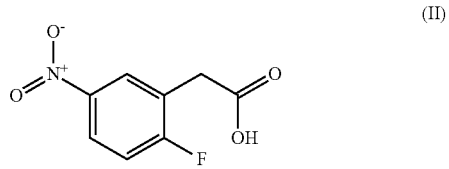 [SMILES: O=C(O)Cc1cc([N+](=O)[O-])ccc1F]

is reacted with an amine R1-NH₂ using an appropriate solvent like dimethyl acetamide, dimethyl formamide, N-methyl-pyrrolidinone, acetonitrile, DMSO, dichloromethane, toluene or the like at elevated temperature to form the compound 5-nitro-2,3-dihydro-1H-indol-2-one (compound III)

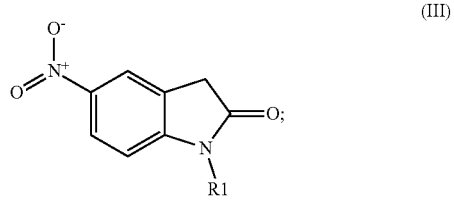

In the next step the 5-nitro-2,3-dihydro-1H-indol-2-one (compound III) is condensed at elevated temperatures in a microwave either without solvent or in a suitable solvent like piperidine with electrophiles suitable to result in a 5-nitro-3-ylidene-2,3-dihydro-1H-indol-2-one (compound IV)

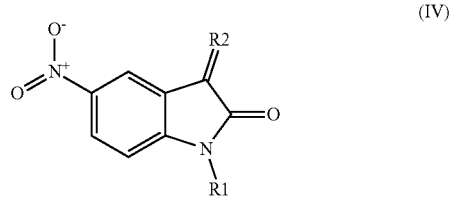

Suitable electrophiles can be iminoethers, ketones and acetals, e.g. 5-methoxy-3,6-dihydro-2H-oxazine, oxan-4-one, or 2,2-dimethoxy-1-methyl-pyrrolidine which are either commercially available or easily prepared from commercially available materials by those skilled in the art E.g., iminoethers can be prepared from suitable amides via O-methylation with trimethyloxoniumtetrafluoroborate in a suitable solvent like methylene chloride.

In the next step the compound 5-nitro-3-ylidene-2,3-dihydro-1H-indol-2-one (compound IV) is reduced to a 5-amino-3-ylidene-2,3-dihydro-1H-indol-2-one (compound V)

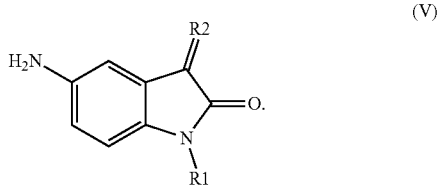

Said reductions can be achieved by catalytic hydrogenation using hydrogen gas under high pressure and a suitable catalyst like Raney-nickel in a suitable solvent like methanol.

To obtain a final compound of formula (I), a compound of formula (V) can be reacted with suitable aldehydes or ketones and a reducing agent like sodium cyanaborohydride, sodium triacetoxyborohydride or the like in a suitable solvent like methanol with the addition of an organic acid like acetic acid, pTosOH or the like.

Alternatively an amine (V) may be reacted in a substitution reaction with suitable electrophiles carrying a leaving group like Cl—, Br—. I—, methylsulfonylester, trifluorosulfonylester, tolylsulfonylester or the like in a suitable solvent such as DMF or the like and in the presence of a suitable base such as potassium carbonate.

Of the above compounds it is possible to prepare salt forms which are also subject matter of the present invention, particularly pharmaceutically acceptable salts. Medicaments prepared thereof are another subject matter of the present invention.

A compound according to the invention can be used in a medicament or pharmaceutical composition for a human patient. Such a composition can be practiced on a human body to therapeutically treat or diagnose a disease.

Similarly, a compound according to the invention can be used in a medicament or pharmaceutical composition for an animal. Such a composition can be practiced on an animal body to therapeutically treat or diagnose an animal's disease.

In particular compounds of the present invention can be used for the manufacture of a pharmaceutical composition or medicament for the treatment or prevention of a condition mentioned below in a human being.

Suitable preparations for administering the compounds of formula 1 are apparent to those with ordinary skill in the art and include for example tablets, pills, capsules, suppositories, lozenges, troches, solutions, syrups, elixirs, sachets, injectables, inhalatives and powders etc. Suitable tablets are obtained, for example, by mixing one or more compounds according to formula I with known excipients, for example inert diluents, carriers, disintegrants, adjuvants, surfactants, binders and/or lubricants.

Such a pharmaceutical composition or medicament comprises a compound or is pharmaceutically acceptable salt thereof according to the present invention in a therapeutically effective amount of 0.1 to 2000 mg.

In addition to a compound according to the present invention, such a medicament comprises a pharmaceutically acceptable carrier.

The present invention is directed to compounds useful in the treatment of a disease, disorder and condition wherein the inhibition of oxidative stress, as the lowering of ROS generated by Complex I is of therapeutic benefit. This includes but is not limited to the treatment and/or prevention of neurological or neurodegenerative or psychiatric conditions, and non-neuronal conditions such as cardiovascular diseases, ischemia-reperfusion injury, cancer and pulmonary and mitochondrial diseases.

Neurological or neurodegenerative conditions include e.g. Parkinson's disease, Alzheimer's disease (AD), Huntington's disease, amyotrophic lateral sclerosis (ALS), diseases involving retinal dysfunction like Retinopathy and age-related macular degeneration (AMD) and other brain disorders caused by trauma or other insults including aging.

Mitochondrial diseases include e.g. Leber's hereditary optic neuropathy (LHON), Leigh Syndrome, Myoclonic Epilepsy with Ragged Red Fibers (MERRF), Mitochondrial myopathy, encephalomyopathy, lactic acidosis, stroke-like symptoms (MELAS) or Diabetes mellitus and deafness (DAD)

Psychiatric conditions include depressive disorders like major depression, major depressive disorder, psychiatric depression, dysthymia, and postpartum depression, and bipolar disorders), and fear-related disorders (e.g. post-traumatic stress disorder, panic disorder, agoraphobia, social phobias, generalized anxiety disorder, panic disorder, social anxiety disorder, obsessive compulsive disorder, and separation anxiety), chronic fatigue syndrome and Autism Pain disorders include nociceptive pain, inflammatory pain, cancer pain, and neuropathic pain (e.g. cancer pain, osteoarthritic pain, rheumatoid arthritis pain, post-herpetic neuralgia, pain due to burns, and other indications). The pain can be chronic or acute.

Non-neuronal conditions include pulmonary diseases like chronic obstructive pulmonary disease (COPD), idiopathic pulmonary fibrosis (IPF) and other fibrotic diseases, nephropathy, proteinuric kidney disease, liver diseases such as hepatic dyslipidemia associated with cholestasis, non-alcoholic steatohepatitis (NASH), non-alcoholic fatty liver disease (NAFLD), itch, disorders associated with malfunction of the cardiovascular system or vascular permeability, e.g. heart failure, pulmonary arterial hypertension, acute respiratory distress syndrome (ARDS), maladaptive cardiac remodeling, disorders associated with maladaptive blood pressure control like hypertension or hypotension, infectious diseases like hepatitis and protozoal infections (including malaria, African sleeping sickness and Chagas disease), sarcopenia and other skeletal muscle diseases, disorders and other medical conditions such as diabetes, insulin resistance, metabolic syndrome and obesity.

The applicable daily dose of compounds of the present invention may vary from 0.1 to 2000 mg.

The actual pharmaceutically effective amount or therapeutic dose depends on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Suitable compositions for administering the compounds of the present invention can be produced by those with ordinary skill in the art and include for example tablets, pills, capsules, suppositories, lozenges, troches, solutions, syrups, elixirs, sachets, injectables, inhalatives, and powders. The content of a pharmaceutically active compounds may vary in the range from 0.1 to 95 wt.-%, preferably 5.0 to 90 wt.-% of the composition as a whole.

Suitable tablets can be obtained by mixing a compound of the present invention with known excipients, for example inert diluents, carriers, disintegrants, adjuvants, surfactants, binders and/or lubricants and compressing the resulting mixture to tablets.

The compounds of the present invention can be used as single active pharmaceutical ingredient or in combination with other active pharmaceutical ingredients known to be used in the art in connection with a treatment of any of the indications the treatment of which is in the focus of the present invention.

The compounds of the following table and their features are listed to illustrate the present invention, not to define its scope.

| # | Formula | CI IC$_{50}$/[μM] | HT22 IC$_{50}$/[μM] |
|---|---|---|---|
| 1 | | 0.060 | 0.282 |
| 2 | | 0.080 | 1.054 |
| 3 | | 0.077 | 0.071 |
| 4 | | 0.242 | 3.140 |

-continued

| # | Formula | CI IC$_{50}$/[μM] | HT22 IC$_{50}$/[μM] |
|---|---|---|---|
| 5 | | 0.081 | 0.220 |
| 6 | | 0.533 | 0.207 |
| 7 | | 0.350 | 0.256 |
| 8 | | 0.062 | 0.041 |

-continued

| # | Formula | CI IC$_{50}$/[μM] | HT22 IC$_{50}$/[μM] |
|---|---|---|---|
| 9 | | 0.398 | 0.038 |
| 10 | | 0.078 | 0.031 |
| 11 | | 0.031 | 0.038 |
| 12 | | 0.194 | 0.191 |

-continued

| # | Formula | CI IC$_{50}$/[μM] | HT22 IC$_{50}$/[μM] |
|---|---------|-------------------|---------------------|
| 13 | | 0.084 | 0.014 |
| 14 | | 0.101 | 0.020 |
| 15 | | 0.096 | 0.115 |
| 16 | | 0.313 | 0.693 |
| 17 | | 0.022 | 0.159 |

-continued
| # | Formula | CI IC$_{50}$/[μM] | HT22 IC$_{50}$/[μM] |
|---|---------|-------------------|---------------------|
| 18 | 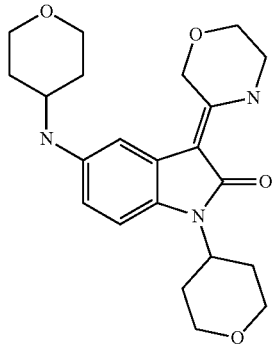 | 0.011 | 0.409 |
| 19 | 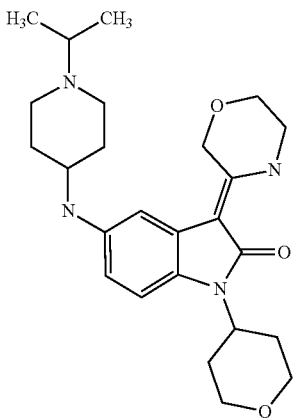 | 0.022 | 0.168 |
| 20 | 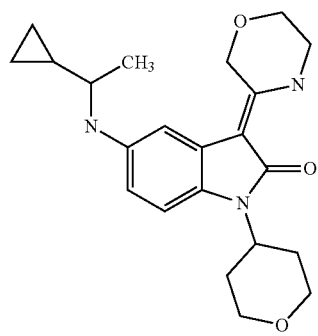 | 0.073 | 0.034 |
| 21 | 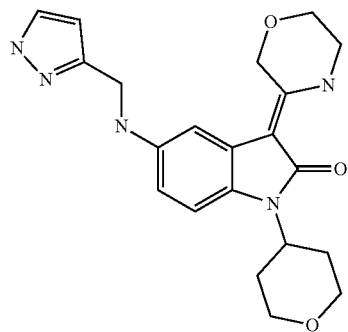 | 0.108 | 0.253 |

-continued
| # | Formula | CI IC$_{50}$/[μM] | HT22 IC$_{50}$/[μM] |
|---|---|---|---|
| 22 | 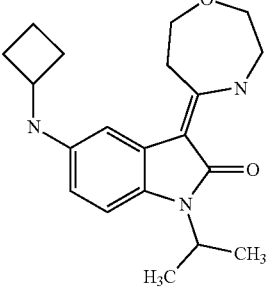 | 0.087 | 0.011 |
| 23 | 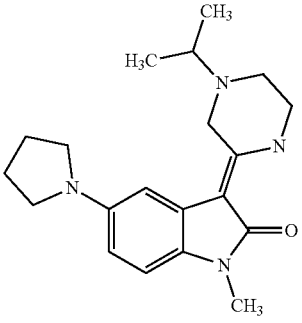 | 0.137 | 0.173 |
| 24 | 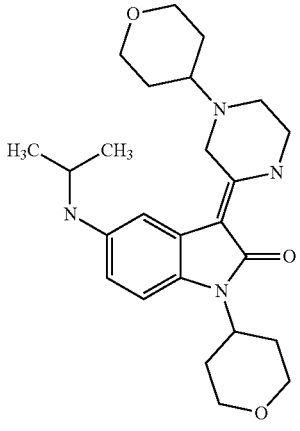 | 0.048 | 0.123 |
| 25 | 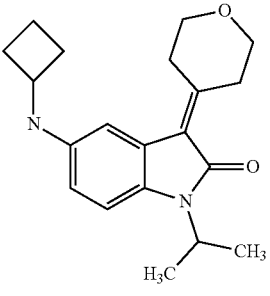 | 0.707 | 0.096 |

-continued
| # | Formula | CI IC$_{50}$/[μM] | HT22 IC$_{50}$/[μM] |
|---|---------|-------------------|---------------------|
| 26 | 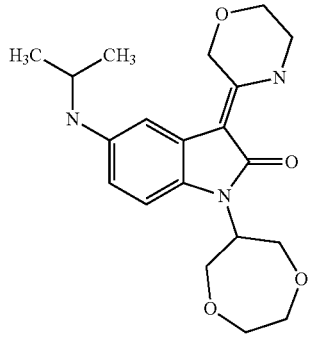 | 0.020 | 0.059 |
| 27 | 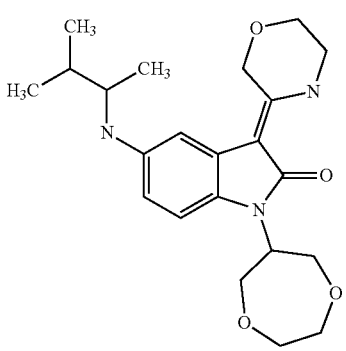 | 0.162 | 0.015 |
| 28 | 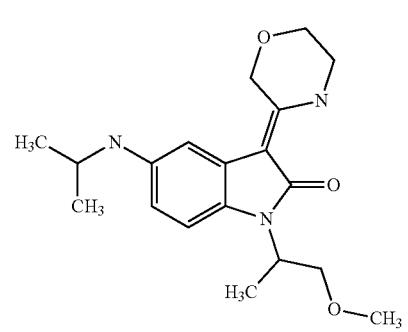 | 0.069 | 0.118 |
| 29 | 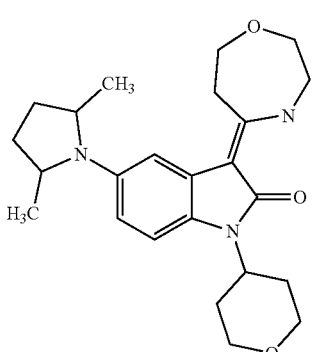 | 0.132 | 0.142 |

-continued

| # | Formula | CI IC$_{50}$/[μM] | HT22 IC$_{50}$/[μM] |
|---|---|---|---|
| 30 | | 0.195 | 0.135 |
| 31 | (Chiral) | 0.081 | 0.041 |
| 32 | | 0.031 | 0.205 |
| 33 | | 0.032 | 0.037 |

-continued

| # | Formula | CI IC$_{50}$/[μM] | HT22 IC$_{50}$/[μM] |
|---|---------|-------------------|---------------------|
| 34 | | 0.048 | 0.049 |
| 35 | | 0.083 | 2.723 |
| 36 | | 0.150 | 0.056 |
| 37 | | 0.405 | 0.003 |

-continued

| # | Formula | CI IC$_{50}$/[μM] | HT22 IC$_{50}$/[μM] |
|---|---------|-------------------|---------------------|
| 38 | | 0.051 | 0.038 |
| 39 | | 0.067 | 0.102 |
| 40 | | 0.166 | 0.013 |
| 41 | | 0.052 | 0.983 |
| 42 | | 0.042 | 0.951 |

-continued

| # | Formula | CI IC$_{50}$/[μM] | HT22 IC$_{50}$/[μM] |
|---|---------|-------------------|---------------------|
| 43 | | 0.011 | 0.124 |
| 44 | | 0.044 | 0.030 |
| 45 | | 0.259 | 0.261 |
| 46 | | 0.086 | 0.048 |

-continued

| # | Formula | CI IC$_{50}$/[μM] | HT22 IC$_{50}$/[μM] |
|---|---------|-------------------|---------------------|
| 47 | | 0.153 | 0.085 |
| 48 | | 0.122 | 0.353 |
| 49 | | 0.282 | 1.254 |
| 50 | | 0.195 | 0.013 |
| 51 | | 0.135 | 0.033 |

-continued
| # | Formula | CI IC$_{50}$/[μM] | HT22 IC$_{50}$/[μM] |
|---|---|---|---|
| 52 | 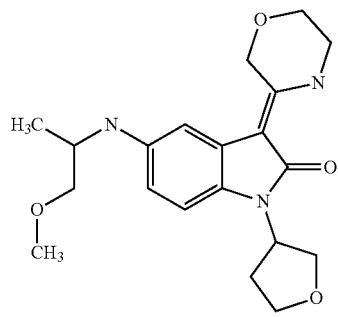 | 0.061 | 0.198 |
| 53 | 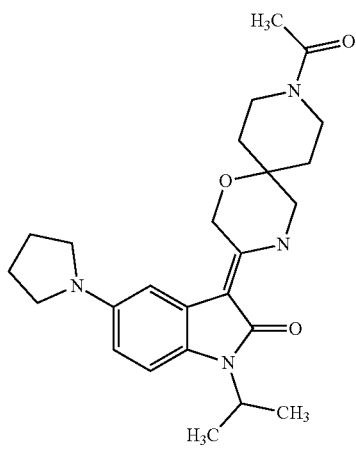 | 0.233 | 0.055 |
| 54 | 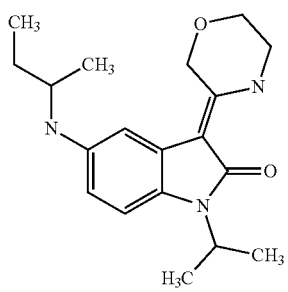 | 0.203 | 0.024 |
| 55 | 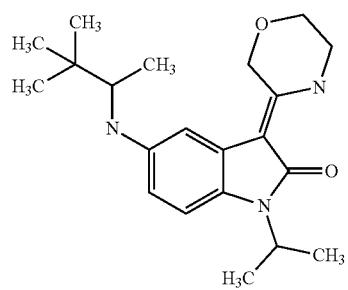 | 0.307 | 0.038 |

-continued
| # | Formula | CI IC$_{50}$/[µM] | HT22 IC$_{50}$/[µM] |
|---|---|---|---|
| 56 | 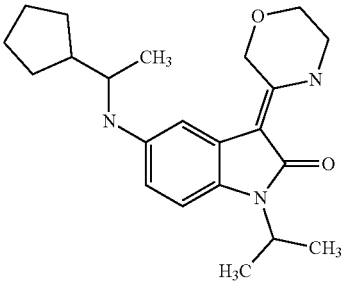 | 0.159 | 0.002 |
| 57 | 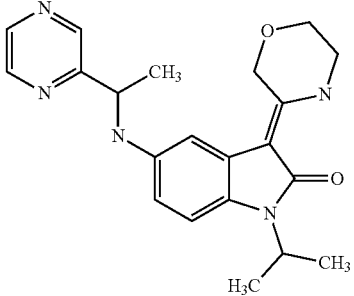 | 0.073 | 0.199 |
| 58 | 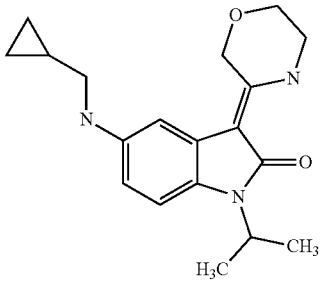 | 0.100 | 0.019 |
| 59 | 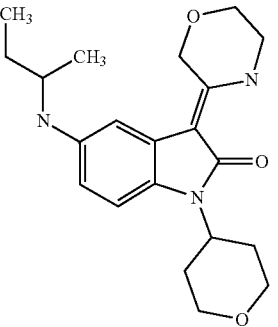 | 0.122 | 0.022 |
| 60 | 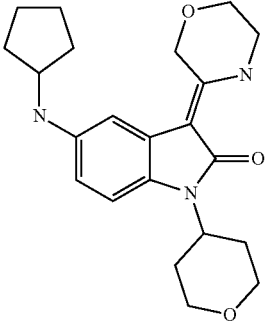 | 0.245 | 0.01 |

-continued

| # | Formula | CI IC$_{50}$/[μM] | HT22 IC$_{50}$/[μM] |
|---|---------|-------------------|---------------------|
| 61 | | 0.343 | 0.012 |
| 62 | | 0.081 | 0.162 |
| 63 | | 0.022 | 0.134 |
| 64 | | 0.286 | 0.065 |
| 65 | | 0.194 | 0.018 |

-continued
| # | Formula | CI IC$_{50}$/[μM] | HT22 IC$_{50}$/[μM] |
|---|---------|-------------------|---------------------|
| 66 | 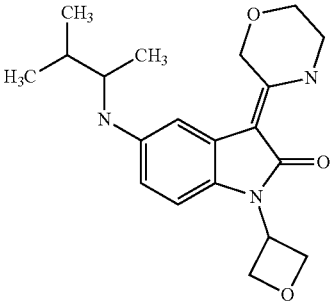 | 0.169 | 0.019 |
| 67 | 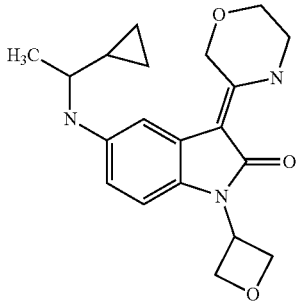 | 0.225 | 0.037 |
| 68 | 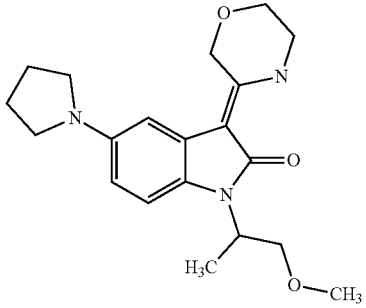 | 0.624 | 0.134 |
| 69 | 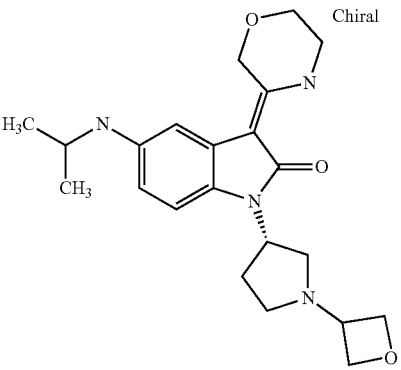 | 0.055 | 0.141 |

| # | Formula | CI IC$_{50}$/[μM] | HT22 IC$_{50}$/[μM] |
|---|---|---|---|
| 70 | | 0.193 | 1.149 |
| 71 | | 0.093 | 0.131 |
| 72 | | 0.140 | 0.006 |
| 73 | | 0.066 | 0.264 |

-continued

| # | Formula | CI IC$_{50}$/[μM] | HT22 IC$_{50}$/[μM] |
|---|---------|---|---|
| 74 | | 0.046 | 0.144 |
| 75 | | 0.072 | 0.073 |
| 76 | | 0.043 | 0.024 |
| 77 | | 0.022 | 0.048 |

-continued
| # | Formula | CI IC$_{50}$/[μM] | HT22 IC$_{50}$/[μM] |
|---|---|---|---|
| 78 | 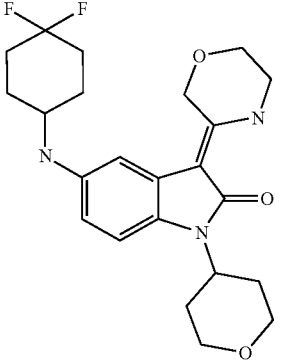 | 0.089 | 0.037 |
| 79 | 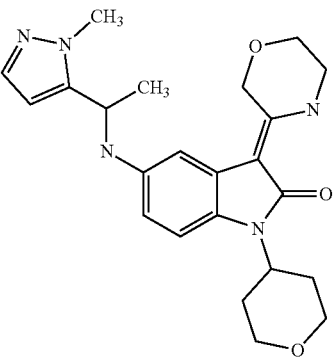 | 0.020 | 0.221 |
| 80 | 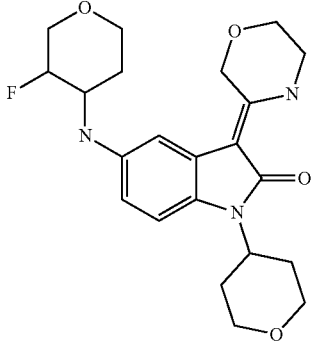 | 0.084 | 0.345 |
| 81 | 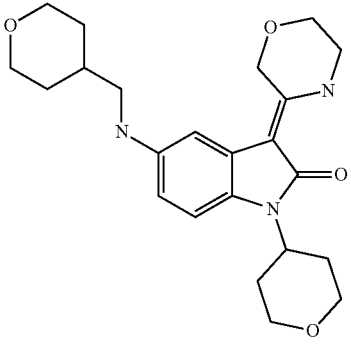 | 0.130 | 0.233 |

-continued

| # | Formula | CI IC$_{50}$/[μM] | HT22 IC$_{50}$/[μM] |
|---|---------|-------------------|---------------------|
| 82 | | 0.091 | 0.026 |
| 83 | | 0.011 | 2.075 |
| 84 | | 0.333 | 0.141 |
| 85 | | 0.069 | 0.264 |
| 86 | | 0.069 | 1.112 |

-continued
| # | Formula | CI IC$_{50}$/[μM] | HT22 IC$_{50}$/[μM] |
|---|---------|-------------------|---------------------|
| 87 | 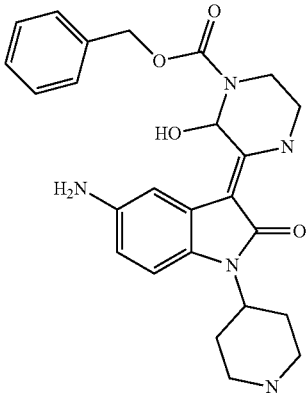 | 0.332 | 1.002 |
| 88 | 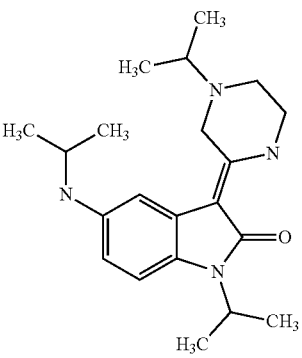 | 0.068 | 0.010 |
| 89 | 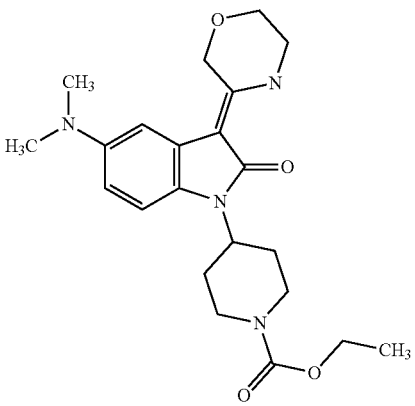 | 0.197 | 0.493 |
| 90 | 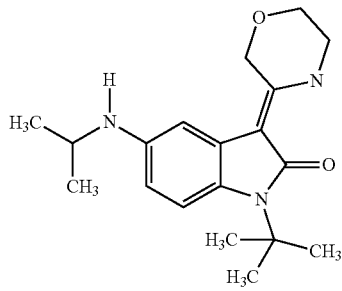 | 0.428 | 0.032 |

-continued
| # | Formula | CI IC$_{50}$/[μM] | HT22 IC$_{50}$/[μM] |
|---|---|---|---|
| 91 | 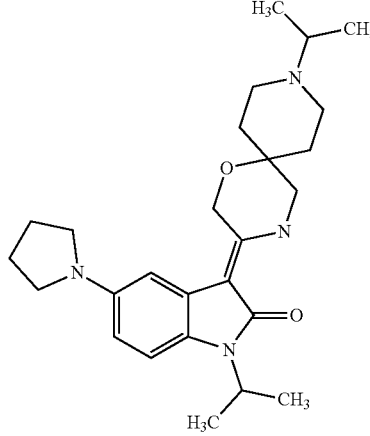 | 0.242 | 0.009 |
| 92 | 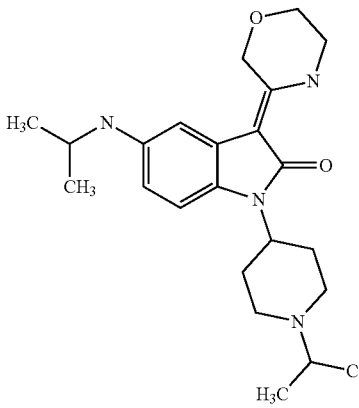 | 0.106 | 0.044 |
| 93 | 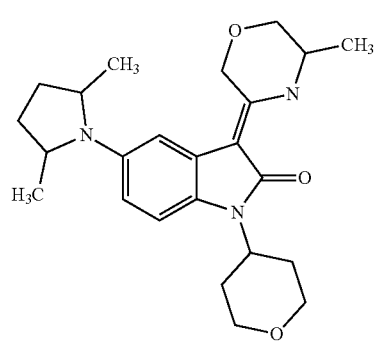 | 0.024 | 0.101 |
| 94 | 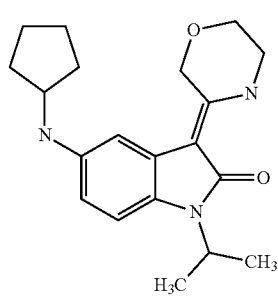 | 0.558 | 0.027 |

-continued

| # | Formula | CI IC$_{50}$/[μM] | HT22 IC$_{50}$/[μM] |
|---|---------|-------------------|---------------------|
| 95 | | 0.151 | 0.006 |
| 96 | | 0.063 | 0.041 |
| 97 | | 0.344 | 0.017 |
| 98 | | 0.187 | 0.166 |

-continued

| # | Formula | CI IC$_{50}$/[μM] | HT22 IC$_{50}$/[μM] |
|---|---------|-------------------|---------------------|
| 99 | | 0.451 | 0.163 |
| 100 | | 0.034 | 0.397 |
| 101 | | 0.202 | 0.369 |
| 102 | | 0.109 | 0.003 |

-continued
| # | Formula | CI IC$_{50}$/[μM] | HT22 IC$_{50}$/[μM] |
|---|---|---|---|
| 103 | 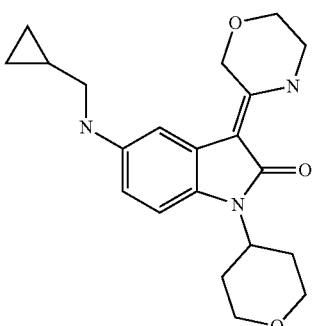 | 0.076 | 0.105 |
| 104 | 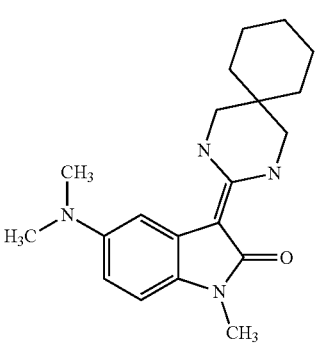 | 0.704 | |
| 105 | 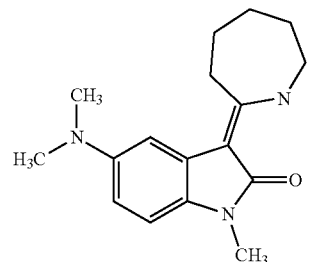 | 0.064 | 0.091 |
| 106 | 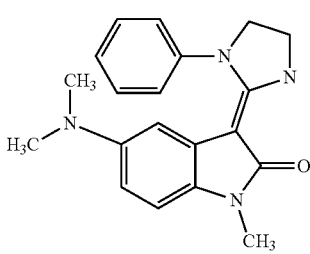 [SMILES: CN(C)c1ccc2c(c1)/C(=C1/NCCN1c1ccccc1)C(=O)N2C] | 0.327 | 0.142 |
| 107 | 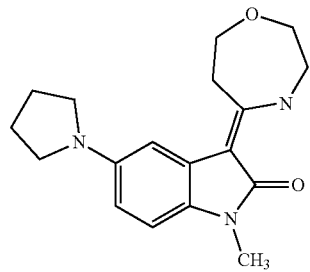 | 0.299 | 0.069 |

-continued

| # | Formula | CI IC$_{50}$/[µM] | HT22 IC$_{50}$/[µM] |
|---|---|---|---|
| 108 | | 0.118 | 0.128 |
| 109 | | 0.014 | 0.160 |
| 110 | | 0.264 | 0.019 |
| 111 | | 0.119 | 0.249 |

-continued

| # | Formula | CI IC$_{50}$/[μM] | HT22 IC$_{50}$/[μM] |
|---|---------|-------------------|---------------------|
| 112 | | 0.352 | 0.086 |
| 113 | | 0.106 | 0.018 |
| 114 | | 0.058 | 0.104 |
| 115 | | 0.080 | 0.030 |
| 116 | | 0.539 | 0.009 |

-continued

| # | Formula | CI IC$_{50}$/[μM] | HT22 IC$_{50}$/[μM] |
|---|---------|-------------------|---------------------|
| 117 | | 0.738 | 0.022 |
| 118 | | 0.420 | 0.033 |
| 119 | | 0.422 | 0.439 |
| 120 | | 0.235 | 0.051 |

| # | Formula | CI IC$_{50}$/[μM] | HT22 IC$_{50}$/[μM] |
|---|---------|-------------------|---------------------|
| 121 | | 0.075 | 0.192 |
| 122 | | 0.275 | 0.944 |
| 123 | | 0.916 | 0.017 |
| 124 | | 0.259 | 0.015 |

-continued
| # | Formula | CI IC$_{50}$/[μM] | HT22 IC$_{50}$/[μM] |
|---|---|---|---|
| 125 | 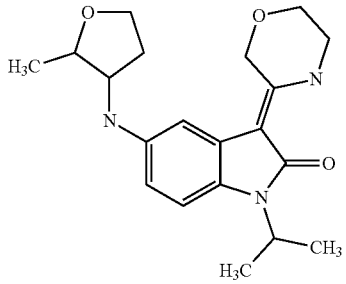 | 0.050 | 0.112 |
| 126 | 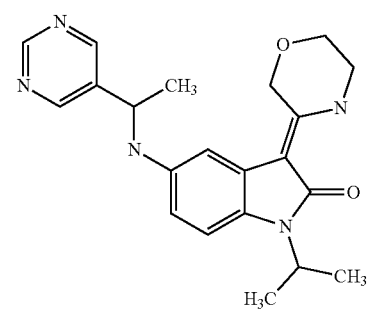 | 0.085 | 0.179 |
| 127 | 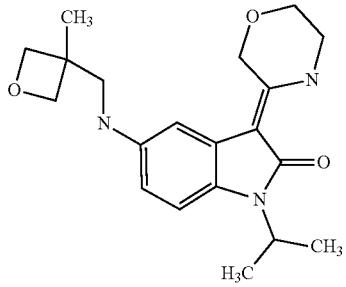 | 0.082 | 0.176 |
| 128 | 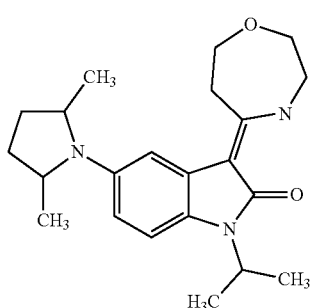 | 0.044 | 0.047 |
| 129 | 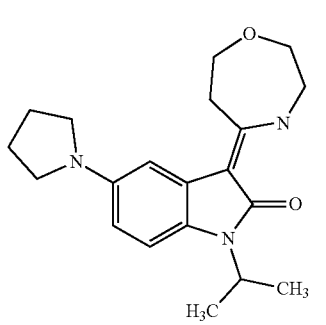 | 0.702 | 0.023 |

-continued

| # | Formula | CI IC$_{50}$/[μM] | HT22 IC$_{50}$/[μM] |
|---|---------|-------------------|---------------------|
| 130 | | 0.877 | 0.045 |
| 131 | | 0.189 | 0.111 |
| 132 | | 0.055 | 0.021 |
| 133 | | 0.049 | 0.023 |
| 134 | | 0.062 | 0.044 |

-continued
| # | Formula | CI IC$_{50}$/[μM] | HT22 IC$_{50}$/[μM] |
|---|---------|-------------------|---------------------|
| 135 | 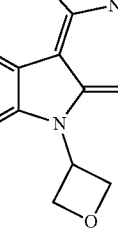 | 0.082 | 0.158 |
| 136 |  | 0.213 | 0.018 |
| 137 | 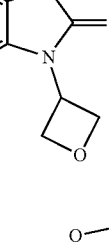 | 0.138 | 0.886 |
| 138 | 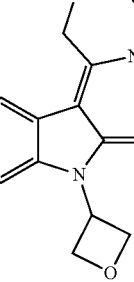 | 0.206 | 0.006 |

-continued
| # | Formula | CI IC$_{50}$/[μM] | HT22 IC$_{50}$/[μM] |
|---|---------|-------------------|---------------------|
| 139 | 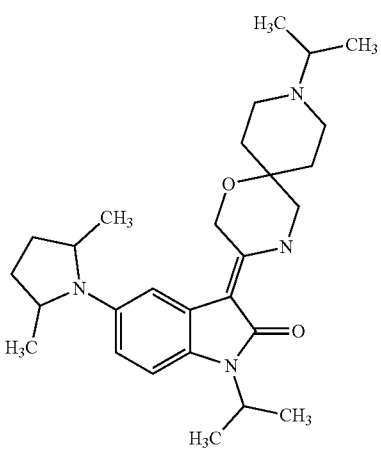 | 0.308 | 0.018 |
| 140 | 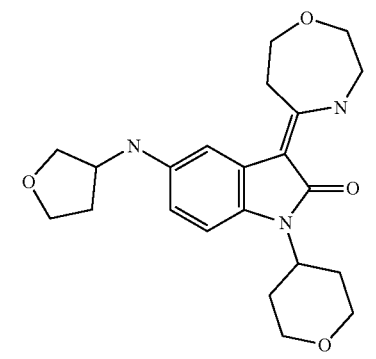 | 0.084 | 0.524 |
| 141 | 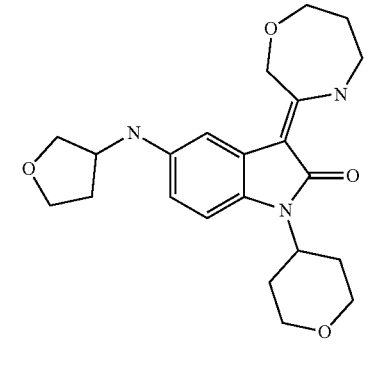 | 0.104 | 0.646 |
| 142 | 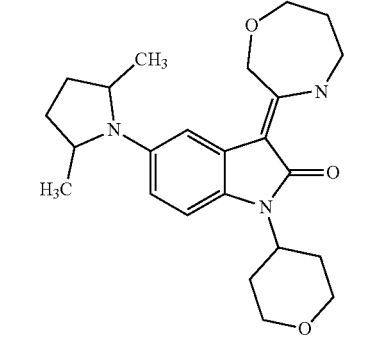 | 0.116 | 0.094 |

-continued

| # | Formula | CI IC$_{50}$/[μM] | HT22 IC$_{50}$/[μM] |
|---|---------|-------------------|---------------------|
| 143 | | 0.079 | 0.110 |
| 144 | | 0.049 | 0.085 |
| 145 | | 0.183 | 0.004 |
| 146 | | 0.066 | 0.211 |
| 147 | | 0.069 | 0.422 |

-continued
| # | Formula | CI IC$_{50}$/[μM] | HT22 IC$_{50}$/[μM] |
|---|---|---|---|
| 148 | 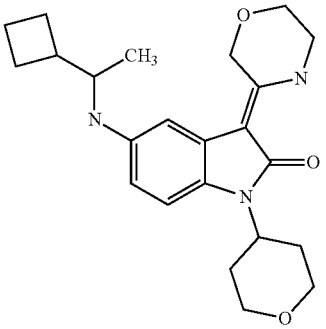 | 0.039 | 0.016 |
| 149 | 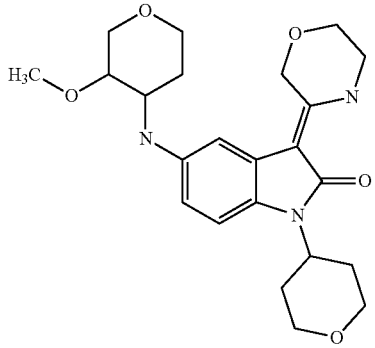 | 0.161 | 2.939 |
| 150 | 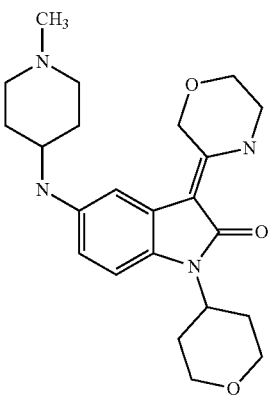 | 0.048 | 0.286 |
| 151 | 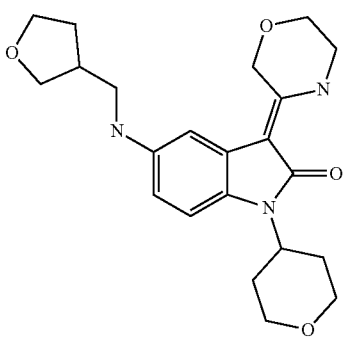 | 0.232 | 0.184 |

-continued
| # | Formula | CI IC$_{50}$/[µM] | HT22 IC$_{50}$/[µM] |
|---|---|---|---|
| 152 | 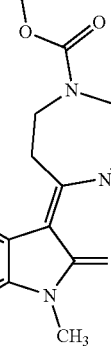 | 0.477 | 0.047 |
| 153 | 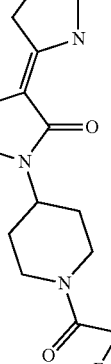 | 0.016 | 0.170 |
| 154 | 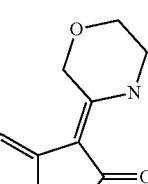 | 0.193 | 0.018 |
| 155 | 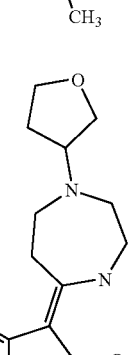 | 0.264 | 0.214 |

-continued

| # | Formula | CI IC$_{50}$/[µM] | HT22 IC$_{50}$/[µM] |
|---|---------|-------------------|---------------------|
| 156 | | 0.077 | 0.071 |
| 157 | | 0.691 | 1.655 |
| 158 | | 0.243 | 2.074 |
| 159 | | 0.120 | 0.080 |
| 160 | | 0.829 | 0.471 |

-continued

| # | Formula | CI IC$_{50}$/[μM] | HT22 IC$_{50}$/[μM] |
|---|---|---|---|
| 161 | | 0.957 | 0.020 |
| 162 | | 0.464 | 0.061 |
| 163 | | 0.172 | 0.052 |
| 164 | | 0.172 | 0.030 |

-continued
| # | Formula | CI IC$_{50}$/[μM] | HT22 IC$_{50}$/[μM] |
|---|---|---|---|
| 165 | 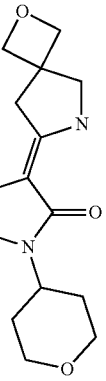 | 0.181 | 0.253 |
| 166 | 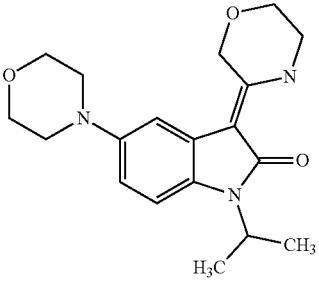 | 0.075 | 0.649 |
| 167 | 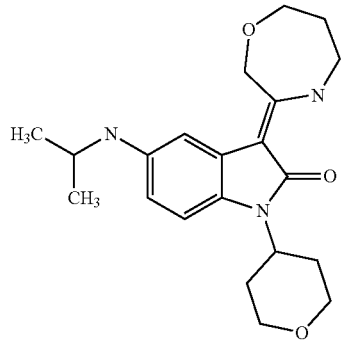 | 0.065 | 0.134 |
| 168 | 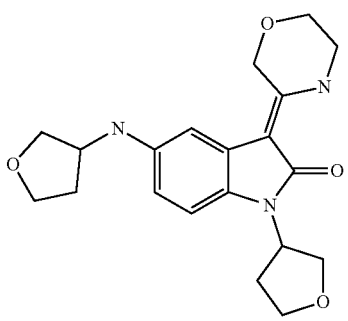 | 0.041 | 0.439 |

-continued

| # | Formula | CI IC$_{50}$/[μM] | HT22 IC$_{50}$/[μM] |
|---|---------|-------------------|---------------------|
| 169 | | 0.944 | 0.336 |
| 170 | | 0.023 | 0.159 |
| 171 | | 0.206 | 0.023 |
| 172 | | 0.078 | 0.279 |

-continued

| # | Formula | CI IC$_{50}$/[μM] | HT22 IC$_{50}$/[μM] |
|---|---------|-------------------|---------------------|
| 173 | 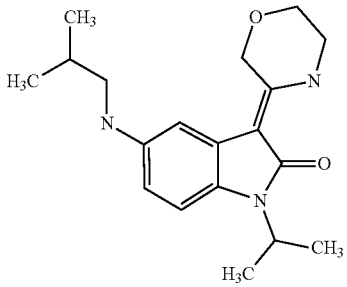 | 0.367 | 0.032 |
| 174 | 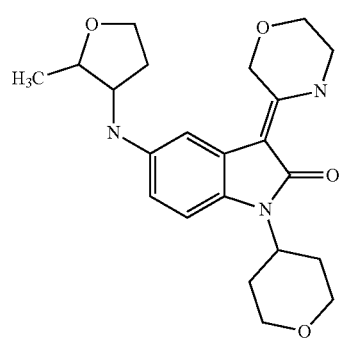 | 0.039 | 0.143 |
| 175 | 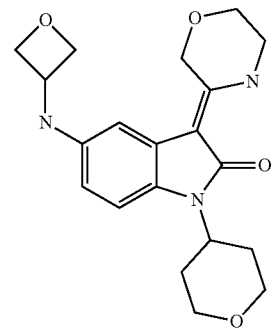 | 0.097 | 1.187 |

EXPERIMENTAL SECTION

The following examples are intended to illustrate the invention, without restricting its scope.

As a rule, melting points, IR, $^1$H-NMR and/or mass spectra have been obtained for the compounds prepared. Unless otherwise stated, Rf values were obtained using ready-made silica gel 60 F254 TLC plates (E-. Merck, Darmstadt, item no. 1.05714) without chamber saturation. The ratios given for the eluant refer to units by volume of the solvents in question. Chromatographic purification was done using silica gel supplied by E. Merck, Darmstadt (Silica gel 60, 0.040-0.063 mm), item no. 1.09385.2500).

The following abbreviations can be used in the following examples:

BOC tBuOC(O
CH Cyclohexane
CM Dichloromethane
DIPEA Diisopropylamine
DMSO Dimethylsulphoxide
DMF NN-Dimethylformamide
EA Ethyl acetate
ESI Electrospray ionisation
h Hour(s)
HPLC High performance liquid chromatography
M Molar
MeOH Methanol
EtOH Ethanol
min Minute(s)
μL Milliliters
Microliters
mmol Millimoles
μmol Micromoles
MPLC Medium pressure liquid chromatography
MS Mass spectrometry
NMP N-Methyl-pyrrolidinone
Pd/C Palladium on charcoal
PE petroleum ether
Rf Retention factor
Rt Retention time
sat. Saturated
Tert. Tertiary
TLC Thin layer chromatography
TFA Trifluoroacetic acid
THF Tetrahydrofurane
TBME tert-Butyl methyl ether
UPLC Ultra performance liquid chromatography All references to brine refer to a saturated aqueous solution of sodium chloride. Unless otherwise indicated, all temperatures are expressed in ° C. (degrees Centigrade). All reactions are conducted not under an inert atmosphere at room temperature unless otherwise noted.

EXAMPLES

Example 1

HPLC/UPLC Methods

Method A

| Device: Waters Alliance with DAD and MS detector Column: Waters XBridge C18, 4.6 × 30 mm, 3.5 μm | | | | |
|---|---|---|---|---|
| Time [min] | % Solvent A [H$_2$O, 0.1% NH$_3$] | % Solvent B [MeOH] | Flow rate [mL/min] | Temperature [° C.] |
| 0.00 | 95 | 5 | 4.0 | 60 |
| 0.20 | 95 | 5 | 4.0 | 60 |
| 1.50 | 0 | 100 | 4.0 | 60 |
| 1.75 | 0 | 100 | 4.0 | 60 |

Method B

| Device: Waters Alliance with DAD and MS detector Column: Waters SunFire C18, 4.6 × 30 mm, 3.5 μm | | | | |
|---|---|---|---|---|
| Time [min] | % Solvent A [H$_2$O, 0.1% TFA] | % Solvent B [MeOH] | Flow rate [mL/min] | Temperature [° C.] |
| 0.00 | 95 | 5 | 4.0 | 60 |
| 1.60 | 0 | 100 | 4.0 | 60 |
| 1.85 | 0 | 100 | 4.0 | 60 |
| 1.90 | 95 | 5 | 4.0 | 60 |

Method C

| Device: Waters Alliance with DAD and MS detector Column: Waters XBridge C18, 4.6 × 30 mm, 3.5 μm | | | | |
|---|---|---|---|---|
| Time [min] | % Solvent A [H$_2$O, 0.1% TFA] | % Solvent B [MeOH] | Flow rate [mL/min] | Temperature [° C.] |
| 0.00 | 95 | 5 | 4.8 | 60 |
| 1.60 | 0 | 100 | 4.8 | 60 |
| 1.85 | 0 | 100 | 4.8 | 60 |
| 1.90 | 95 | 5 | 4.8 | 60 |

Method D

| Device: Waters Acquity with DAD and MS detector Column: Waters SunFire C18, 2.1 × 20 mm, 2.5 μm | | | | |
|---|---|---|---|---|
| Time [min] | % Solvent A [H$_2$O, 0.1% TFA] | % Solvent B [MeOH] | Flow rate [mL/min] | Temperature [° C.] |
| 0.00 | 99 | 1 | 1.3 | 60 |
| 0.15 | 99 | 1 | 1.3 | 60 |
| 1.10 | 0 | 100 | 1.3 | 60 |
| 1.25 | 0 | 100 | 1.3 | 60 |

Method E

| Device: Waters Acquity with DAD and MS detector Column: Supelco Ascentis Express C18, 2.1 × 50 mm, 2.7 μm | | | | |
|---|---|---|---|---|
| Time [min] | % Solvent A [H$_2$O, 0.1% TFA] | % Solvent B [ACN, 0.08% TFA] | Flow rate [mL/min] | Temperature [° C.] |
| 0.00 | 95 | 5 | 1.5 | 60 |
| 0.70 | 1 | 99 | 1.5 | 60 |
| 0.80 | 1 | 99 | 1.5 | 60 |
| 0.81 | 95 | 5 | 1.5 | 60 |

Method F

| Device: Waters Alliance with DAD and MS detector Column: Waters XBridge C18, 4.6 × 30 mm, 3.5 μm | | | | |
|---|---|---|---|---|
| Time [min] | % Solvent A [H$_2$O, 0.1% TFA] | % Solvent B [MeOH, 0.1% TFA] | Flow rate [mL/min] | Temperature [° C.] |
| 0.00 | 95 | 5 | 4.0 | 60 |
| 0.20 | 95 | 5 | 4.0 | 60 |
| 1.50 | 0 | 100 | 4.0 | 60 |
| 1.75 | 0 | 100 | 4.0 | 60 |
| 1.85 | 95 | 5 | 4.0 | 60 |

Method G

| Device: Waters Alliance with DAD and MS detector Column: Waters XBridge C18, 4.6 × 30 mm, 3.5 μm | | | | |
|---|---|---|---|---|
| Time [min] | % Solvent A [H$_2$O, 0.1% TFA] | % Solvent B [MeOH] | Flow rate [mL/min] | Temperature [° C.] |
| 0.00 | 95 | 5 | 4.0 | 60 |
| 1.60 | 0 | 100 | 4.0 | 60 |
| 1.85 | 0 | 100 | 4.0 | 60 |
| 1.90 | 95 | 5 | 4.0 | 60 |

Method H

| Device: Waters Alliance with 2695 with PDA detector 2996 and micromass ZQ 2000 Column: Microsorb C18, 4.6 × 20 mm, 5 μm | | | | |
|---|---|---|---|---|
| Time [min] | % Solvent A [H$_2$O, 0.15% TFA] | % Solvent B [MeOH] | Flow rate [mL/min] | Temperature [° C.] |
| 0.00 | 95 | 5 | 5.2 | rt |
| 0.25 | 95 | 5 | 5.2 | rt |
| 1.90 | 0 | 100 | 5.2 | rt |
| 2.05 | 0 | 100 | 5.2 | rt |
| 2.15 | 95 | 5 | 5.2 | rt |
| 2.25 | 95 | 5 | 5.2 | rt |
| 2.30 | 95 | 5 | 0.1 | rt |

Method I

| Device: Waters Acquity with DAD and MS detector Column: Waters SunFire C18, 2.1 × 30 mm, 2.5 μm | | | | |
|---|---|---|---|---|
| Time [min] | % Solvent A [H$_2$O, 0.13% TFA] | % Solvent B [MeOH, 0.05% TFA] | Flow rate [mL/min] | Temperature [° C.] |
| 0.00 | 99 | 1 | 1.2 | 60 |
| 0.15 | 99 | 1 | 1.2 | 60 |
| 1.10 | 0 | 100 | 1.2 | 60 |
| 1.25 | 0 | 100 | 1.2 | 60 |

Method J

| Device: Waters Alliance with DAD and MS detector<br>Column: Waters XBridge C18, 4.6 × 30 mm, 3.5 μm | | | | |
|---|---|---|---|---|
| Time [min] | % Solvent A [H₂O, 0.1% TFA] | % Solvent B [MeOH] | Flow rate [mL/min] | Temperature [° C.] |
| 0.00 | 95 | 5 | 4.0 | 60 |
| 0.20 | 95 | 5 | 4.0 | 60 |
| 1.50 | 0 | 100 | 4.0 | 60 |
| 1.90 | 0 | 100 | 4.0 | 60 |
| 2.00 | 95 | 5 | 4.0 | 60 |

Method K

| Device: Waters Alliance with DAD and MS detector<br>Column: Waters XBridge C18, 4.6 × 30 mm, 3.5 μm | | | | |
|---|---|---|---|---|
| Time [min] | % Solvent A [H₂O, 0.1% TFA] | % Solvent B [MeOH] | Flow rate [mL/min] | Temperature [° C.] |
| 0.00 | 95 | 5 | 4.0 | 60 |
| 0.20 | 95 | 5 | 4.0 | 60 |
| 1.50 | 0 | 100 | 4.0 | 60 |
| 1.75 | 0 | 100 | 4.0 | 60 |
| 1.85 | 95 | 5 | 4.0 | 60 |

Method L

| Device: Waters Alliance with DAD and MS detector<br>Column: Waters XBridge C18, 4.6 × 30 mm, 3.5 μm | | | | |
|---|---|---|---|---|
| Time [min] | % Solvent A [H₂O, 0.1% TFA] | % Solvent B [MeOH] | Flow rate [mL/min] | Temperature [° C.] |
| 0.00 | 95 | 5 | 4.9 | 60 |
| 1.60 | 0 | 100 | 4.9 | 60 |
| 2.20 | 95 | 5 | 4.9 | 60 |

Method M

| Device: Waters Alliance with DAD and MS detector<br>Column: Waters XBridge C18, 4.6 × 30 mm, 3.5 μm | | | | |
|---|---|---|---|---|
| Time [min] | % Solvent A [H₂O, 0.1% NH₃] | % Solvent B [MeOH, 0.1% NH₃] | Flow rate [mL/min] | Temperature [° C.] |
| 0.00 | 95 | 5 | 4.0 | 60 |
| 0.20 | 95 | 5 | 4.0 | 60 |
| 1.50 | 0 | 100 | 4.0 | 60 |
| 1.75 | 0 | 100 | 4.0 | 60 |

Method N

| Device: Waters Alliance with DAD and MS detector<br>Column: Waters SunFire C18, 4.6 × 30 mm, 3.5 μm | | | | |
|---|---|---|---|---|
| Time [min] | % Solvent A [H₂O, 0.1% TFA] | % Solvent B [MeOH] | Flow rate [mL/min] | Temperature [° C.] |
| 0.00 | 95 | 5 | 4.0 | 60 |
| 0.20 | 95 | 5 | 4.0 | 60 |
| 1.50 | 0 | 100 | 4.0 | 60 |
| 1.75 | 0 | 100 | 4.0 | 60 |
| 1.85 | 95 | 5 | 4.0 | 60 |

Method O

| Device: Waters Acquity with DAD and MS detector<br>Column: Waters XBridge C18, 2.1 × 20 mm, 2.5 μm | | | | |
|---|---|---|---|---|
| Time [min] | % Solvent A [H₂O, 0.1% TFA] | % Solvent B [MeOH] | Flow rate [mL/min] | Temperature [° C.] |
| 0.00 | 95 | 5 | 1.4 | 60 |
| 0.05 | 95 | 5 | 1.4 | 60 |
| 1.00 | 0 | 100 | 1.4 | 60 |
| 1.10 | 0 | 100 | 1.4 | 60 |

Method P

| Device: Waters Acquity with DAD and MS detector<br>Column: Waters XBridge BEH C18, 2.1 × 30 mm, 1.7 μm | | | | |
|---|---|---|---|---|
| Time [min] | % Solvent A [H₂O, 0.13% TFA] | % Solvent B [MeOH, 0.08% TFA] | Flow rate [mL/min] | Temperature [° C.] |
| 0.00 | 99 | 1 | 1.3 | 60 |
| 0.05 | 99 | 1 | 1.3 | 60 |
| 0.35 | 0 | 100 | 1.3 | 60 |
| 0.50 | 0 | 100 | 1.3 | 60 |

Example 2

Synthesis of intermediates A1, A2, A4, A5, A7 to A9 and A11

Intermediate A1:

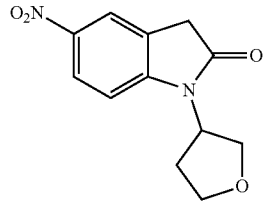 [SMILES: O=C1Cc2cc([N+](=O)[O-])ccc2N1C1CCOC1]

(2-Fluoro-5-nitro-phenyl)-acetic acid (4.60 g; 23.10 mmol) and tetrahydro-furan-3-ylamine (10.0 g; 114.78 mmol) in DMSO (20 mL) are stirred at 45° C. over night. HCl (aq. solution; 2M; 92.4 mL; 184.80 mmol) is added. After stirring for 1.5 h at 45° C. the resulting precipitate is filtered off, washed with water and dried.

MS (ESI⁺): m/z=249 [M+H]⁺

HPLC (Method B): $R_t$=1.0 min

The following intermediates were prepared in an analogous manner to intermediate A1:

| No. | Structure Comment | Educt 1 | Educt 2 | Mass signal(s) | $R_f$ value or $R_t$ |
|---|---|---|---|---|---|
| A2 | O₂N-[5-nitro-2-oxoindoline with tetrahydropyran-4-yl on N] | (2-Fluoro-5-nitro-phenyl)-acetic acid | Tetrahydro-pyran-4-ylamine | $(M + H)^+$ = 263 | 1.03 min (Method B) |
| A4 | O₂N-[5-nitro-2-oxoindoline with isopropyl on N] | (2-Fluoro-5-nitro-phenyl)-acetic acid | Isopropylamine | $(M + H)^+$ = 221 | |
| | HCl (4M, aq. solution) is used instead of HCl (2M, aq. solution) | | | | |
| A5 | O₂N-[5-nitro-2-oxoindoline with 1,4-dioxepan-6-yl on N] | (2-Fluoro-5-nitro-phenyl)-acetic acid | 1,4-Dioxepan-6-amine | $(M + H)^+$ = 279 | 1.08 min (Method A) |
| | Purification by MPLC (DCM/MeOH; 0/0 -> 99/1) | | | | |
| A7 | O₂N-[5-nitro-2-oxoindoline with N-Boc-pyrrolidin-3-yl on N] | (2-Fluoro-5-nitro-phenyl)-acetic acid | (S)-3-Amino-pyrrolidine-1-carboxylic acid tert-butyl ester | $(M + H)^+$ = 346 | 1.34 min (Method A) |
| A8 | O₂N-[5-nitro-2-oxoindoline with tert-butyl on N] | (2-Fluoro-5-nitro-phenyl)-acetic acid | tert-Butylamine | $(M + H)^+$ = 235 | 0.77 min (Method O) |
| | Additional amine (6 eq.) is added. Mixture is stirred at 100° C. over night | | | | |

-continued

| No. | Structure | Educt 1 Comment | Educt 2 | Mass signal(s) | $R_f$ value or $R_t$ |
|---|---|---|---|---|---|
| A9 | 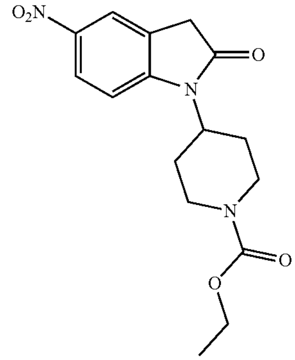 [SMILES: CCOC(=O)N1CCC(N2C(=O)Cc3cc([N+](=O)[O-])ccc32)CC1] | (2-Fluoro-5-nitro-phenyl)-acetic acid | 4-Amino-piperidine-1-carboxylic acid ethyl ester | $(M + H)^+ = 334$ | 1.24 min (Method B) |
| A11 | 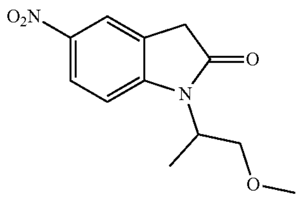 [SMILES: COCC(C)N1C(=O)Cc2cc([N+](=O)[O-])ccc21] | (2-Fluoro-5-nitro-phenyl)-acetic acid | 2-Methoxy-1-methyl-ethylamine | $(M + H)^+ = 251$ | 1.08 min (Method B) |

Example 3

Synthesis of Intermediate A3

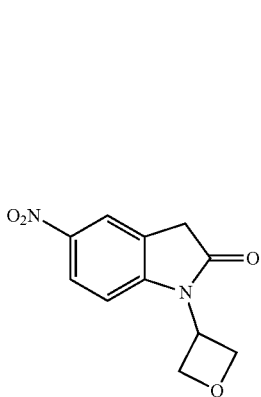 [SMILES: O=C1Cc2cc([N+](=O)[O-])ccc2N1C1COC1]

Step 1:

(2-Fluoro-5-nitro-phenyl)-acetic acid (500 mg; 2.51 mmol) and oxetan-3-ylamine (936 mg; 12.81 mmol) in DMSO (2 mL) are stirred at 45° C. over night. The mixture is purified by preparative HPLC (eluent A. water+0.15% conc. ammonia, eluent B: MeOH).

MS (ESI⁺): m/z=251 [M−H]⁻

(Method A): $R_t$=0.66 min

Step 2:

Intermediate A3 Step 1 (462 mg; 0.92 mmol) and TBTU (0.71 g; 2.20 mmol) in DMF (8 mL) are stirred at room temperature over night. The resulting precipitate is filtered off and dried.

MS (ESI⁺): m/z=235 [M+H]⁺

HPLC (Method A): $R_t$=0.95 min

Example 4

Synthesis of Intermediate A6

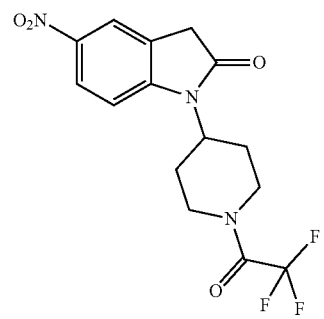 [SMILES: O=C1Cc2cc([N+](=O)[O-])ccc2N1C1CCN(C(=O)C(F)(F)F)CC1]

Step 1:

1,3-Dihydro-1-(piperidin-4-yl)-(2H)-indol-2-one (5.51 g; 25.49 mmol) and TEA (7.16 mL; 50.99 mmol) in DCM (30 mL) are cooled in an ice bath. Trifluoroacetic anhydride (4.25 mL; 30.59 mmol) is added drop wise. The mixture is stirred at room temperature for 2 h. The mixture is diluted with NaHCO₃ (aq. solution; 9%; 20 mL). After the gas development has stopped, the mixture is further diluted with DCM and water. The organic layer is separated, dried and evaporated. The residue is purified by MPLC (DCM/MeOH; 1/0→97/3).

MS (ESI⁺): m/z=313 [M+H]⁺

HPLC (Method A): $R_t$=1.25 min

Step 2:

Intermediate A6 Step 1 (8.02 g; 25.68 mmol) is solved in conc. sulphuric acid (45 mL) and cooled to −5° C. A cooled mixture of conc. sulphuric acid (15 mL) and conc. nitric acid (1.80 mL; 28.25 mmol) is added drop wise. After stirring for 1 h at −5° C. the mixture is poured on ice water. The resulting precipitate is filtered off and dried. The residue is taken up in DCM. The organic layer is washed with NaHCO₃ (aq. solution; 9%), separated, dried and evaporated.

MS (ESI⁺): m/z=358 [M+H]⁺
HPLC (Method A): R$_t$=1.22 min

Example 5

Synthesis of Intermediate A10

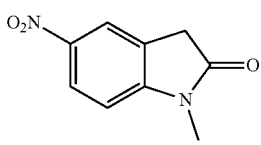

To a cooled mixture of sodium nitrate (12.71 g; 149.48 mmol) and conc. sulphuric acid (22.9 mL; 407.68 mmol) additional conc. sulphuric acid (40 mL) is added drop wise. 1-Methyl-1,3-dihydro-indol-2-one (20.0 g; 135.89 mmol) is taken up in conc. sulphuric acid (120 mL) and added drop wise to the cooled nitrosulphuric acid. The mixture is allowed to warm up to room temperature over night. The mixture is poured on ice water. The resulting precipitate is filtered off, washed with water and dried. The residue is taken up in DCM, washed with water and brine, separated, dried and evaporated.

MS (ESI⁺): m/z=193 [M+H]⁺
HPLC (Method H): R$_t$=0.90 min

Example 6

Synthesis of Intermediates B1, B2, B4, B6, B7, B9 and B10

The following intermediates are prepared according to the given references or are commercially available:

| Name | Structure | Reference |
|---|---|---|
| B1 |  | WO2006/72350 |
| B2 |  | WO2005/111029 |
| B4 |  | WO2010/68520 |
| B6 | 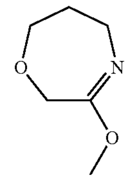 | WO2010/68520 |
| B7 | 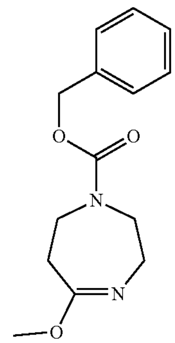 [SMILES: COC1=NCCN(C(=O)OCc2ccccc2)CC1] | EP1790641 |
| B9 | 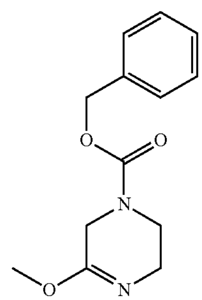 [SMILES: COC1=NCCN(C(=O)OCc2ccccc2)C1] | WO2008/76356 |
| B10 | 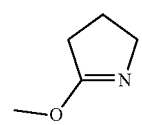 | WO2004/60376 |

Example 7

Synthesis of Intermediates B3, B5 and B8

Intermediate B3:

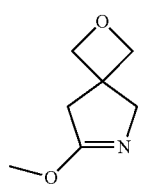

2-Oxa-6-aza-spiro[3.4]octan-7-one (1.00 g; 7.87 mmol) and trimethyloxonium tetrafluoroborate (1.28 g; 8.65 mmol) in DCM (120 mL) are stirred at room temperature over night. The mixture is diluted with saturated NaHCO₃ solution until gas development stops. The organic layer is separated, dried and evaporated.

MS (ESI⁺): m/z=142 [M+H]⁺

The following intermediates are prepared in an analogous manner to intermediate B3:

| No. | Structure | Educt 1 Comment | Educt 2 | Mass signal(s) | $R_f$ value or $R_t$ |
|---|---|---|---|---|---|
| B5 | 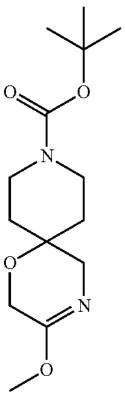 [SMILES: COC1=NCC2(CCN(C(=O)OC(C)(C)C)CC2)OC1] | 3-Oxo-1-oxa-4,9-diaza-spiro[5.5]un-decane-9-carboxylic acid tert-butyl ester | Trimethyl-oxonium tertafluoro-borate | $(M + H)^+ = 285$ | |
| B8 | 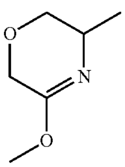 | 5-Methyl-morpholin-3-one | Trimethyl-oxonium tertafluoro-borate | | |

Example 8

Synthesis of intermediates C1-C3, C5-C8, C10-C12, C14, C16, C18, C20-C25, C27-C29, C32-C36

Intermediate C1:

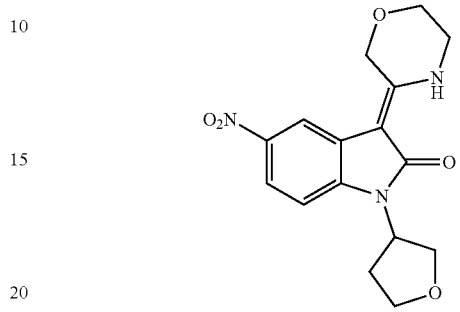

Intermediate A1 (700 mg; 2.82 mmol) and Intermediate B1 (714 mg; 6.20 mmol) are stirred at 130° C. for 20 min in a microwave. The resulting precipitate is suspended in MeOH, filtered off and dried.

MS (ESI$^+$): m/z=332 [M+H]$^+$
HPLC (Method B): $R_t$=1.29 min

The following intermediates were prepared in an analogous manner to intermediate C1:

| No. | Structure | Educt 1 Comment | Educt 2 | Mass signal(s) | $R_f$ value or $R_t$ |
|---|---|---|---|---|---|
| C2 | 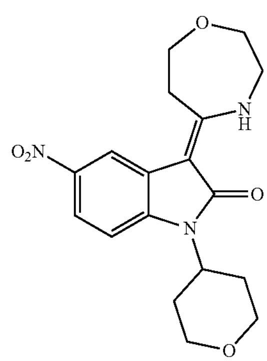 [SMILES: O=C1/C(=C2/CCOCCN2)c2cc([N+](=O)[O-])ccc2N1C1CCOCC1] | A2 | B2 | $(M + H)^+ = 360$ | 1.29 min (Method B) |
| C3 | 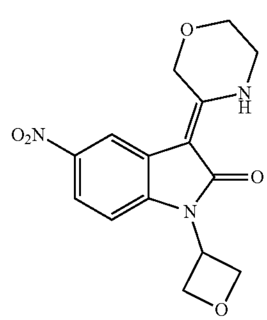 [SMILES: O=C1/C(=C2/COCCN2)c2cc([N+](=O)[O-])ccc2N1C1COC1] | A3 | B1 | $(M + H)^+ = 318$ | 1.19 min (Method A) |

Combined reaction time in microwave 2.5 h at 130° C.

-continued
| No. | Structure Comment | Educt 1 | Educt 2 | Mass signal(s) | $R_f$ value or $R_t$ |
|---|---|---|---|---|---|
| C5 | | A2 | B1 | $(M + H)^+ =$ 346 | 0.84 min (Method D) |
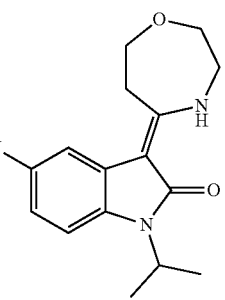
After 20 min additional B1 is added and the mixture is stirred for 20 min at 130° C.
| C6 | | A4 | B2 | $(M + H)^+ =$ 318 | 1.31 min (Method N) |
|---|---|---|---|---|---|
| C7 | | A2 | B3 | $(M + H)^+ =$ 372 | 1.22 min (Method B) |
|---|---|---|---|---|---|
The mixture is stirred for 40 min at 130° C. and for 20 min at 140° C.
| C8 | 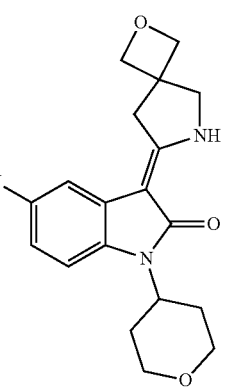 | 1-Methyl-5-nitro-1,3-dihydro-indol-2-one | B1 | $(M + H)^+ =$ 276 | 0.58 min (Method O) |
|---|---|---|---|---|---|

-continued

| No. | Structure / Comment | Educt 1 | Educt 2 | Mass signal(s) | $R_f$ value or $R_t$ |
|---|---|---|---|---|---|
| C10 | | A4 | B1 | $(M + H)^+ =$ 304 | 1.24 min (Method C) |
| | The mixture is stirred for 40 min at 130° C. and for 20 min at 140° C. | | | | |
| C11 | | A5 | B1 | $(M + H)^+ =$ 362 | 1.27 min (Method A) |
| | Combined reaction time in microwave 165 min at 130° C. | | | | |
| C12 | | A4 | B4 | $(M + H)^+ =$ 302 | 1.45 min (Method A) |
| C14 | | A6 | B1 | $(M + H)^+ =$ 441 | 1.41 min (Method B) |
| | Combined reaction time in microwave 40 min at 130° C. | | | | |

-continued
| No. | Structure Comment | Educt 1 | Educt 2 | Mass signal(s) | $R_f$ value or $R_t$ |
|---|---|---|---|---|---|
| C16 | 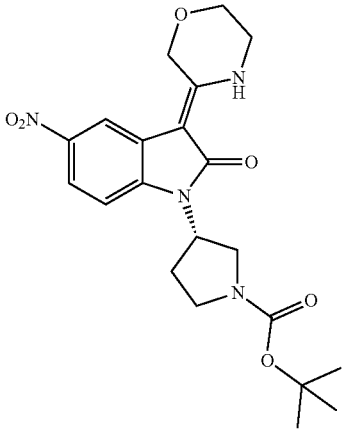 [SMILES: CC(C)(C)OC(=O)N1CC[C@H](N2C(=O)/C(=C3/COCCN3)c3cc([N+](=O)[O-])ccc32)C1] | A7 | B1 | $(M + H)^+ =$ 431 | 1.46 min (Method A) |
| C18 | 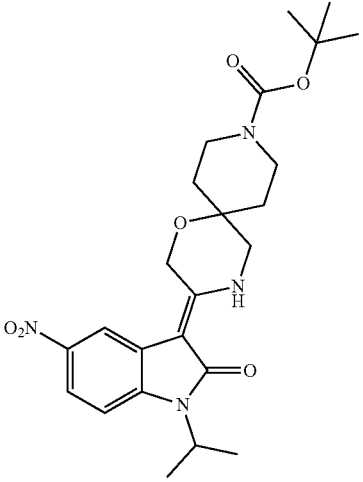 [SMILES: CC(C)N1C(=O)/C(=C2/COC3(CCN(C(=O)OC(C)(C)C)CC3)CN2)c2cc([N+](=O)[O-])ccc21] | A4 | B5 | $(M + H)^+ =$ 473 | 1.65 min (Method B) |
| C20 | 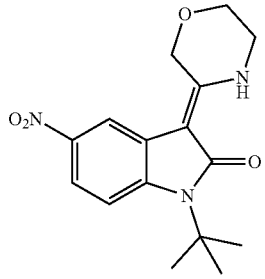 [SMILES: CC(C)(C)N1C(=O)/C(=C2/COCCN2)c2cc([N+](=O)[O-])ccc21] | A8 | B1 | $(M + H)^+ =$ 318 | 1.45 min (Method A) |
Combined reaction time in microwave 4.5 h at 130° C. Purification by MPLC (CH/EA = 4/1)

-continued

| No. | Structure Comment | Educt 1 | Educt 2 | Mass signal(s) | $R_f$ value or $R_t$ |
|---|---|---|---|---|---|
| C21 | | A2 | B6 | (M + H)⁺ = 360 | 1.31 min (Method B) |
| C22 | | A9 | B1 | (M + H)⁺ = 417 | 1.43 min (Method B) |
| C23 | | A10 | B7 | (M + H)⁺ = 423 | 1.64 min (Method H) |

| No. | Structure Comment | Educt 1 | Educt 2 | Mass signal(s) | $R_f$-value or $R_t$ |
|---|---|---|---|---|---|
| C24 | | A2 | B7 | $(M + H)^+ = 493$ | 1.5 min (Method B) |
| C25 | | A10 | B2 | $(M + H)^+ = 290$ | 1.29 min (Method H) |
| C27 | | A2 | B8 | $(M + H)^+ = 260$ | 1.36 min (Method B) |
| | Additional reaction time in microwave 30 min at 140° C. Purification by preparative HPLC (eluent A. water + 0.1% conc. ammonia, eluent B: MeOH) | | | | |
| C28 | | A11 | B1 | $(M + H)^+ = 334$ | 1.32 min (Method B) |
| | Combined reaction time in microwave 40 min at 130° C. | | | | |

-continued
| No. | Structure Comment | Educt 1 | Educt 2 | Mass signal(s) | $R_f$ value or $R_t$ |
|---|---|---|---|---|---|
| C29 | 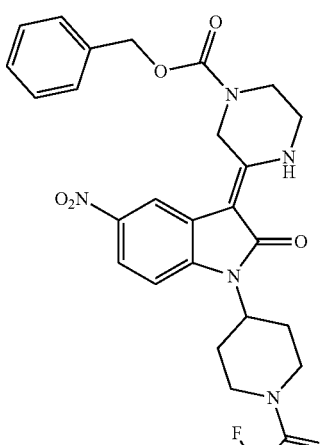 | A6 | B9 | $(M + H)^+ = 574$ | 0.98 min (Method B) |
Combined reaction time in microwave 40 min at 130° C.
| C32 | 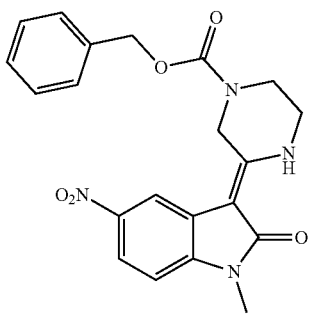 [SMILES: CN1C(=O)/C(=C2/CN(C(=O)OCc3ccccc3)CCN2)c2cc([N+](=O)[O-])ccc21] | A10 | B9 | $(M + H)^+ = 409$ | 1.45 min (Method A) |
|---|---|---|---|---|---|
| C33 | 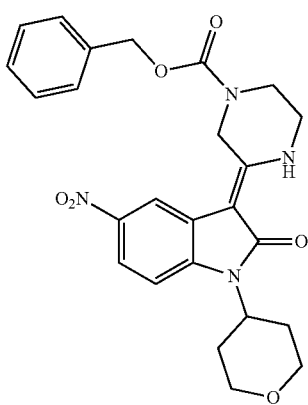 [SMILES: O=C(OCc1ccccc1)N1CCN/C(=C2\C(=O)N(C3CCOCC3)c3ccc([N+](=O)[O-])cc32)C1] | A2 | B9 | $(M + H)^+ = 479$ | 1.47 min (Method A) |

-continued

| No. | Structure Comment | Educt 1 | Educt 2 | Mass signal(s) | R_f value or R_t |
|---|---|---|---|---|---|
| C34 | | A4 | B9 | (M + H)⁺ = 437 | 1.54 min (Method A) |
| C35 | | A2 | B10 | (M + H)⁺ = 330 | 1.16 min (Method L) |
| C36 | | A6 | B10 | (M + H)⁺ = 425 | 1.28 min (Method K) |

Example 9

Synthesis of intermediate C4 and C31

Intermediate C4:

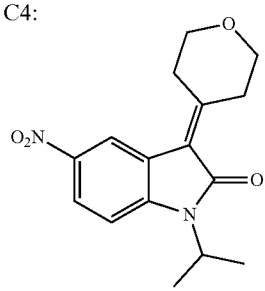

Intermediate A4 (1.50 g; 6.81 mmol) and tetrahydro-4H-pyran-4-one (13.0 mL; 140.76 mmol) in piperidine (1.36 mL; 13.62 mmol) are stirred at 100° C. for 15 min in a microwave. The solvent is evaporated. The residue is stirred in TBME. The precipitate is filtered off and dried.

MS (ESI$^+$): m/z=303 [M+H]$^+$

HPLC (Method A): $R_t$=1.40 min

The following intermediates were prepared in an analogous manner to intermediate C4:

| No. | Structure | Educt 1 Comment | Educt 2 | Mass signal(s) | $R_f$ value or $R_t$ |
|---|---|---|---|---|---|
| C31 | (structure shown) | A2 | Tetrahydro-4H-pyran-4-one | M$^+$ = 344 | 1.32 min (Method A) |

Example 10

Synthesis of Intermediate C9 and C13

Intermediate C9:

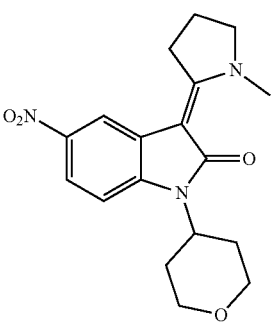 [SMILES: CN1CCC/C1=C1/C(=O)N(C2CCOCC2)c2ccc([N+](=O)[O-])cc21]

The following reaction is performed under a nitrogen atmosphere.

Intermediate A2 (225 mg; 1.24 mmol) and 2,2-dimethoxy-1-methyl-pyrrolidine (450 mg; 3.10 mmol) in chloroform (2.5 mL) are stirred at reflux for 3 h. Additional 2,2-dimethoxy-1-methyl-pyrrolidine (1.2 eq.) is added and the mixture is stirred at 65° C. over night. The mixture is washed with sat. NaHCO$_3$ solution. The organic layer is separated, washed with brine, dried and evaporated. The residue is purified by preparative HPLC (eluent A. water+ 0.15% conc. ammonia, eluent B: MeOH).

MS (ESI$^+$): m/z=344 [M+H]$^+$

HPLC (Method A): $R_t$=1.26 min

The following intermediates were prepared in an analogous manner to intermediate C9:

| No. | Structure | Educt 1 Comment | Educt 2 | Mass signal(s) | $R_f$ value or $R_t$ |
|---|---|---|---|---|---|
| C13 | (structure shown) | A4 | 2,2-dimethoxy-1-methyl-pyrrolidine | (M + H)$^+$ = 302 | 1.34 min (Method A) |

Example 11

Synthesis of Intermediate C15 and C37

Intermediate C15:

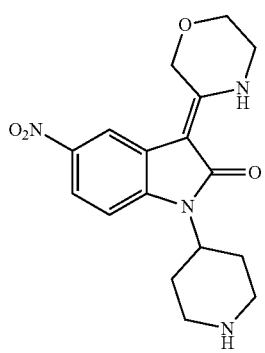 [SMILES: O=C1/C(=C2/COCCN2)c2cc([N+](=O)[O-])ccc2N1C1CCNCC1]

Intermediate C14 (81 mg; 0.16 mmol) in THF (5 mL) and potassium carbonate (51 mg; 0.37 mmol) in water (1.5 mL) are stirred at 40° C. for 2 h. The mixture is diluted with brine and EA. The organic layer is separated, dried and evaporated.

MS (ESI$^+$): m/z=345 [M+H]$^+$

HPLC (Method B): $R_t$=0.9 min

The following intermediates were prepared in an analogous manner to intermediate C15:

| No. | Structure Comment | Educt 1 | Mass signal(s) | $R_f$ value or $R_t$ |
|---|---|---|---|---|
| C37 | 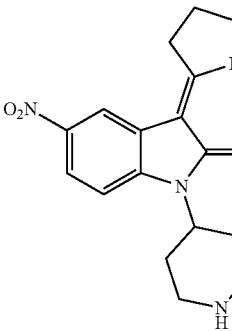<br>The residue is taken up in DCM/water. The precipitate is filtered off and dried. | C36 | (M + H)$^+$ = 329 | 1.07 min (Method N) |

Example 12

Synthesis of Intermediate C17

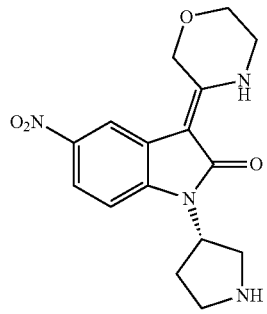 [SMILES: O=C1/C(=C2/COCCN2)c2cc([N+](=O)[O-])ccc2N1[C@H]1CCNC1]

Intermediate C16 (800 mg; 1.86 mmol) in DCM/TFA (1/1; 15 mL) are stirred at room temperature for 1 h. The solvent is evaporated. The residue is taken up in DCM and washed with NaOH (aq. solution; 1M). The organic layer is separated, dried and evaporated.

MS (ESI$^+$): m/z=331 [M+H]$^+$

HPLC (Method B): $R_t$=0.91 min

Example 13

Synthesis of Intermediate C19

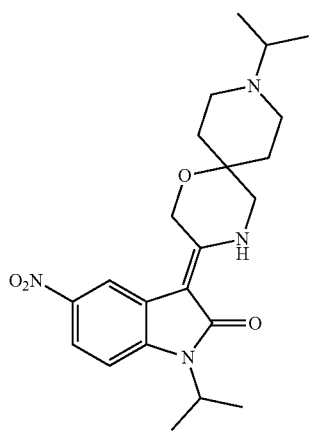 [SMILES: CC(C)N1CCC2(CC1)CN/C(=C1\C(=O)N(C(C)C)c3ccc([N+](=O)[O-])cc31)CO2]

Step 1:

Intermediate C18 (2.70 g; 5.71 mmol) in DCM/TFA (1/1; 30 mL) are stirred at room temperature for 1 h. The solvent is evaporated.

MS (ESI$^+$): m/z=373 [M+H]$^+$

HPLC (Method B): $R_t$=1.15 min

Step 2:

Intermediate C19 Step 1 (600 mg; 1.23 mmol), acetone (448 µL; 6.17 mmol) and glacial acetic acid (182 µL; 3.33 mmol) in MeOH (20 mL) are stirred at room temperature for 1 h. Sodium cyanoborohydride (155 mg; 2.47 mmol) is stirred at room temperature for 2 h. Additional acetone (2 mL) is added. After stirring over night the mixture is diluted with sat. NaHCO$_3$ solution. The organic layer is separated, dried and evaporated.

MS (ESI$^+$): m/z=415 [M+H]$^+$

HPLC (Method B): $R_t$=1.12 min

Example 14

Synthesis of Intermediate C26

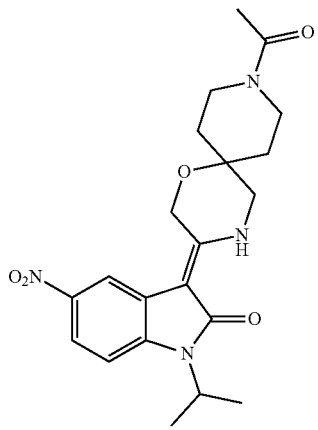 [SMILES: CC(=O)N1CCC2(CC1)CN/C(=C1\C(=O)N(C(C)C)c3ccc([N+](=O)[O-])cc31)CO2]

Step 1:

Intermediate C18 (2.70 g; 5.71 mmol) in DCM/TFA (1/1; 30 mL) are stirred at room temperature for 1 h. The solvent is evaporated.

MS (ESI$^+$): m/z=373 [M+H]$^+$

HPLC (Method B): R$_t$=1.15 min

Step 2:

Intermediate C26 Step 1 (300 mg; 0.62 mmol), acetic anhydride (87 µL; 0.93 mmol) and TEA (316 µL; 1.85 mmol) in DCM (7 mL) are stirred at room temperature for 1 h. The mixture is diluted with sat. NaHCO$_3$ solution and DCM. The organic layer is separated, dried and evaporated.

MS (ESI$^+$): m/z=415 [M+H]$^+$

HPLC (Method B): R$_t$=1.40 min

Example 15

Synthesis of Intermediate C30

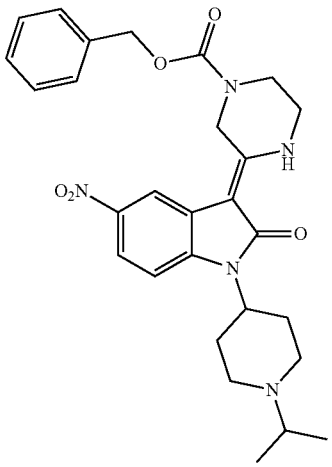 [SMILES: CC(C)N1CCC(N2C(=O)/C(=C3/CN(C(=O)OCc4ccccc4)CCN3)c3cc([N+](=O)[O-])ccc32)CC1]

Step 1:

Intermediate C29 (500 mg; 0.87 mmol) in THF (17 mL) and potassium carbonate (157 mg; 1.13 mmol) in water (12 mL) are stirred at 40° C. for 5 h. The mixture is diluted with NaHCO$_3$ (aq. solution; 9%) and extracted with EA. The organic layer is washed with brine, separated, dried and evaporated. The residue is purified by preparative HPLC (eluent A. water+0.15% conc. ammonia, eluent B: MeOH).

MS (ESI$^+$): m/z=478 [M+H]+

HPLC (Method A): R$_t$=1.46 min

Step 2:

Intermediate C30 Step 1 (118 mg; 0.25 mmol), acetone (90 µL; 1.24 mmol) and glacial acetic acid (36 µL; 0.67 mmol) in MeOH (8 mL) are stirred at room temperature for 2 h. Sodium cyanoborohydride (31 mg; 0.49 mmol) is added and the mixture stirred is stirred at 40° C. for 2 days. The mixture is diluted with NaHCO$_3$ (aq. solution; 9%) and DCM. The organic layer is separated, dried and evaporated. The residue is stirred in MeOH, filtered off and dried. The residue is purified by preparative HPLC (eluent A. water+0.15% conc. ammonia, eluent B: MeOH).

MS (ESI$^+$): m/z=520 [M+H]$^+$

HPLC (Method A): R$_t$=1.58 min

Example 16

Synthesis of Intermediate C38

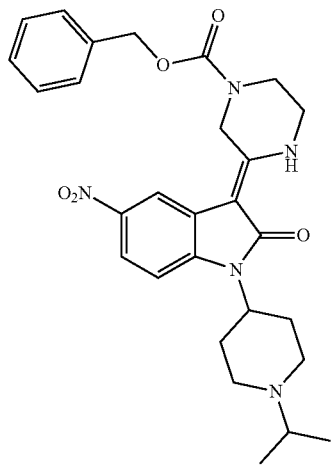 [SMILES: CC(C)N1CCC(N2C(=O)/C(=C3/CN(C(=O)OCc4ccccc4)CCN3)c3cc([N+](=O)[O-])ccc32)CC1]

Intermediate C29 (203 mg; 0.35 mmol) in THF (7 mL) and potassium carbonate (64 mg; 0.46 mmol) in water (5 mL) are stirred at 40° C. for 3 days. The mixture is diluted with NaHCO$_3$ (aq. solution; 9%) and extracted with EA. The organic layer is washed with brine, separated, dried and evaporated. The residue is purified by preparative HPLC (eluent A. water+0.15% conc. ammonia, eluent B: MeOH).

MS (ESI$^+$): m/z=494 [M+H]$^+$

HPLC (Method A): R$_t$=1.38 min

Example 17

Synthesis of intermediates D1-D12, D15-D26, and D28-D31

Intermediate D1:

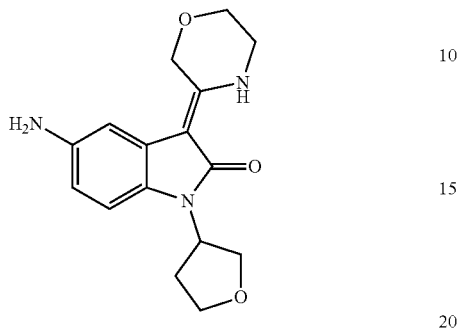

Intermediate C1 (862 mg; 2.60 mmol) and Raney-Nickel (150 mg) in MeOH (25 mL) and THF (50 mL) are hydrogenated in a Parr apparatus (rt; 50 psi; 4.5 h). The catalyst is filtered off and the solvent is evaporated.

MS (ESI$^+$): m/z=302 [M+H]$^+$

HPLC (Method B): R$_t$=0.67 min

The following intermediates were prepared in an analogous manner to intermediate D1:

| No. | Structure | Educt 1 Comment | Mass signal(s) | R$_f$ value or R$_t$ |
|---|---|---|---|---|
| D2 | 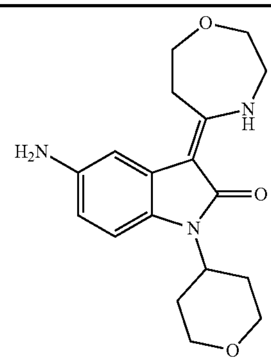 | C2 | (M + H)$^+$ = 330 | 0.73 min (Method B) |
| D3 | 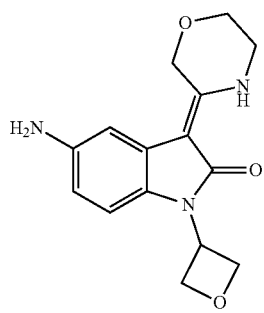 | C3 | (M + H)$^+$ = 288 | 0.89 min (Method A) |

-continued

| No. | Structure Comment | Educt 1 | Mass signal(s) | $R_f$ value or $R_t$ |
|---|---|---|---|---|
| D4 | | C6 | $(M + H)^+ =$ 288 | 0.65 min (Method M) |
| D5 | | C7 | $(M + H)^+ =$ 342 | 0.69 min (Method B) |
| D6 | | C8 | $(M + H)^+ =$ 246 | 0.39 min (Method O) |
| D7 | | C9 | $(M + H)^+ =$ 314 | 0.96 min (Method A) |
| D8 | | C10 | $(M + H)^+ =$ 274 | 0.71 min (Method C) |

-continued

| No. | Structure Comment | Educt 1 | Mass signal(s) | R$_f$ value or R$_t$ |
|---|---|---|---|---|
| D9 | | C11 | (M + H)$^+$ = 332 | 0.95 min (Method A) |
| D10 | | C12 | (M + H)$^+$ = 272 | 1.14 min (Method A) |
| D11 | | C13 | (M + H)$^+$ = 272 | 0.71 min (Method G) |
| D12 | | C15 | (M + H)$^+$ = 315 | |

-continued
| No. | Structure Comment | Educt 1 | Mass signal(s) | $R_f$ value or $R_t$ |
|---|---|---|---|---|
| D15 | 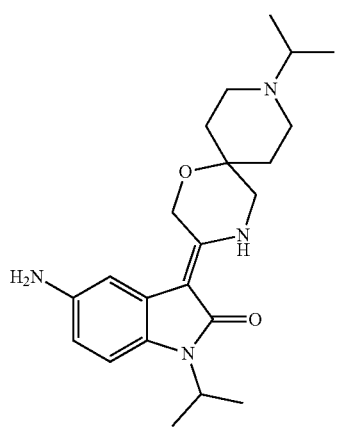 [SMILES: CC(C)N1CCC2(CC1)CN/C(=C1\C(=O)N(C(C)C)c3ccc(N)cc31)CO2] | C19 | $(M + H)^+$ = 385 | 0.71 min (Method B) |
| D16 | 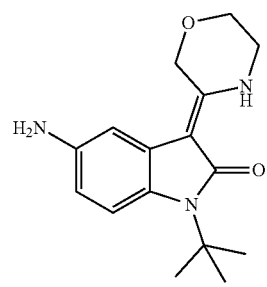 | C20 | $(M + H)^+$ = 288 | 0.91 min (Method G) |
| D17 | 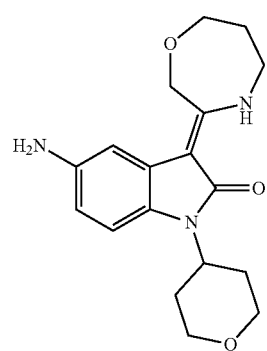 | C21 | $(M + H)^+$ = 330 | 0.76 min (Method B) |

-continued
| No. | Structure Comment | Educt 1 | Mass signal(s) | $R_f$ value or $R_t$ |
|---|---|---|---|---|
| D18 | 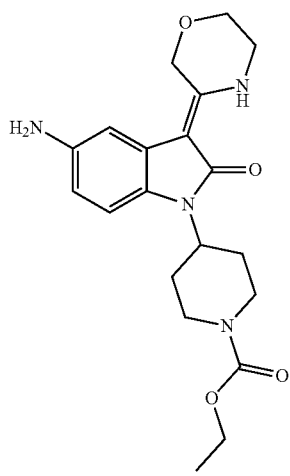 Purification by preparative HPLC ((eluent A. water + 0.1% conc. ammonia, eluent B: MeOH) | C22 | $(M + H)^+$ = 387 | 0.92 min (Method B) |
| D19 | 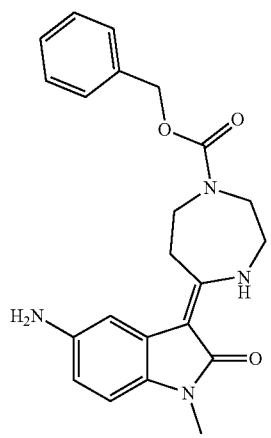 [SMILES: CN1C(=O)/C(=C2/CCN(C(=O)OCc3ccccc3)CCN2)c2cc(N)ccc21] Purification by preparative HPLC (eluent A. water + 0.1% conc. ammonia, eluent B: MeOH) | C23 | $(M + H)^+$ = 393 | 1.15 min (Method H) |
| D20 | 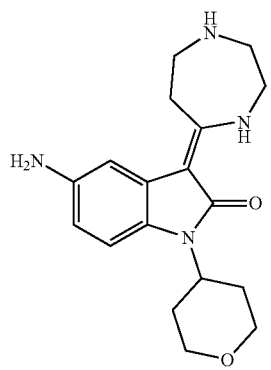 [SMILES: Nc1ccc2c(c1)/C(=C1\CCNCCN1)C(=O)N2C1CCOCC1] | C24 | $(M + H)^+$ = 329 | 1.5 min (Method B) |

-continued

| No. | Structure Comment | Educt 1 | Mass signal(s) | $R_f$ value or $R_t$ |
|---|---|---|---|---|
| D21 | | C25 | (M + H)⁺ = 260 | 0.78 min (Method F) |
| D22 | | C26 | (M + H)⁺ = 385 | 0.84 min (Method B) |
| D23 | | C27 | (M + H)⁺ = 330 | 0.79 min (Method B) |
| D24 | | C17 | (M + H)⁺ = 301 | 0.36 min (Method B) |

-continued

| No. | Structure Comment | Educt 1 | Mass signal(s) | $R_f$ value or $R_t$ |
|---|---|---|---|---|
| D25 | | C28 | (M + H)⁺ = 304 | 0.69 min (Method B) |
| D26 | | C30 | (M + H)⁺ = 356 | 1.14 min (Method A) |
| D28 | | C32 | (M + H)⁺ = 379 | 1.25 min (Method A) |
| D29 | | C33 | (M + H)⁺ = 449 | 1.28 min (Method A) |

-continued
| No. | Structure Comment | Educt 1 | Mass signal(s) | $R_f$ value or $R_t$ |
|---|---|---|---|---|
| D30 | 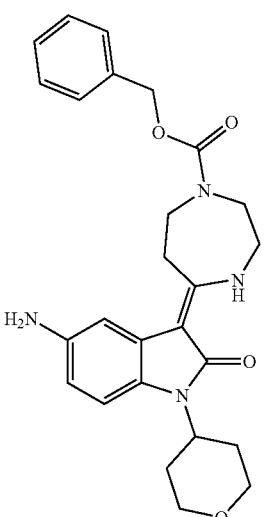 | C24 | $(M + H)^+ =$ 463 | 1.05 min (Method B) |
| D31 | 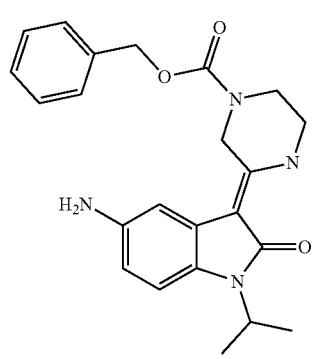 [SMILES: CC(C)N1C(=O)/C(=C2/CN(C(=O)OCc3ccccc3)CCN2)c2cc(N)ccc21] | C34 | $(M + H)^+ =$ 407 | 1.34 min (Method a) |

Example 18

Synthesis of Intermediate D13

Step 1:

Intermediate C17 (270 mg; 0.82 mmol), acetic anhydride (85 µL; 0.90 mmol) and DIPEA (423 µL; 2.46 mmol) in DCM (5 mL) are stirred at room temperature for 15 min. The solvent is evaporated.

MS (ESI$^+$): m/z=373 [M+H]$^+$
HPLC (Method A): R$_t$=1.17 min

Step 2:

Intermediate D13 Step 1 (430 mg; 0.58 mmol) and Raney-Nickel (50 mg) in MeOH (5 mL) and THF (10 mL) are hydrogenated in a Parr apparatus (rt; 50 psi; 17 h). The catalyst is filtered off and the solvent is evaporated. The residue is purified by preparative HPLC (eluent A. water+ 0.1% conc. ammonia, eluent B: MeOH).

MS (ESI$^+$): m/z=343 [M+H]$^+$

Example 19

Synthesis of Intermediate D14

Step 1:

Intermediate C17 (489 mg; 1.48 mmol), oxetan-3-one (160 mg; 2.22 mmol) and glacial acetic acid (218 µL; 4.00 mmol) in MeOH (20 mL) are stirred at room temperature for 1 h. Sodium cyanoborohydride (186 mg; 2.96 mmol) is added and the mixture is stirred at room temperature for 1 h. THF (5 mL) is added. After stirring over night additional sodium cyanoborohydride (186 mg; 2.96 mmol) is added.

The mixture is diluted with water. The organic solvent is evaporated and the aqueous layer is extracted with DCM. The organic layer is separated, dried and evaporated. The residue is stirred in MeOH, filtered off and dried. The residue is purified by preparative HPLC (eluent A. water+ 0.1% conc. ammonia, eluent B: MeOH).

MS (ESI$^+$): m/z=387 [M+H]$^+$
HPLC (Method A): R$_t$=1.24 min

Step 2:

Intermediate D14 Step 1 (164 mg; 0.42 mmol) and Raney-Nickel (50 mg) in MeOH (5 mL) and THF (10 mL) are hydrogenated in a Parr apparatus (rt; 50 psi; 4 h). The catalyst is filtered off and the solvent is evaporated.

MS (ESI$^+$): m/z=357 [M+H]$^+$
HPLC (Method B): R$_t$=0.43 min

Example 20

Synthesis of Intermediate D27

Intermediate C31 (448 mg; 1.30 mmol) and powdered iron (392 mg; 7.02 mmol) in water (14 mL) and ethanol (29 mL) are heated to reflux. Glacial acetic acid (0.79 mL; 13.78 mmol) is added drop wise and the mixture is stirred for 1 h. The organic solvent is evaporated and the residue is taken up in DCM and water. The mixture is alkalised with NaOH (aq. solution; 5 mL). The mixture is filtered through celite. The organic layer is separated, dried and evaporated. The residue is stirred in MeOH/ACN, filtered off and dried.

MS (ESI$^+$): m/z=315 [M+H]$^+$
HPLC (Method A): R$_t$=1.07 min

Example 21

Synthesis of Intermediate E1

Intermediate A10 (11.0 g; 57.24 mmol) and Pd/C (10%; 1.0 g) in DCM (200 mL) are hydrogenated in a Parr apparatus (rt; 50 psi; 5 h). Additional Pd/C (10%; 1.0 g) and MeOH (100 mL) is added and the mixture is hydrogenated for 3 h. Formaldehyde (aq. solution; 37%; 22.70 mL; 304.90 mmol) is added and the mixture is stirred for 10 min without $H_2$-pressure and for further 3 h with $H_2$-pressure. The catalyst is filtered off and the solvent is evaporated. The residue is taken up in NaOH (aq. solution; 1M) and extracted with DCM. The organic layer is separated, dried and evaporated. The residue is purified by MPLC (DCM/MeOH=98/2).

MS (ESI$^+$): m/z=191 [M+H]$^+$
HPLC (Method P): $R_t$=0.25 min

Example 22

Synthesis of Intermediates F1, F2 and F4

Intermediate F1:

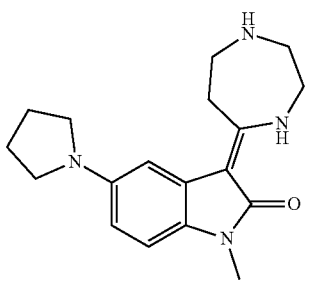 [SMILES: CN1C(=O)/C(=C2/CCNCCN2)c2cc(N3CCCC3)ccc21]

Step 1:

Intermediate D19 (430 mg; 1.10 mmol), 1,4-diiodo-butane (145 µL; 1.10 mmol) and potassium carbonate (303 mg; 2.19 mmol) in DMF (12 mL) are stirred at 70° C. for 2 h. After stirring over night at room temperature the mixture is diluted with NaHCO$_3$ (aq. solution; 9%) and extracted with EA. The organic layer is washed with brine, separated, dried and evaporated. The residue is purified by preparative HPLC (eluent A. water+0.15% conc. ammonia, eluent B: MeOH).

MS (ESI$^+$): m/z=447 [M+H]$^+$
HPLC (Method A): $R_t$=1.57 min

Step 2:

Intermediate F1 Step 1 (203 mg; 0.46 mmol) and Pd/C (10%; 20 mg) in MeOH (20 mL) and THF (10 mL) are hydrogenated in a Parr apparatus (rt; 50 psi; 1 h). Additional Pd/C (10%) is added and the mixture is hydrogenated. The catalyst is filtered off and the solvent is evaporated.

MS (ESI$^+$): m/z=313 [M+H]$^+$
HPLC (Method A): $R_t$=1.33 min

The following intermediates were prepared in an analogous manner to intermediate F1:

| No. | Structure | Educt 1 Comment | Educt 2 | Mass signal(s) | $R_f$ value or $R_t$ |
|---|---|---|---|---|---|
| F2 | 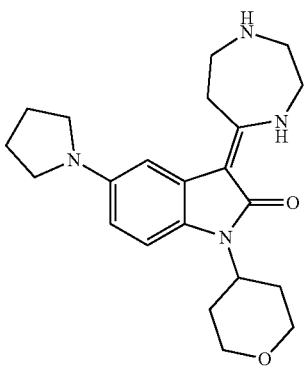 | D28 | 1,4-Diiodo-butane | (M + H)$^+$ = 299 | |
| F4 | 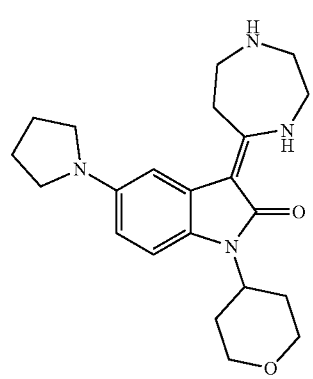 [SMILES: O=C1/C(=C2/CCNCCN2)c2cc(N3CCCC3)ccc2N1C1CCOCC1] | D30 | 1,4-Diiodo-butane | (M + H)$^+$ = 383 | 0.65 min (Method B) |

Example 23

Synthesis of Intermediates F3 and F5

Intermediate F3:

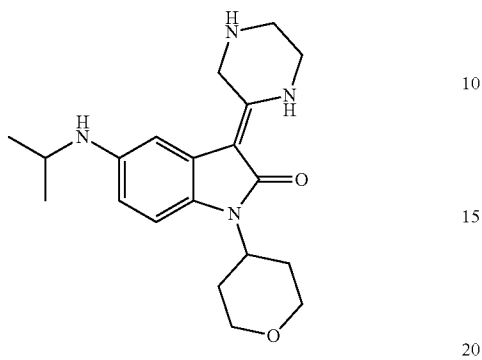

Step 1:

Intermediate D29 (0.78 g; 1.74 mmol), acetone (631 µL; 8.70 mmol) and glacial acetic acid (256 µL; 4.70 mmol) in MeOH (20 mL) are stirred for 2 h at room temperature. Sodium cyanoborohydride (219 mg; 3.48 mmol) is added and the mixture is stirred at room temperature over night. The mixture is diluted with $NaHCO_3$ (aq. solution; 9%) and extracted with DCM. The organic layer is separated, dried and evaporated. The residue is purified by preparative HPLC (eluent A. water+0.15% conc. ammonia, eluent B: MeOH).

MS ($ESI^+$): m/z=491 $[M+H]^+$
HPLC (Method A): $R_t$=1.49 min

Step 2:

Intermediate F3 Step 1 (348 mg; 0.71 mmol) and Pd/C (10%; 35 mg) in MeOH (14 mL) and THF (10 mL) are hydrogenated in a Parr apparatus (rt; 50 psi; 1.25 h). The catalyst is filtered off and the solvent is evaporated. The residue is purified by preparative HPLC (eluent A. water+0.15% conc. ammonia, eluent B: MeOH).

MS ($ESI^+$): m/z=357 $[M+H]^+$
HPLC (Method A): $R_t$=1.19 min

The following intermediate was prepared in an analogous manner to intermediate F3:

| No. | Structure Comment | Educt 1 | Educt 2 | Mass signal(s) | $R_f$ value or $R_t$ |
|---|---|---|---|---|---|
| F5 | | D31 | Acetone | $(M + H)^+$ = 315 | 1.29 min (Method A) |

Example 24

Synthesis of Intermediate G1

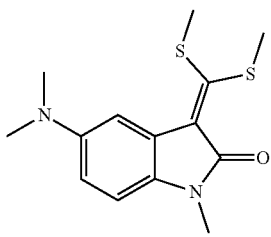

The following reaction is performed under an argon atmosphere.

Intermediate E1 (700 mg; 3.68 mmol) and carbon disulfide (0.24 mL; 4.05 mmol) in DMF (15 mL) are cooled in an ice bath. Sodium hydride (55% in mineral oil; 0.32 g; 7.36 mmol) is added and the mixture is stirred for 20 min. The mixture is allowed to warm up to room temperature. After 1 h of stirring at room temperature the mixture is poured on ice water. The resulting precipitate is filtered off, washed with water and dried.

MS (ESI+): m/z=295 [M+H]+
HPLC (Method H): $R_t$=1.05 min

Example 25

Synthesis of Compounds 1001 to 1123

Compound 1001:

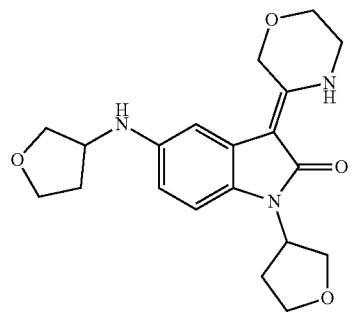 [SMILES: O=C1/C(=C2/COCCN2)c2cc(NC3CCOC3)ccc2N1C1CCOC1]

Intermediate D1 (150 mg; 0.50 mmol), dihydro-furan-3-one (58 µL; 0.75 mmol) and glacial acetic acid (73 µL; 1.34 mmol) in MeOH (3 mL) are stirred for 1 h at room temperature. Sodium cyanoborohydride (63 mg; 1.00 mmol) is added and the mixture is stirred for 1 h at room temperature. The mixture is purified by preparative HPLC (eluent A. water+0.1% conc. ammonia, eluent B: MeOH).

MS (ESI+): m/z=372 [M+H]+
HPLC (Method A): $R_t$=1.11 min

In analogy to the preparation of compound 1001 the following compounds are obtained:

| Nr. | Structure | Educt 1 | Educt 2 | Mass signal(s) | $R_t$ |
|---|---|---|---|---|---|
| 1002 | ![structure] | D1 | ![structure] | (M + H)+ = 374 | 0.98 min (Method A) |
| 1003 | ![structure] | D1 | ![structure] | (M + H)+ = 386 | 1.13 min (Method A) |

-continued

| Nr. | Structure | Educt 1 | Educt 2 | Mass signal(s) | $R_t$ |
|---|---|---|---|---|---|
| 1004 | 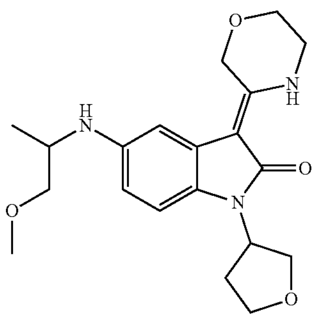 [SMILES: COCC(C)Nc1ccc2c(c1)/C(=C1\COCCN1)C(=O)N2C1CCOC1] | D1 | | $(M + H)^+$ = 374 | 1.21 min (Method A) |
| 1005 | 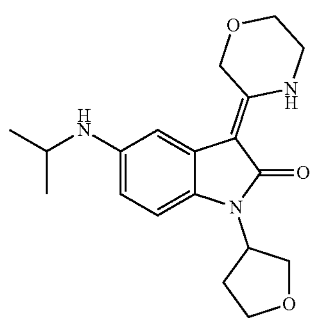 [SMILES: CC(C)Nc1ccc2c(c1)/C(=C1\COCCN1)C(=O)N2C1CCOC1] | D1 | | $(M + H)^+$ = 344 | 0.85 min (Method B) |
| 1006 | 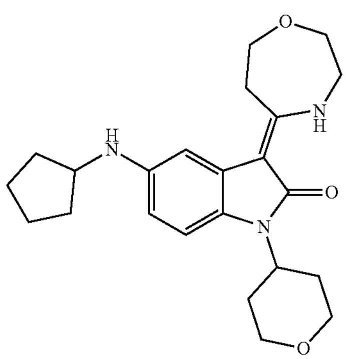 [SMILES: O=C1/C(=C2/CCOCCN2)c2cc(NC3CCCC3)ccc2N1C1CCOCC1] | D2 | | $(M + H)^+$ = 398 | 1.4 min (Method A) |
| 1007 | 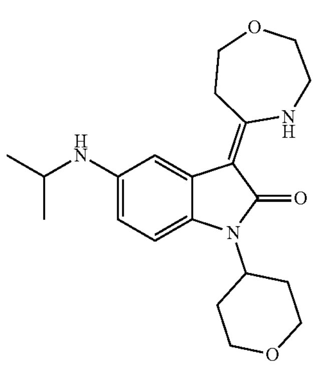 [SMILES: CC(C)Nc1ccc2c(c1)/C(=C1\CCOCCN1)C(=O)N2C1CCOCC1] | D2 | | $(M + H)^+$ = 372 | 0.9 min (Method B) |

| Nr. | Structure | Educt 1 | Educt 2 | Mass signal(s) | R_t |
|---|---|---|---|---|---|
| 1008 | 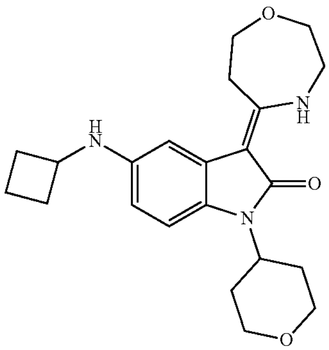 [SMILES: O=C1/C(=C2/CCOCCN2)c2cc(NC3CCC3)ccc2N1C1CCOCC1] | D2 | cyclobutanone | (M + H)+ = 384 | 1.33 min (Method A) |
| 1009 | 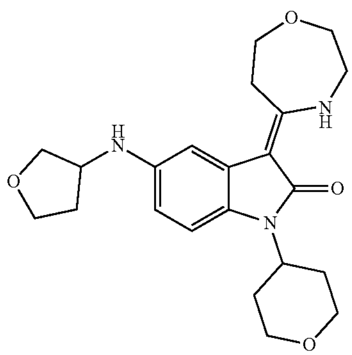 [SMILES: O=C1/C(=C2/CCOCCN2)c2cc(NC3CCOC3)ccc2N1C1CCOCC1] | D2 | dihydrofuran-3(2H)-one | (M + H)+ = 400 | 1.15 min (Method A) |
| 1010 | 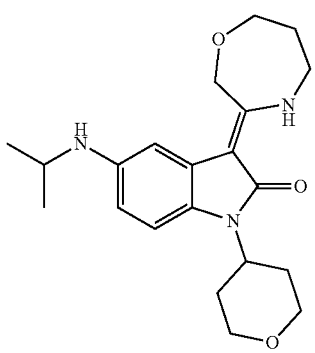 [SMILES: CC(C)Nc1ccc2c(c1)/C(=C1\COCCCN1)C(=O)N2C1CCOCC1] | D17 | acetone | (M + H)+ = 372 | 0.92 min (Method B) |
| 1011 | 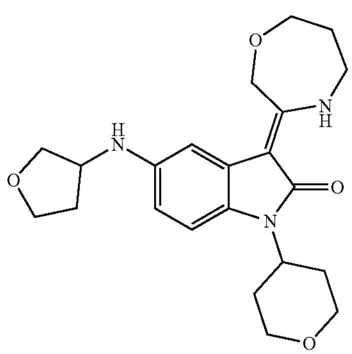 [SMILES: O=C1/C(=C2/COCCCN2)c2cc(NC3CCOC3)ccc2N1C1CCOCC1] | D17 | dihydrofuran-3(2H)-one | (M + H)+ = 400 | 0.85 min (Method B) |

-continued
| Nr. | Structure | Educt 1 | Educt 2 | Mass signal(s) | $R_t$ |
|---|---|---|---|---|---|
| 1012 | 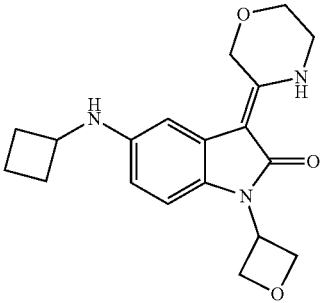 [SMILES: O=C1/C(=C2/COCCN2)c2cc(NC3CCC3)ccc2N1C1COC1] | D3 |  | $(M + H)^+ =$ 342 | 1.27 min (Method A) |
| 1013 | 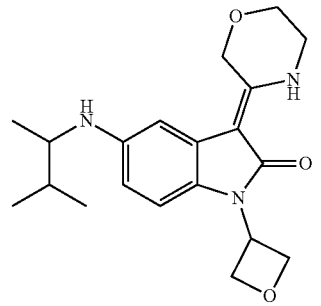 [SMILES: CC(C)C(C)Nc1ccc2c(c1)/C(=C1\COCCN1)C(=O)N2C1COC1] | D3 |  | $(M + H)^+ =$ 358 | 1.41 min (Method A) |
| 1014 | 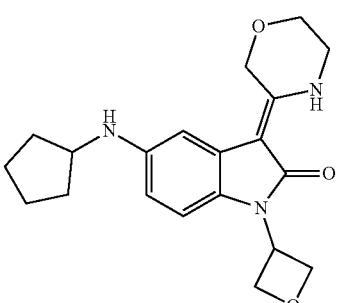 | D3 | 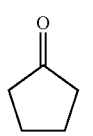 | $(M + H)^+ =$ 356 | 1.35 min (Method A) |
| 1015 | 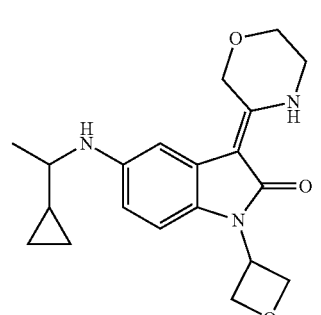 | D3 | 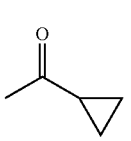 | $(M + H)^+ =$ 356 | 1.33 min (Method A) |
| 1016 | 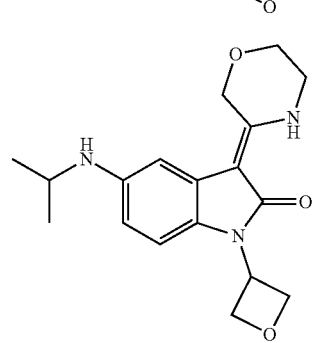 | D3 | 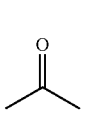 | $(M + H)^+ =$ 330 | 1.22 min (Method A) |

US 11,795,147 B2

159 160

-continued

| Nr. | Structure | Educt 1 | Educt 2 | Mass signal(s) | $R_t$ |
|---|---|---|---|---|---|
| 1017 | 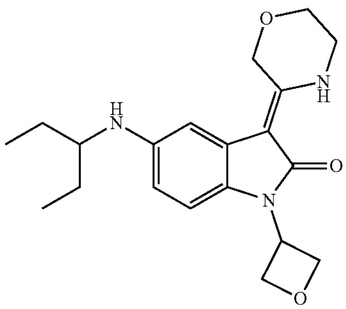 [SMILES: CCC(CC)Nc1ccc2c(c1)/C(=C1\COCCN1)C(=O)N2C1COC1] | D3 | | $(M + H)^+$ = 358 | 1.42 min (Method A) |
| 1018 | 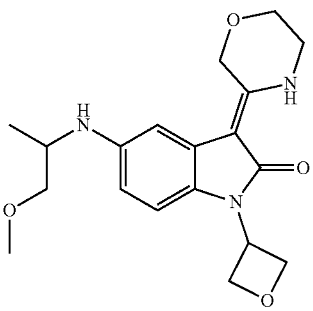 [SMILES: COCC(C)Nc1ccc2c(c1)/C(=C1\COCCN1)C(=O)N2C1COC1] | D3 | | $(M + H)^+$ = 360 | 1.18 min (Method A) |
| 1019 | 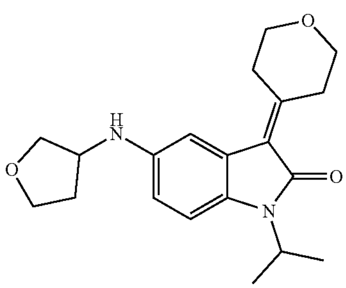 [SMILES: CC(C)N1C(=O)C(=C2CCOCC2)c2cc(NC3CCOC3)ccc21] | Example 176 | | $(M + H)^+$ = 343 | 1.30 min (Method A) |
| 1020 | 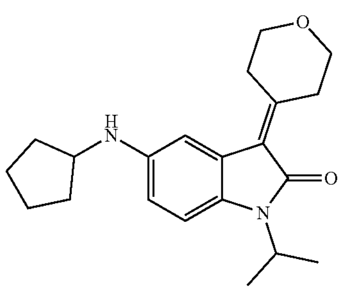 [SMILES: CC(C)N1C(=O)C(=C2CCOCC2)c2cc(NC3CCCC3)ccc21] | Example 176 | | $(M + H)^+$ = 341 | 1.53 min (Method A) |
| 1021 | 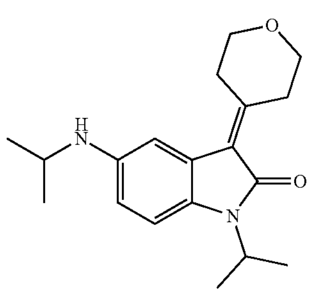 [SMILES: CC(C)Nc1ccc2c(c1)C(=C1CCOCC1)C(=O)N2C(C)C] | Example 176 | | $(M + H)^+$ = 315 | 1.44 min (Method A) |

-continued

| Nr. | Structure | Educt 1 | Educt 2 | Mass signal(s) | $R_t$ |
|---|---|---|---|---|---|
| 1022 | 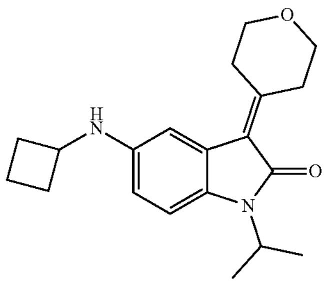 [SMILES: CC(C)N1C(=O)C(=C2CCOCC2)c2cc(NC3CCC3)ccc21] | Example 176 | | $(M + H)^+ =$ 327 | 1.48 min (Method A) |
| 1023 | 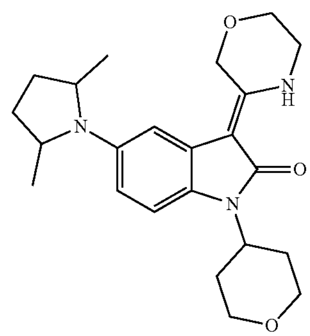 [SMILES: CC1CCC(C)N1c1ccc2c(c1)/C(=C1\COCCN1)C(=O)N2C1CCOCC1] | Example 173 | | $(M + H)^+ =$ 398 | 1.53 min (Method A) |
| 1024 | 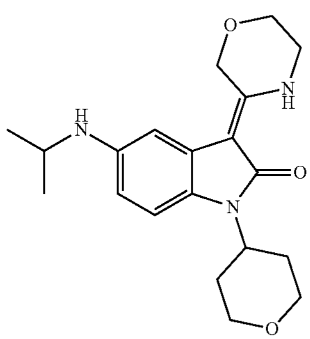 [SMILES: CC(C)Nc1ccc2c(c1)/C(=C1\COCCN1)C(=O)N2C1CCOCC1] | Example 173 | | $(M + H)^+ =$ 358 | 0.83 min (Method C) |
| 1025 | 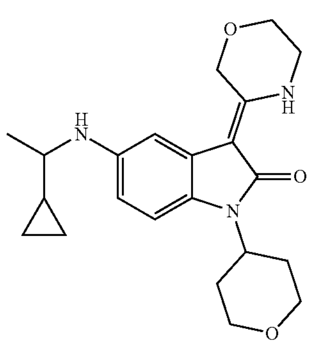 [SMILES: CC(Nc1ccc2c(c1)/C(=C1\COCCN1)C(=O)N2C1CCOCC1)C1CC1] | Example 173 | | $(M + H)^+ =$ 384 | 1.38 min (Method A) |

-continued

| Nr. | Structure | Educt 1 | Educt 2 | Mass signal(s) | $R_t$ |
|---|---|---|---|---|---|
| 1026 | 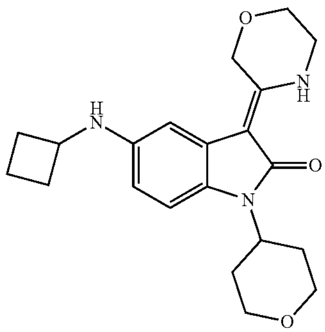 [SMILES: O=C1/C(=C2/COCCN2)c2cc(NC3CCC3)ccc2N1C1CCOCC1] | Example 173 | | (M + H)⁺ = 370 | 1.33 min (Method A) |
| 1027 | 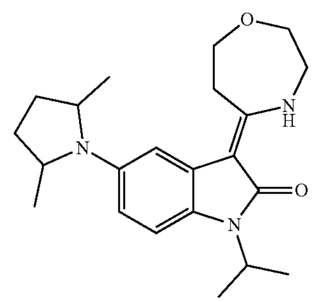 [SMILES: CC(C)N1C(=O)/C(=C2/CCOCCN2)c2cc(N3C(C)CCC3C)ccc21] | D4 | | (M + H)⁺ = 370 | 0.74 min (Method D) |
| 1028 | 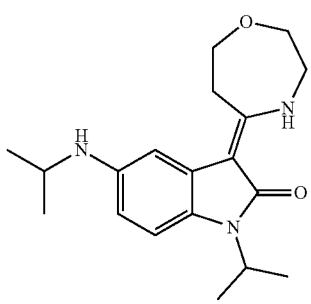 [SMILES: CC(C)Nc1ccc2c(c1)/C(=C1\CCOCCN1)C(=O)N2C(C)C] | D4 | | (M + H)⁺ = 330 | 1.37 min (Method A) |
| 1029 | 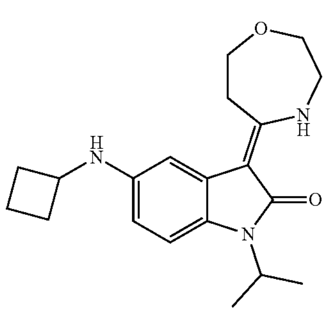 [SMILES: CC(C)N1C(=O)/C(=C2/CCOCCN2)c2cc(NC3CCC3)ccc21] | D4 | | (M + H)⁺ = 342 | 1.42 min (Method A) |

-continued

| Nr. | Structure | Educt 1 | Educt 2 | Mass signal(s) | $R_t$ |
|---|---|---|---|---|---|
| 1030 | 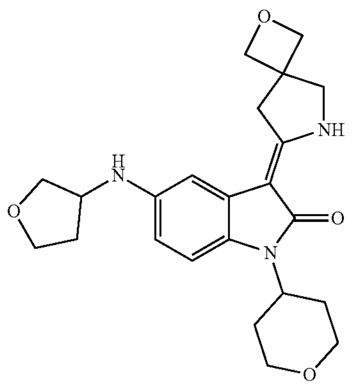 [SMILES: O=C1/C(=C2/CC3(CN2)COC3)c2cc(NC3CCOC3)ccc2N1C1CCOCC1] | D5 | | $(M + H)^+$ = 412 | 0.78 min (Method B) |
| 1031 | 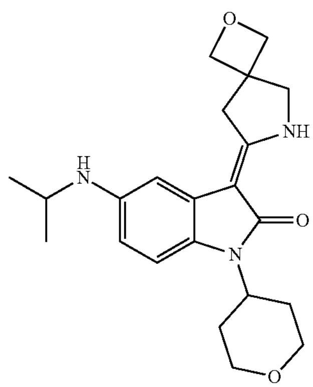 [SMILES: CC(C)Nc1ccc2c(c1)/C(=C1\CC3(CN1)COC3)C(=O)N2C1CCOCC1] | D5 | | $(M + H)^+$ = 384 | 0.84 min (Method B) |
| 1032 | 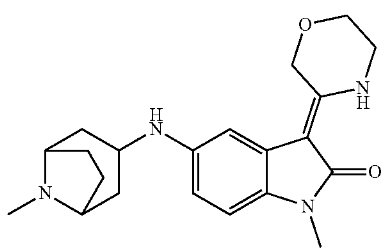 [SMILES: CN1C(=O)/C(=C2/COCCN2)c2cc(NC3CC4CCC(C3)N4C)ccc21] | D6 | | $(M + H)^+$ = 369 | |
| 1033 | 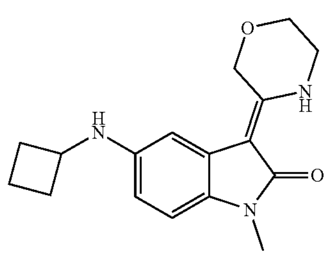 [SMILES: CN1C(=O)/C(=C2/COCCN2)c2cc(NC3CCC3)ccc21] | D6 | | $(M + H)^+$ = 300 | 1.29 min (Method A) |
| 1034 | 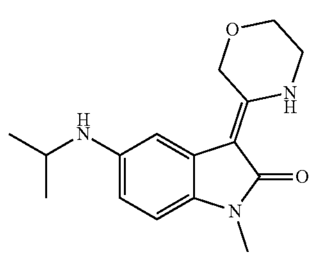 [SMILES: CC(C)Nc1ccc2c(c1)/C(=C1\COCCN1)C(=O)N2C] | D6 | | $(M + H)^+$ = 288 | 1.23 min (Method A) |

-continued

| Nr. | Structure | Educt 1 | Educt 2 | Mass signal(s) | $R_t$ |
|---|---|---|---|---|---|
| 1035 | 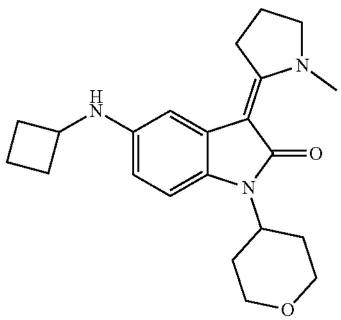 [SMILES: CN1CCC/C1=C1/C(=O)N(C2CCOCC2)c2ccc(NC3CCC3)cc21] | D7 | cyclobutanone | (M + H)⁺ = 368 | 1.31 min (Method A) |
| 1036 | 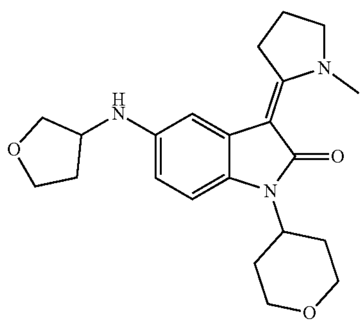 [SMILES: CN1CCC/C1=C1/C(=O)N(C2CCOCC2)c2ccc(NC3CCOC3)cc21] | D7 | dihydrofuran-3(2H)-one | (M + H)⁺ = 384 | 1.12 min (Method A) |
| 1037 | 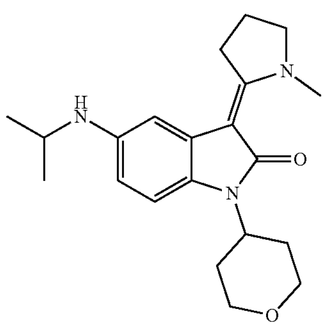 [SMILES: CC(C)Nc1ccc2c(c1)/C(=C1\CCCN1C)C(=O)N2C1CCOCC1] | D7 | acetone | (M + H)⁺ = 356 | 1.26 min (Method A) |
| 1038 | 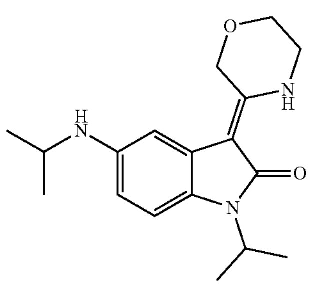 | D8 | acetone | (M + H)⁺ = 316 | 0.9 min (Method C) |
| 1039 | 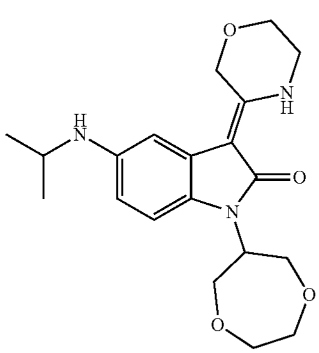 [SMILES: CC(C)Nc1ccc2c(c1)/C(=C1\COCCN1)C(=O)N2C1COCCOC1] | D9 | acetone | (M + H)⁺ = 374 | 1.28 min (Method A) |

-continued

| Nr. | Structure | Educt 1 | Educt 2 | Mass signal(s) | $R_t$ |
|---|---|---|---|---|---|
| 1040 | 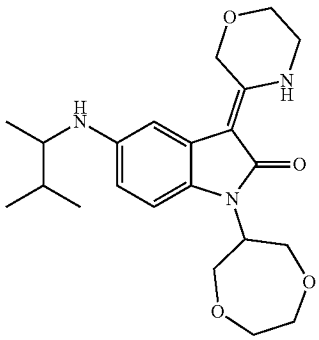 [SMILES: CC(C)C(C)Nc1ccc2c(c1)/C(=C1\COCCN1)C(=O)N2C1COCCOC1] | D9 | | $(M + H)^+$ = 402 | 1.45 min (Method A) |
| 1041 | 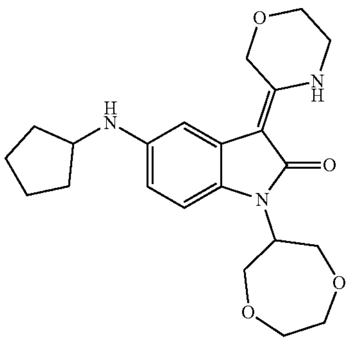 [SMILES: O=C1/C(=C2/COCCN2)c2cc(NC3CCCC3)ccc2N1C1COCCOC1] | D9 | | $(M + H)^+$ = 400 | 1.39 min (Method A) |
| 1042 | 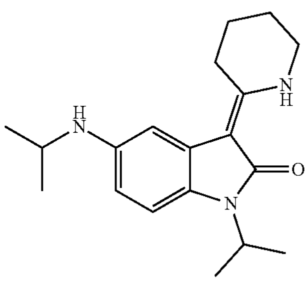 [SMILES: CC(C)Nc1ccc2c(c1)/C(=C1\CCCCN1)C(=O)N2C(C)C] | D10 | | $(M + H)^+$ = 314 | 1.42 min (Method A) |
| 1043 | 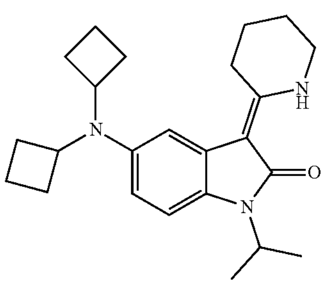 [SMILES: CC(C)N1C(=O)/C(=C2/CCCCN2)c2cc(N(C3CCC3)C3CCC3)ccc21] | D10 | | $(M + H)^+$ = 380 | 1.66 min (Method A) |
| 1044 | 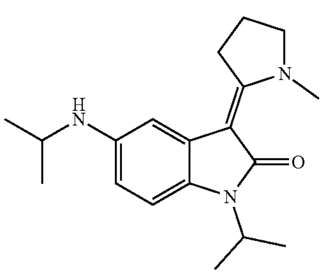 [SMILES: CC(C)Nc1ccc2c(c1)/C(=C1\CCCN1C)C(=O)N2C(C)C] | D11 | | $(M + H)^+$ = 314 | 0.67 min (Method A) |

-continued

| Nr. | Structure | Educt 1 | Educt 2 | Mass signal(s) | R$_t$ |
|---|---|---|---|---|---|
| 1045 | 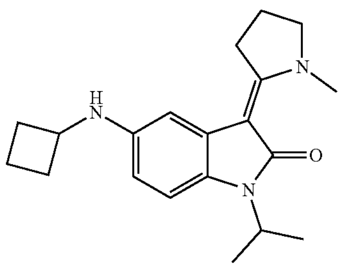 [SMILES: CC(C)N1C(=O)/C(=C2/CCCN2C)c2cc(NC3CCC3)ccc21] | D11 | cyclobutanone | (M + H)$^+$ = 326 | 0.81 min (Method A) |
| 1046 | 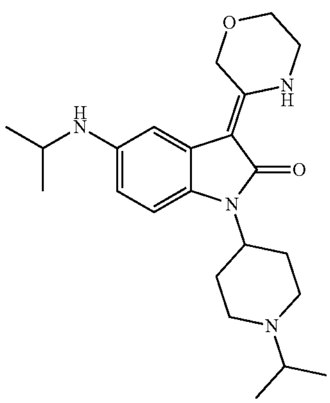 [SMILES: CC(C)Nc1ccc2c(c1)/C(=C1\COCCN1)C(=O)N2C1CCN(C(C)C)CC1] | D12 | acetone | (M + H)$^+$ = 399 | 0.71 min (Method B) |

7 eq. of acetone and 4 eq. of borohydride were used, due to double alkylation

| 1047 | | D12 | acetone | (M + H)$^+$ = 441 | 0.74 min (Method B) |
|---|---|---|---|---|---|

7 eq. of acetone and 4 eq. of borohydride were used, due to triple alkylation

| 1048 | | D13 | acetone | (M + H)$^+$ = 385 | 1.21 min (Method A) |
|---|---|---|---|---|---|

-continued

| Nr. | Structure | Educt 1 | Educt 2 | Mass signal(s) | R$_t$ |
|---|---|---|---|---|---|
| 1049 | 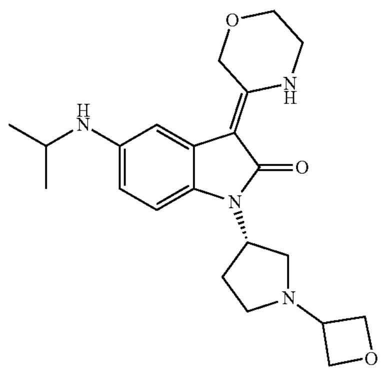 [SMILES: CC(C)Nc1ccc2c(c1)/C(=C1\COCCN1)C(=O)N2[C@H]1CCN(C2COC2)C1] | D14 | acetone | (M + H)$^+$ = 399 | 0.63 min (Method B) |
| 1050 | 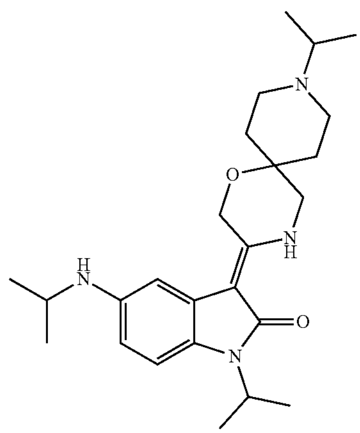 [SMILES: CC(C)Nc1ccc2c(c1)/C(=C1\COC3(CCN(C(C)C)CC3)CN1)C(=O)N2C(C)C] | D15 | acetone | (M + H)$^+$ = 427 | 1.46 min (Method A) |
| 1051 | 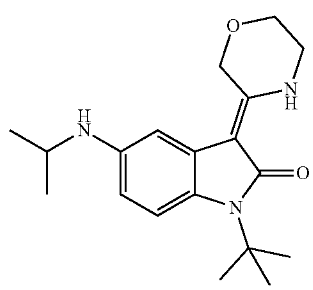 [SMILES: CC(C)Nc1ccc2c(c1)/C(=C1\COCCN1)C(=O)N2C(C)(C)C] | D16 | acetone | (M + H)$^+$ = 330 | 1.45 min (Method A) |
| 1052 | 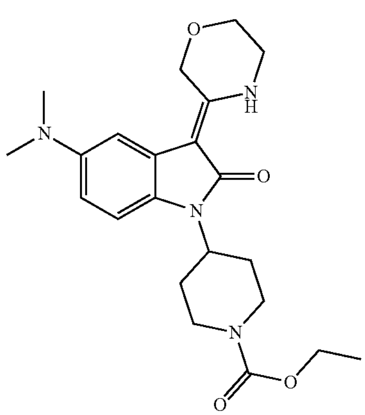 [SMILES: CCOC(=O)N1CCC(N2C(=O)/C(=C3/COCCN3)c3cc(N(C)C)ccc32)CC1] | D18 | formaldehyde | (M + H)$^+$ = 415 | 0.94 min (Method B) |

-continued

| Nr. | Structure | Educt 1 | Educt 2 | Mass signal(s) | R$_t$ |
|---|---|---|---|---|---|
| 1053 | 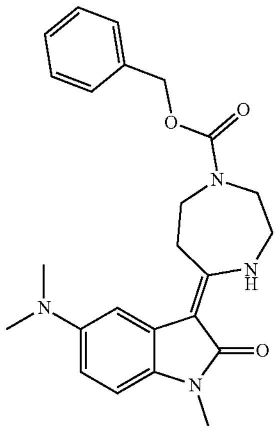 [SMILES: CN(C)c1ccc2c(c1)/C(=C1\CCN(C(=O)OCc3ccccc3)CCN1)C(=O)N2C] | D19 | O | (M + H)$^+$ = 421 | 1.45 min (Method F) |
| 1054 | 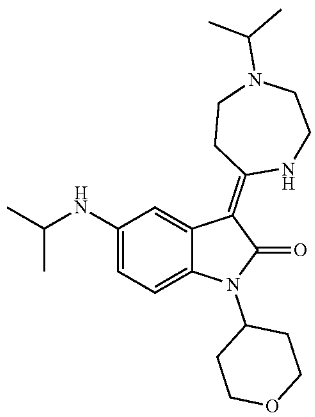 [SMILES: CC(C)Nc1ccc2c(c1)/C(=C1\CCN(C(C)C)CCN1)C(=O)N2C1CCOCC1] | D20 | O | (M + H)$^+$ = 413 | 1.45 min (Method B) |

5 eq. of acetone and 2 eq. of borohydride were used, due to double alkylation

| 1055 | | D21 | O | (M + H)$^+$ = 288 | 0.86 min (Method F) |
|---|---|---|---|---|---|
| 1056 | | D22 | O | (M + H)$^+$ = 427 | 0.97 min (Method B) |

-continued

| Nr. | Structure | Educt 1 | Educt 2 | Mass signal(s) | $R_t$ |
|---|---|---|---|---|---|
| 1057 | 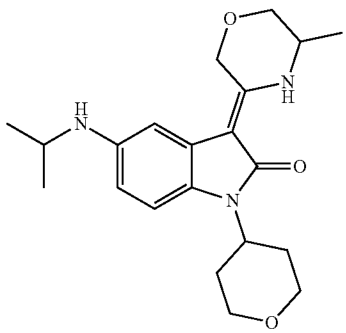 [SMILES: CC(C)Nc1ccc2c(c1)/C(=C1\COCC(C)N1)C(=O)N2C1CCOCC1] | D23 | acetone | $(M + H)^+ =$ 372 | 0.98 min (Method B) |
| 1058 | 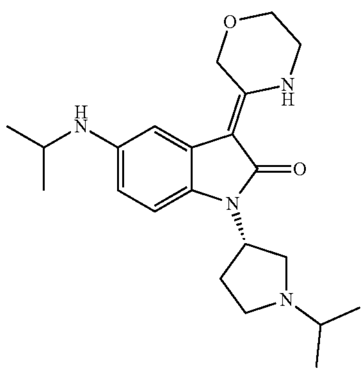 [SMILES: CC(C)Nc1ccc2c(c1)/C(=C1\COCCN1)C(=O)N2[C@H]1CCN(C(C)C)C1] | D24 | acetone | $(M + H)^+ =$ 385 | 0.7 min (Method B) |

5 eq. of acetone and 2 eq. of borohydride were used, due to double alkylation

| Nr. | Structure | Educt 1 | Educt 2 | Mass signal(s) | $R_t$ |
|---|---|---|---|---|---|
| 1059 | | D25 | acetone | $(M + H)^+ =$ 346 | 0.85 min (Method B) |
| 1060 | | D18 | acetone | $(M + H)^+ =$ 429 | 1.01 min (Method B) |

-continued

| Nr. | Structure | Educt 1 | Educt 2 | Mass signal(s) | R_t |
|---|---|---|---|---|---|
| 1061 | 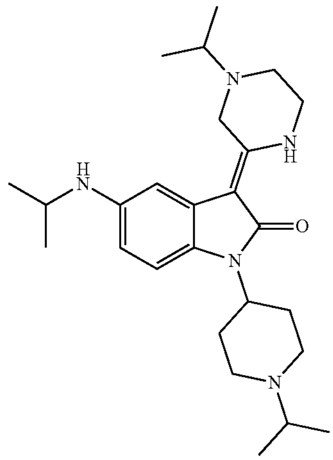 [SMILES: CC(C)Nc1ccc2c(c1)/C(=C1\CN(C(C)C)CCN1)C(=O)N2C1CCN(C(C)C)CC1] | D26 | (acetone) | $(M + H)^+ = 440$ | 1.51 min (Method A) |
| 1062 | 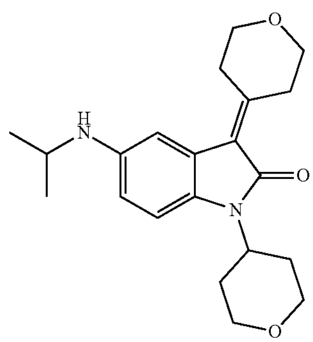 | D27 | (acetone) | $(M + H)^+ = 440$ | 0.97 min (Method G) |
| 1063 | 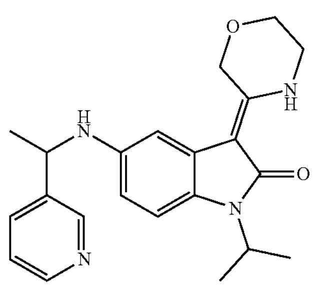 | D8 | (3-acetylpyridine) | $(M + H)^+ = 379$ | 0.29 min (Method E) |
| 1064 | 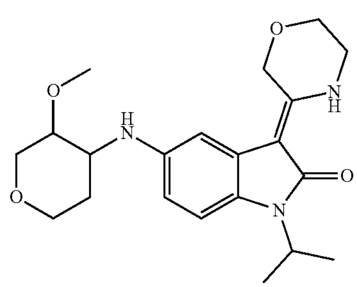 [SMILES: COC1COCCC1Nc1ccc2c(c1)/C(=C1\COCCN1)C(=O)N2C(C)C] | D8 | (3-methoxytetrahydro-4H-pyran-4-one) | $(M + H)^+ = 388$ | 0.30 min (Method E) |

-continued

| Nr. | Structure | Educt 1 | Educt 2 | Mass signal(s) | $R_t$ |
|---|---|---|---|---|---|
| 1065 | 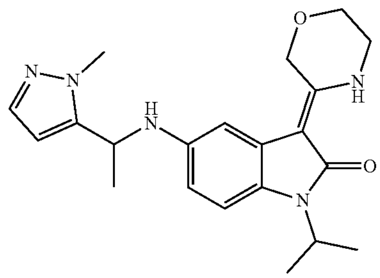 [SMILES: CC(Nc1ccc2c(c1)/C(=C1\COCCN1)C(=O)N2C(C)C)c1ccnn1C] | D8 | | (M + H)⁺ = 381 | 0.30 min (Method E) |
| 1066 | 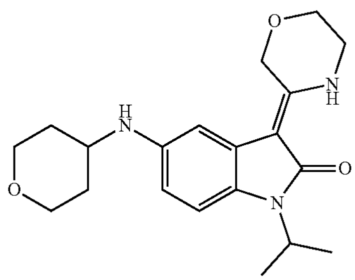 [SMILES: CC(C)N1C(=O)/C(=C2/COCCN2)c2cc(NC3CCOCC3)ccc21] | D8 | | (M + H)⁺ = 358 | 0.30 min (Method E) |
| 1067 | 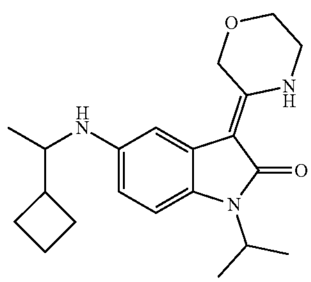 [SMILES: CC(Nc1ccc2c(c1)/C(=C1\COCCN1)C(=O)N2C(C)C)C1CCC1] | D8 | | (M + H)⁺ = 356 | 0.37 min (Method E) |
| 1068 | 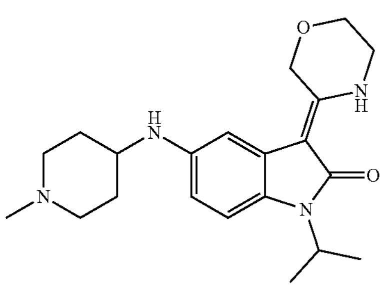 [SMILES: CC(C)N1C(=O)/C(=C2/COCCN2)c2cc(NC3CCN(C)CC3)ccc21] | D8 | | (M + H)⁺ = 371 | 0.24 min (Method E) |
| 1069 | 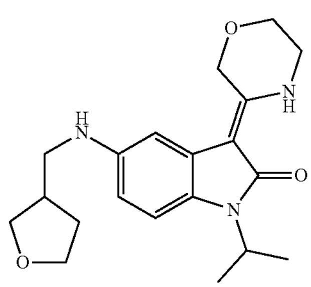 [SMILES: CC(C)N1C(=O)/C(=C2/COCCN2)c2cc(NCC3CCOC3)ccc21] | D8 | | (M + H)⁺ = 358 | 0.30 min (Method E) |

-continued

| Nr. | Structure | Educt 1 | Educt 2 | Mass signal(s) | $R_t$ |
|---|---|---|---|---|---|
| 1070 | 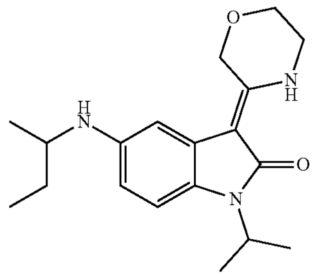 [SMILES: CCC(C)Nc1ccc2c(c1)/C(=C1\COCCN1)C(=O)N2C(C)C] | D8 | | $(M + H)^+$ = 330 | 0.34 min (Method E) |
| 1071 | 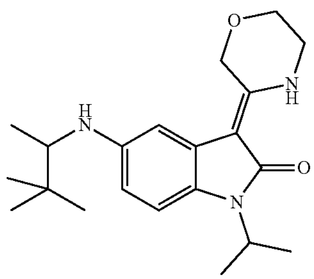 [SMILES: CC(C)N1C(=O)/C(=C2/COCCN2)c2cc(NC(C)C(C)(C)C)ccc21] | D8 | | $(M + H)^+$ = 358 | 0.38 min (Method E) |
| 1072 | 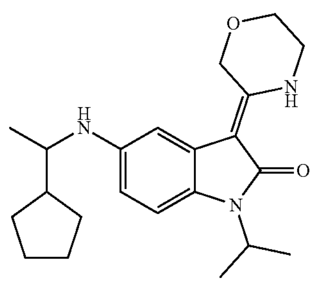 [SMILES: CC(Nc1ccc2c(c1)/C(=C1\COCCN1)C(=O)N2C(C)C)C1CCCC1] | D8 | | $(M + H)^+$ = 370 | 0.39 min (Method E) |
| 1073 | 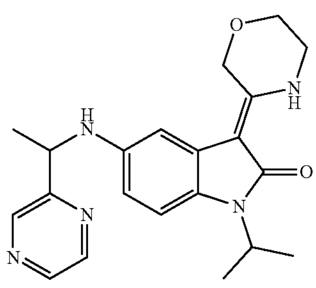 [SMILES: CC(Nc1ccc2c(c1)/C(=C1\COCCN1)C(=O)N2C(C)C)c1cnccn1] | D8 | | $(M + H)^+$ = 380 | 0.31 min (Method E) |
| 1074 | 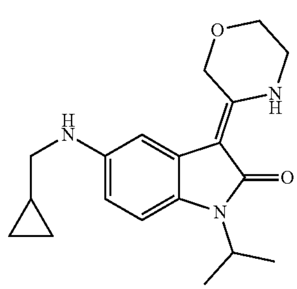 [SMILES: CC(C)N1C(=O)/C(=C2/COCCN2)c2cc(NCC3CC3)ccc21] | D8 | | $(M + H)^+$ = 328 | 0.33 min (Method E) |

-continued
| Nr. | Structure | Educt 1 | Educt 2 | Mass signal(s) | $R_t$ |
|---|---|---|---|---|---|
| 1075 | 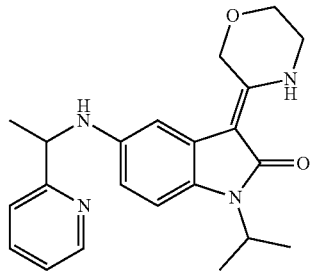 [SMILES: CC(Nc1ccc2c(c1)/C(=C1\COCCN1)C(=O)N2C(C)C)c1ccccn1] | D8 | 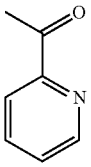 | (M + H)⁺ = 379 | 0.32 min (Method E) |
| 1076 | 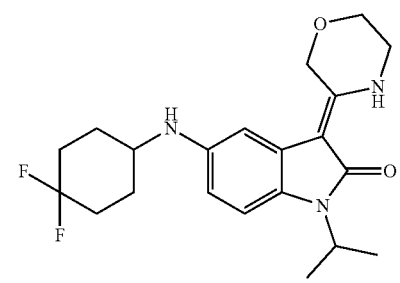 [SMILES: CC(C)N1C(=O)/C(=C2/COCCN2)c2cc(NC3CCC(F)(F)CC3)ccc21] | D8 | 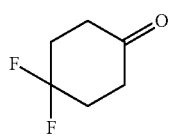 | (M + H)⁺ = 392 | 0.36 min (Method E) |
| 1077 | 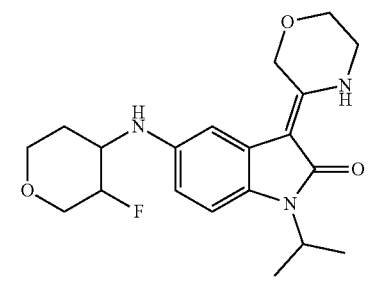 [SMILES: CC(C)N1C(=O)/C(=C2/COCCN2)c2cc(NC3CCOCC3F)ccc21] | D8 | 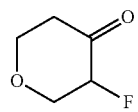 | (M + H)⁺ = 376 | 0.30 min (Method E) |
| 1078 | 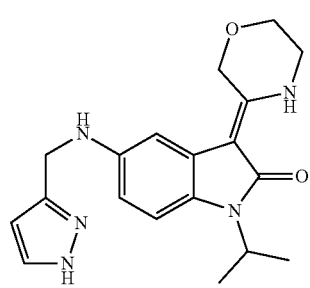 [SMILES: CC(C)N1C(=O)/C(=C2/COCCN2)c2cc(NCc3cc[nH]n3)ccc21] | D8 | 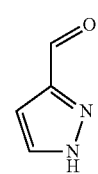 | (M + H)⁺ = 354 | 0.28 min (Method E) |
| 1079 | 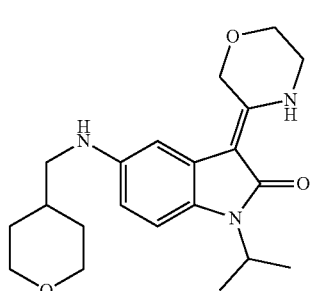 | D8 | 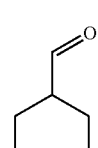 | (M + H)⁺ = 372 | 0.31 min (Method E) |

-continued

| Nr. | Structure | Educt 1 | Educt 2 | Mass signal(s) | $R_t$ |
|---|---|---|---|---|---|
| 1080 | 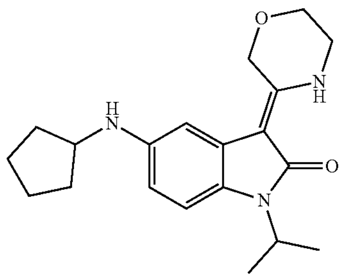 [SMILES: CC(C)N1C(=O)/C(=C2/COCCN2)c2cc(NC3CCCC3)ccc21] | D8 | cyclopentanone | (M + H)⁺ = 342 | 0.35 min (Method E) |
| 1081 | 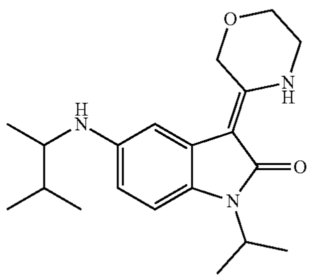 [SMILES: CC(C)C(C)Nc1ccc2c(c1)/C(=C1\COCCN1)C(=O)N2C(C)C] | D8 | 3-methyl-2-butanone | (M + H)⁺ = 344 | 0.36 min (Method E) |
| 1082 | 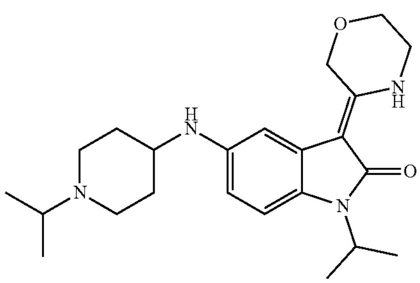 [SMILES: CC(C)N1CCC(Nc2ccc3c(c2)/C(=C2\COCCN2)C(=O)N3C(C)C)CC1] | D8 | 1-isopropylpiperidin-4-one | (M + H)⁺ = 399 | 0.26 min (Method E) |
| 1083 | 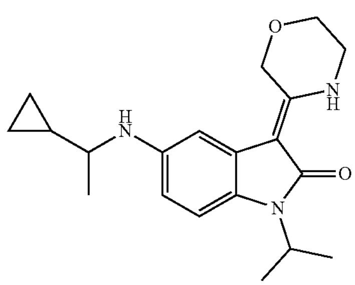 [SMILES: CC(Nc1ccc2c(c1)/C(=C1\COCCN1)C(=O)N2C(C)C)C1CC1] | D8 | cyclopropyl methyl ketone | (M + H)⁺ = 342 | 0.34 min (Method E) |
| 1084 | 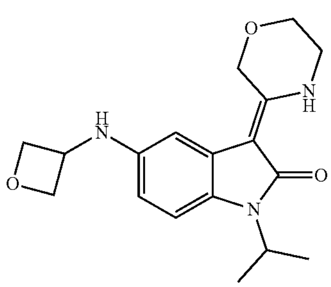 [SMILES: CC(C)N1C(=O)/C(=C2/COCCN2)c2cc(NC3COC3)ccc21] | D8 | oxetan-3-one | (M + H)⁺ = 330 | 0.31 min (Method E) |

| Nr. | Structure | Educt 1 | Educt 2 | Mass signal(s) | R$_t$ |
|---|---|---|---|---|---|
| 1085 | 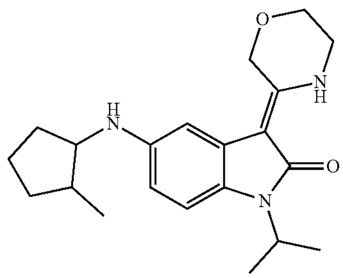 [SMILES: CC1CCCC1Nc1ccc2c(c1)/C(=C1\COCCN1)C(=O)N2C(C)C] | D8 | | (M + H)$^+$ = 356 | 0.34 min (Method E) |
| 1086 | 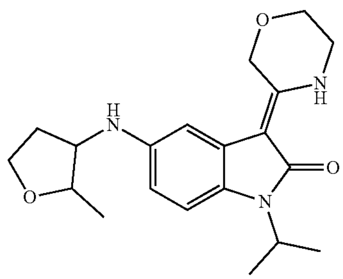 [SMILES: CC1OCCC1Nc1ccc2c(c1)/C(=C1\COCCN1)C(=O)N2C(C)C] | D8 | | (M + H)$^+$ = 358 | 0.31 min (Method E) |
| 1087 | 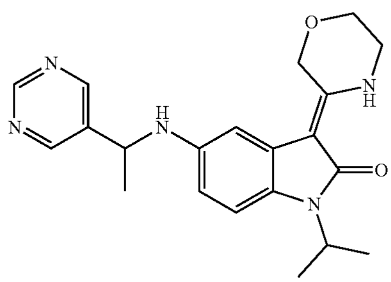 [SMILES: CC(Nc1ccc2c(c1)/C(=C1\COCCN1)C(=O)N2C(C)C)c1cncnc1] | D8 | | (M + H)$^+$ = 380 | 0.30 min (Method E) |
| 1088 | 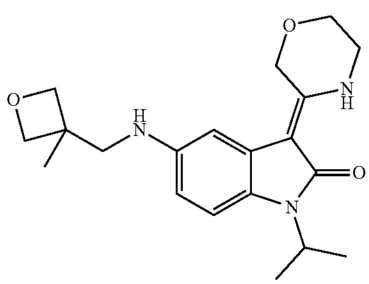 [SMILES: CC(C)N1C(=O)/C(=C2/COCCN2)c2cc(NCC3(C)COC3)ccc21] | D8 | | (M + H)$^+$ = 358 | 0.30 min (Method E) |
| 1089 | 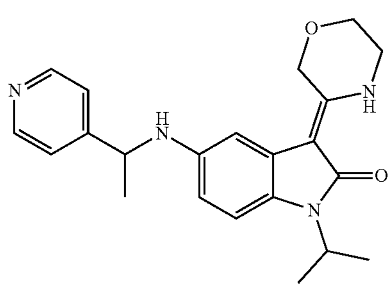 [SMILES: CC(Nc1ccc2c(c1)/C(=C1\COCCN1)C(=O)N2C(C)C)c1ccncc1] | D8 | | (M + H)$^+$ = 379 | 0.30 min (Method E) |

| Nr. | Structure | Educt 1 | Educt 2 | Mass signal(s) | $R_t$ |
|---|---|---|---|---|---|
| 1090 | 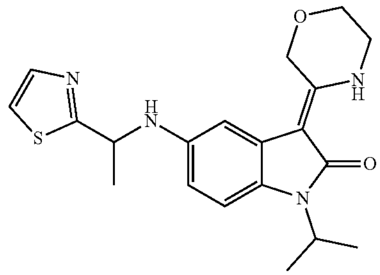 [SMILES: CC(Nc1ccc2c(c1)/C(=C1\COCCN1)C(=O)N2C(C)C)c1nccs1] | D8 | | $(M + H)^+$ = 385 | 0.36 min (Method E) |
| 1091 | 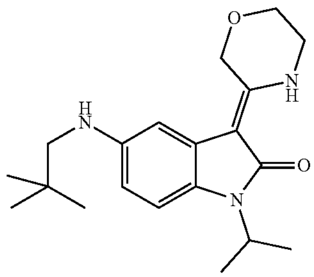 [SMILES: CC(C)N1C(=O)/C(=C2/COCCN2)c2cc(NCC(C)(C)C)ccc21] | D8 | | $(M + H)^+$ = 344 | 0.37 min (Method E) |
| 1092 | 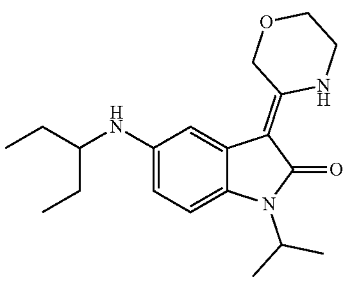 [SMILES: CCC(CC)Nc1ccc2c(c1)/C(=C1\COCCN1)C(=O)N2C(C)C] | D8 | | $(M + H)^+$ = 344 | 0.36 min (Method E) |
| 1093 | 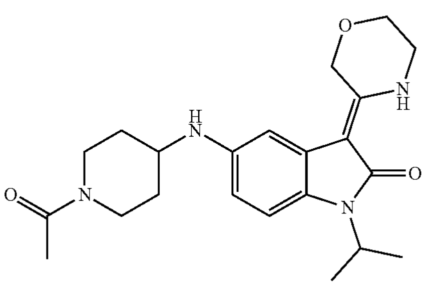 [SMILES: CC(=O)N1CCC(Nc2ccc3c(c2)/C(=C2\COCCN2)C(=O)N3C(C)C)CC1] | D8 | | $(M + H)^+$ = 399 | 0.29 min (Method E) |
| 1094 | 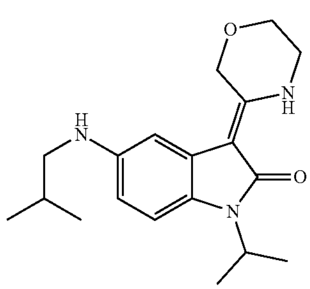 [SMILES: CC(C)CNc1ccc2c(c1)/C(=C1\COCCN1)C(=O)N2C(C)C] | D8 | | $(M + H)^+$ = 330 | 0.35 min (Method E) |

-continued

| Nr. | Structure | Educt 1 | Educt 2 | Mass signal(s) | R$_t$ |
|---|---|---|---|---|---|
| 1095 | 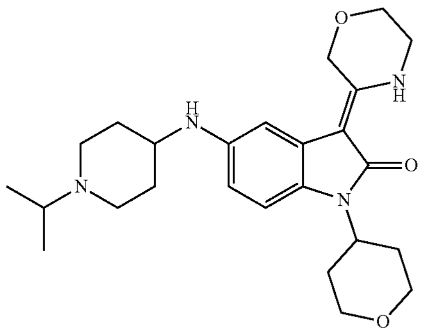 [SMILES: CC(C)N1CCC(Nc2ccc3c(c2)/C(=C2\COCCN2)C(=O)N3C2CCOCC2)CC1] | Example 173 | | (M + H)$^+$ = 441 | 0.24 min (Method E) |
| 1096 | 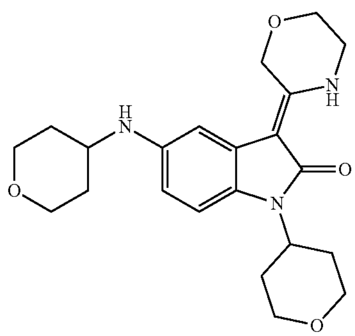 [SMILES: O=C1/C(=C2/COCCN2)c2cc(NC3CCOCC3)ccc2N1C1CCOCC1] | Example 173 | | (M + H)$^+$ = 400 | 0.28 min (Method E) |
| 1097 | 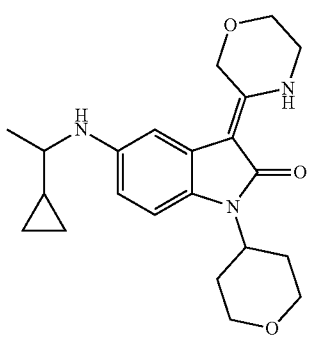 [SMILES: CC(Nc1ccc2c(c1)/C(=C1\COCCN1)C(=O)N2C1CCOCC1)C1CC1] | Example 173 | | (M + H)$^+$ = 384 | 0.32 min (Method E) |
| 1098 | 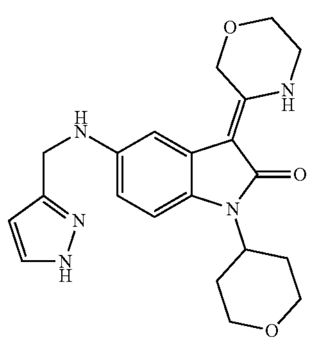 [SMILES: O=C1/C(=C2/COCCN2)c2cc(NCc3cc[nH]n3)ccc2N1C1CCOCC1] | Example 173 | | (M + H)$^+$ = 396 | 0.26 min (Method E) |

-continued

| Nr. | Structure | Educt 1 | Educt 2 | Mass signal(s) | $R_t$ |
|---|---|---|---|---|---|
| 1099 | 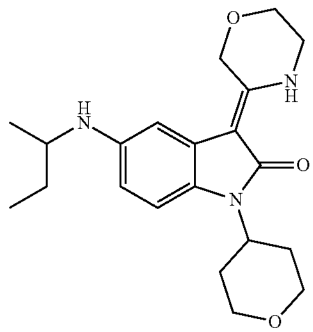 [SMILES: CCC(C)Nc1ccc2c(c1)/C(=C1\COCCN1)C(=O)N2C1CCOCC1] | Example 173 | | $(M + H)^+$ = 372 | 0.31 min (Method E) |
| 1100 | 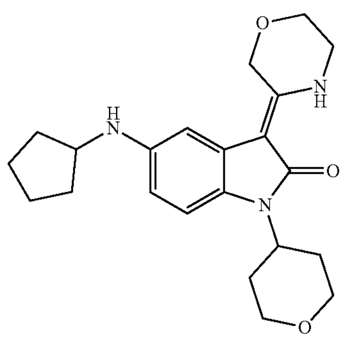 [SMILES: O=C1/C(=C2/COCCN2)c2cc(NC3CCCC3)ccc2N1C1CCOCC1] | Example 173 | | $(M + H)^+$ = 384 | 0.32 min (Method E) |
| 1101 | 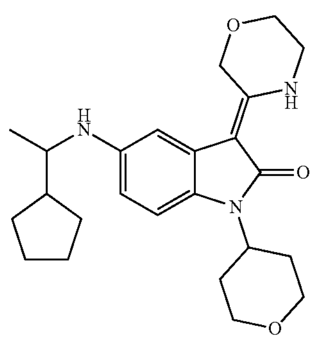 [SMILES: CC(Nc1ccc2c(c1)/C(=C1\COCCN1)C(=O)N2C1CCOCC1)C1CCCC1] | Example 173 | | $(M + H)^+$ = 412 | 0.37 min (Method E) |
| 1102 | 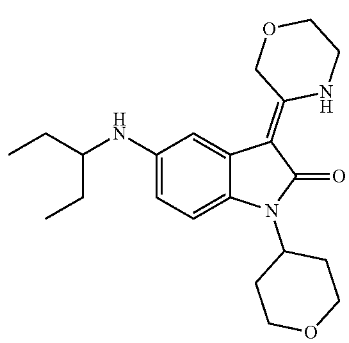 [SMILES: CCC(CC)Nc1ccc2c(c1)/C(=C1\COCCN1)C(=O)N2C1CCOCC1] | Example 173 | | $(M + H)^+$ = 386 | 0.33 min (Method E) |

-continued

| Nr. | Structure | Educt 1 | Educt 2 | Mass signal(s) | $R_t$ |
|---|---|---|---|---|---|
| 1103 | 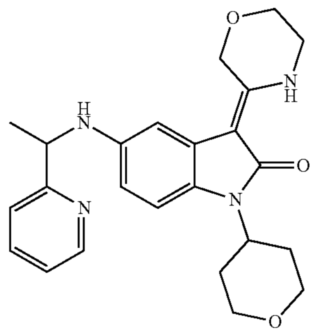 [SMILES: CC(Nc1ccc2c(c1)/C(=C1\COCCN1)C(=O)N2C1CCOCC1)c1ccccn1] | Example 173 | | $(M + H)^+ =$ 421 | 0.29 min (Method E) |
| 1104 | 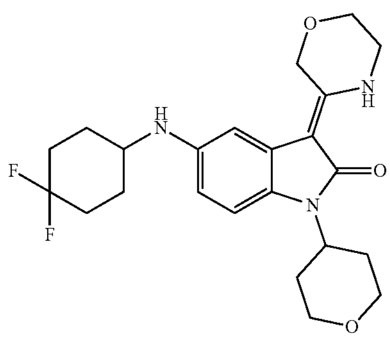 [SMILES: O=C1/C(=C2/COCCN2)c2cc(NC3CCC(F)(F)CC3)ccc2N1C1CCOCC1] | Example 173 | | $(M + H)^+ =$ 434 | 0.34 min (Method E) |
| 1105 | 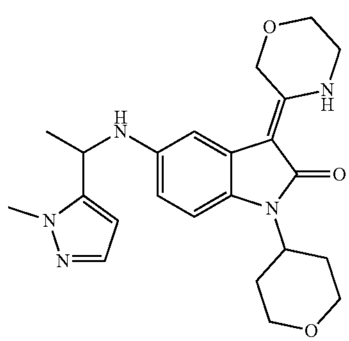 [SMILES: CC(Nc1ccc2c(c1)/C(=C1\COCCN1)C(=O)N2C1CCOCC1)c1ccnn1C] | Example 173 | | $(M + H)^+ =$ 424 | 0.28 min (Method E) |
| 1106 | 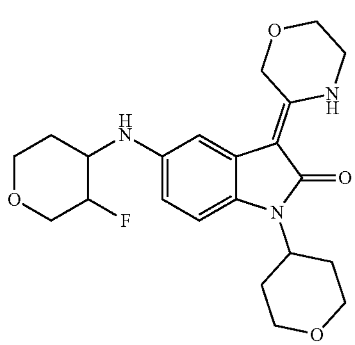 [SMILES: O=C1/C(=C2/COCCN2)c2cc(NC3CCOCC3F)ccc2N1C1CCOCC1] | Example 173 | | $(M + H)^+ =$ 418 | 0.28 min (Method E) |

-continued

| Nr. | Structure | Educt 1 | Educt 2 | Mass signal(s) | $R_t$ |
|---|---|---|---|---|---|
| 1107 | 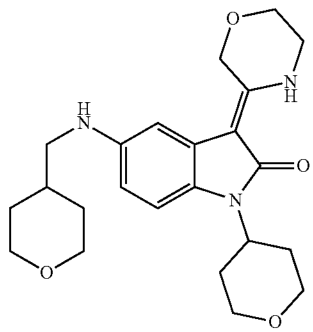 [SMILES: O=C1/C(=C2/COCCN2)c2cc(NCC3CCOCC3)ccc2N1C1CCOCC1] | Example 173 | | $(M + H)^+ =$ 414 | 0.29 min (Method E) |
| 1108 | 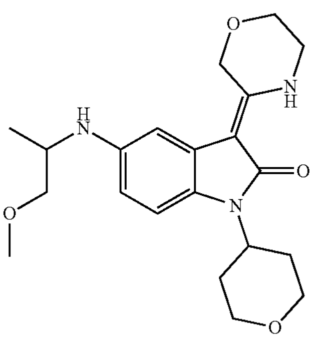 [SMILES: COCC(C)Nc1ccc2c(c1)/C(=C1\COCCN1)C(=O)N2C1CCOCC1] | Example 173 | | $(M + H)^+ =$ 388 | 0.29 min (Method E) |
| 1109 | 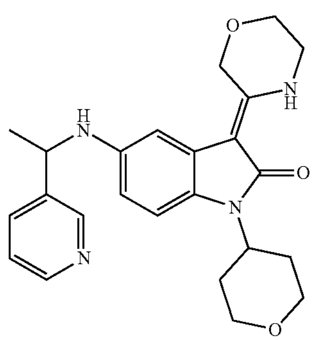 [SMILES: CC(Nc1ccc2c(c1)/C(=C1\COCCN1)C(=O)N2C1CCOCC1)c1cccnc1] | Example 173 | | $(M + H)^+ =$ 421 | 0.27 min (Method E) |
| 1110 | 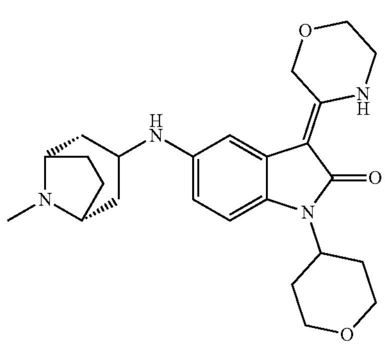 | Example 173 | | $(M + H)^+ =$ 439 | 0.27 min (Method E) |

-continued

| Nr. | Structure | Educt 1 | Educt 2 | Mass signal(s) | $R_t$ |
|---|---|---|---|---|---|
| 1111 | 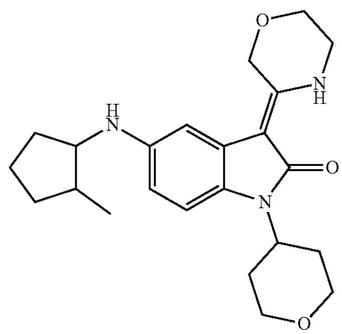 [SMILES: CC1CCCC1Nc1ccc2c(c1)/C(=C1\COCCN1)C(=O)N2C1CCOCC1] | Example 173 | | $(M + H)^+ =$ 398 | 0.34 min (Method E) |
| 1112 | 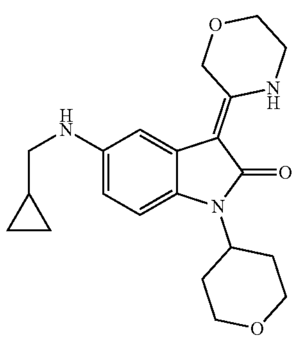 [SMILES: O=C1/C(=C2/COCCN2)c2cc(NCC3CC3)ccc2N1C1CCOCC1] | Example 173 | | $(M + H)^+ =$ 370 | 0.30 min (Method E) |
| 1113 | 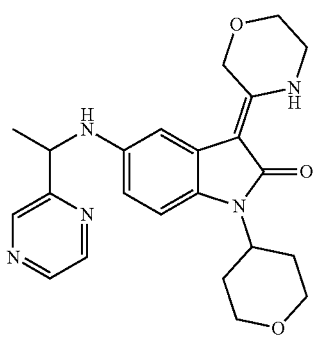 | Example 173 | | $(M + H)^+ =$ 422 | 0.29 min (Method E) |
| 1114 | 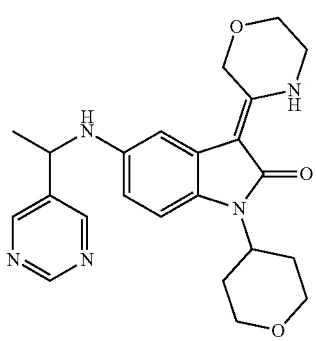 | Example 173 | | $(M + H)^+ =$ 422 | 0.28 min (Method E) |

-continued

| Nr. | Structure | Educt 1 | Educt 2 | Mass signal(s) | $R_t$ |
|---|---|---|---|---|---|
| 1115 | 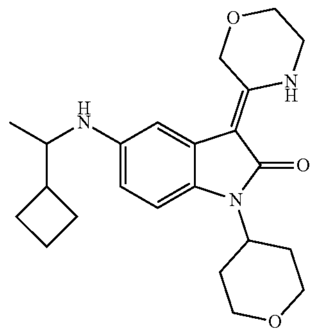 [SMILES: CC(Nc1ccc2c(c1)/C(=C1\COCCN1)C(=O)N2C1CCOCC1)C1CCC1] | Example 173 | | $(M + H)^+$ = 398 | 0.34 min (Method E) |
| 1116 | 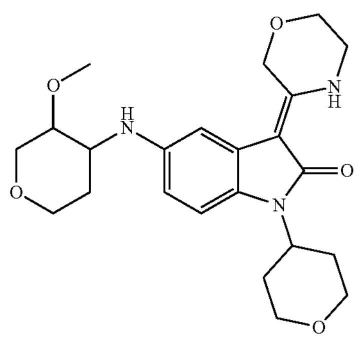 [SMILES: COC1COCCC1Nc1ccc2c(c1)/C(=C1\COCCN1)C(=O)N2C1CCOCC1] | Example 173 | | $(M + H)^+$ = 430 | 0.28 min (Method E) |
| 1117 | 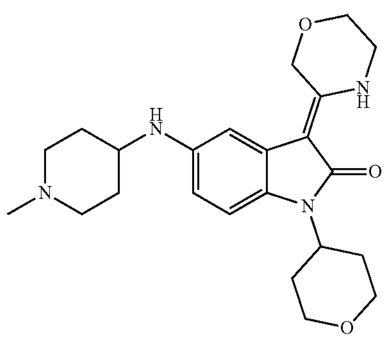 [SMILES: CN1CCC(Nc2ccc3c(c2)/C(=C2\COCCN2)C(=O)N3C2CCOCC2)CC1] | Example 173 | | $(M + H)^+$ = 413 | 0.23 min (Method E) |
| 1118 | 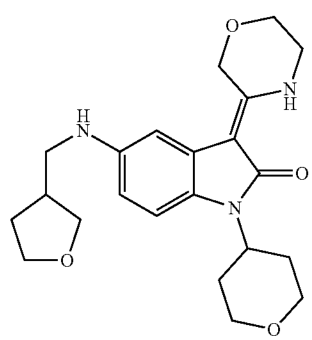 [SMILES: O=C1/C(=C2/COCCN2)c2cc(NCC3CCOC3)ccc2N1C1CCOCC1] | Example 173 | | $(M + H)^+$ = 400 | 0.28 min (Method E) |

-continued

| Nr. | Structure | Educt 1 | Educt 2 | Mass signal(s) | $R_t$ |
|---|---|---|---|---|---|
| 1119 | 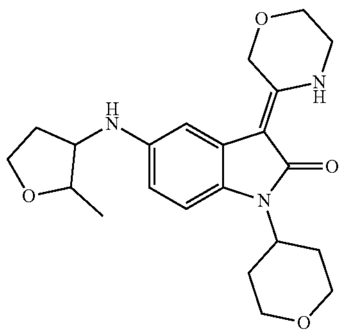 | Example 173 | | $(M + H)^+ = 400$ | 0.29 min (Method E) |
| 1120 | 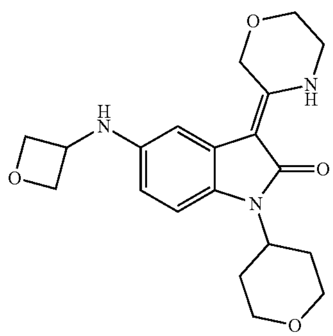 [SMILES: O=C1/C(=C2/COCCN2)c2cc(NC3COC3)ccc2N1C1CCOCC1] | Example 173 | | $(M + H)^+ = 372$ | 0.28 min (Method E) |
| 1121 | 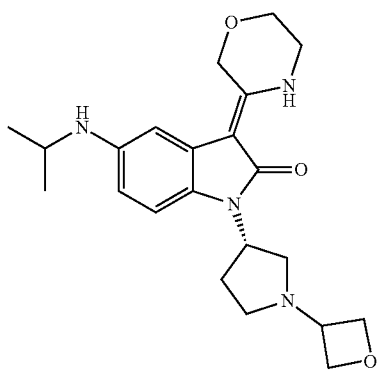 [SMILES: CC(C)Nc1ccc2c(c1)/C(=C1\COCCN1)C(=O)N2[C@H]1CCN(C2COC2)C1] | D14 | | $(M + H)^+ = 399$ | 0.63 min (Method B) |
| 1122 | 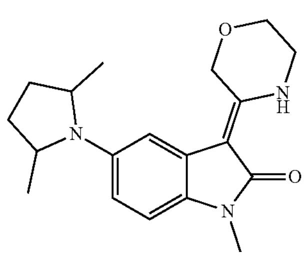 [SMILES: CC1CCC(C)N1c1ccc2c(c1)/C(=C1\COCCN1)C(=O)N2C] | D6 | | $(M + H)^+ = 328$ | 1.52 min (Method A) |
| 1123 | 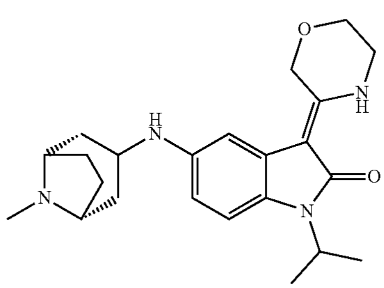 | D8 | | $(M + H)^+ = 397$ | 0.29 min (Method E) |

Example 26

Synthesis of Compounds 1124 to 1147

Compound 1124:

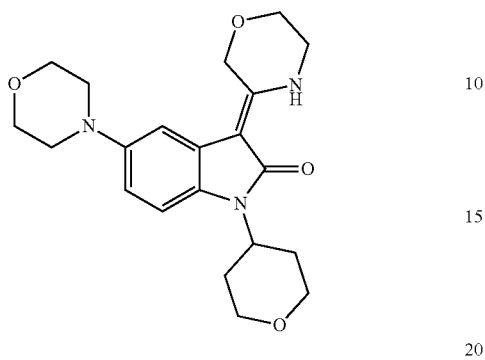

Compound 1173 (70 mg; 0.22 mmol), 2-iodo-2-(-2-iodo-ethoxy)-ethane (32 µL; 0.22 mmol) and potassium carbonate (61 mg; 0.44 mmol) in DMF (3 mL) are stirred for 2 h at 70° C. Additional 2-iodo-2-(2-thoxy)-ethane (0.22 mmol) and potassium carbonate (0.44 mmol) are added. The mixture is stirred at 70° C. for 1.5 h and at room temperature for 3 days. The mixture is diluted with NaHCO$_3$ (aq. solution; 9%) and extracted with EA. The organic layer is washed with brine, separated, dried and evaporated. The residue is purified by preparative HPLC (eluent A: water+0.1% conc. Ammonia, eluent B: MeOH).

MS (ESI$^+$): m/z=386 [M+H]$^+$

HPLC (Method A): R$_t$=1.19 min

In analogy to the preparation of example 1124 the following compounds are obtained:

| Nr. | Structure | Educt 1 | Educt 2 | Mass signal(s) | R$_t$ |
|---|---|---|---|---|---|
| 1125 | 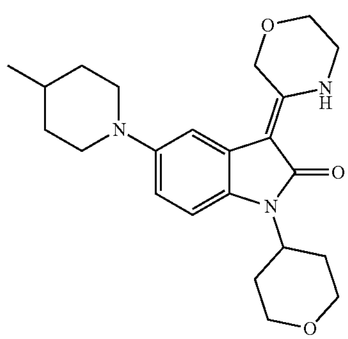 [SMILES: CC1CCN(c2ccc3c(c2)/C(=C2\COCCN2)C(=O)N3C2CCOCC2)CC1] | Example 1173 | Br... Br | (M + H)$^+$ = 398 | 1.51 min (Method A) |
| 1126 | 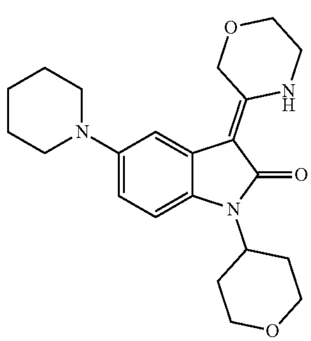 [SMILES: O=C1/C(=C2/COCCN2)c2cc(N3CCCCC3)ccc2N1C1CCOCC1] | Example 1173 | I... I | (M + H)$^+$ = 384 | 1.43 min (Method A) |

-continued

| Nr. | Structure | Educt 1 | Educt 2 | Mass signal(s) | $R_t$ |
|---|---|---|---|---|---|
| 1127 | 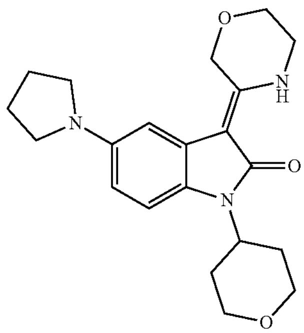 [SMILES: O=C1/C(=C2/COCCN2)c2cc(N3CCCC3)ccc2N1C1CCOCC1] | Example 1173 | I~~~I | $(M + H)^+ = 370$ | 0.83 min (Method G) |
| 1128 | 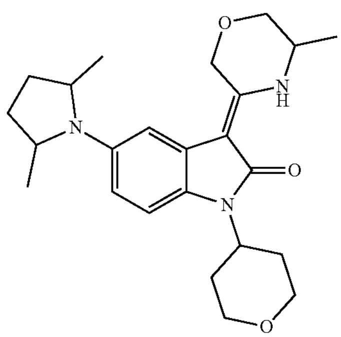 [SMILES: CC1COC/C(=C2/C(=O)N(C3CCOCC3)c3ccc(N4C(C)CCC4C)cc32)N1] | D23 | Br-CH(CH3)CH2CH2CH(CH3)-Br | $(M + H)^+ = 412$ | 1.58 min (Method A) |
| 1129 | 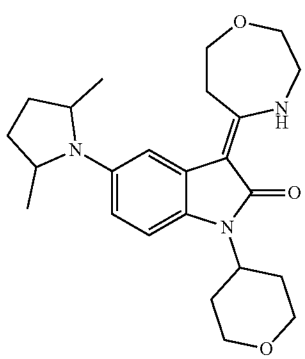 [SMILES: CC1CCC(C)N1c1ccc2c(c1)/C(=C1\CCOCCN1)C(=O)N2C1CCOCC1] | D2 | Br-CH(CH3)CH2CH2CH(CH3)-Br | $(M + H)^+ = 412$ | 0.91 min (Method B) |
| 1130 | 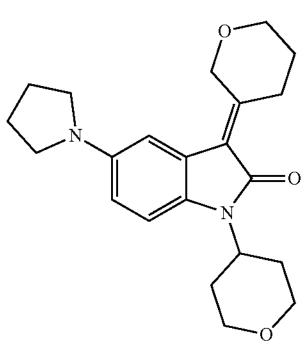 [SMILES: O=C1/C(=C2\CCCOC2)c2cc(N3CCCC3)ccc2N1C1CCOCC1] | D27 | I~~~I | $(M + H)^+ = 369$ | 1.51 min (Method A) |

-continued

| Nr. | Structure | Educt 1 | Educt 2 | Mass signal(s) | R$_t$ |
|---|---|---|---|---|---|
| 1131 | 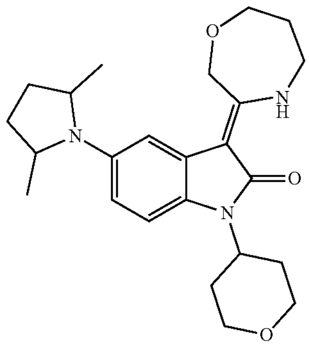 [SMILES: CC1CCC(C)N1c1ccc2c(c1)/C(=C1\COCCCN1)C(=O)N2C1CCOCC1] | D17 | Br-CH(CH₃)-CH₂-CH₂-CH(CH₃)-Br | (M + H)⁺ = 412 | 1.54 min (Method A) |
| 1132 | 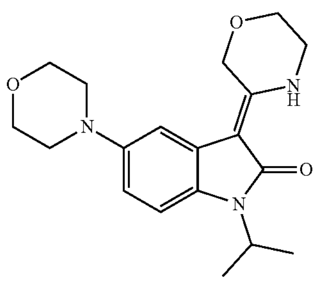 [SMILES: CC(C)N1C(=O)/C(=C2/COCCN2)c2cc(N3CCOCC3)ccc21] | D8 | Br-CH₂CH₂-O-CH₂CH₂-Br | (M + H)⁺ = 342 | 1.29 min (Method A) |
| 1133 | 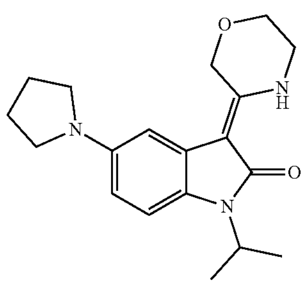 [SMILES: CC(C)N1C(=O)/C(=C2/COCCN2)c2cc(N3CCCC3)ccc21] | D8 | I-(CH₂)₄-I | (M + H)⁺ = 328 | 0.83 min (Method C) |
| 1134 | 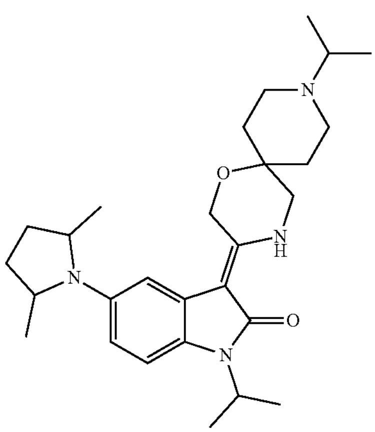 [SMILES: CC(C)N1CCC2(CC1)CN/C(=C1\C(=O)N(C(C)C)c3ccc(N4C(C)CCC4C)cc31)CO2] | D15 | Br-CH(CH₃)-CH₂-CH₂-CH(CH₃)-Br | (M + H)⁺ = 467 | 1.71 min (Method A) |

-continued

| Nr. | Structure | Educt 1 | Educt 2 | Mass signal(s) | R$_t$ |
|---|---|---|---|---|---|
| 1135 | 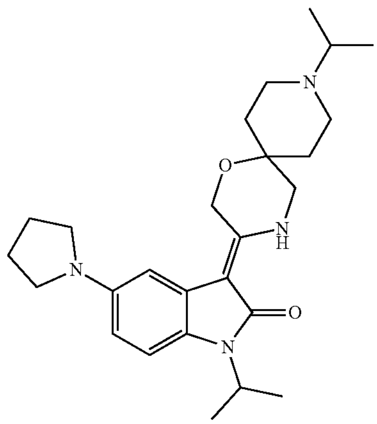 [SMILES: CC(C)N1CCC2(CC1)CN/C(=C1\C(=O)N(C(C)C)c3ccc(N4CCCC4)cc31)CO2] | D15 | I~~~I | (M + H)$^+$ = 439 | 1.67 min (Method A) |
| 1136 | 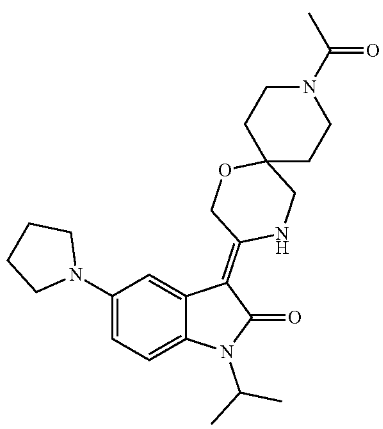 [SMILES: CC(=O)N1CCC2(CC1)CN/C(=C1\C(=O)N(C(C)C)c3ccc(N4CCCC4)cc31)CO2] | D22 | I~~~I | (M + H)$^+$ = 439 | 0.93 min (Method B) |
| 1137 | 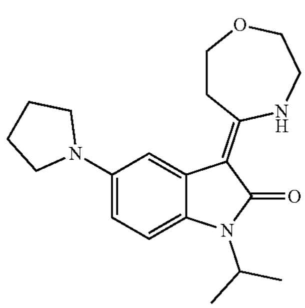 [SMILES: CC(C)N1C(=O)/C(=C2/CCOCCN2)c2cc(N3CCCC3)ccc21] | D4 | I~~~I | (M + H)$^+$ = 342 | 0.72 min (Method D) |
| 1138 | 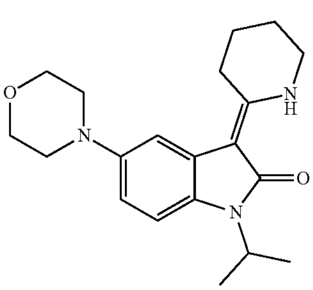 [SMILES: CC(C)N1C(=O)/C(=C2/CCCCN2)c2cc(N3CCOCC3)ccc21] | D10 | I~O~I | (M + H)$^+$ = 342 | 1.36 min (Method A) |

-continued

| Nr. | Structure | Educt 1 | Educt 2 | Mass signal(s) | R$_t$ |
|---|---|---|---|---|---|
| 1139 | 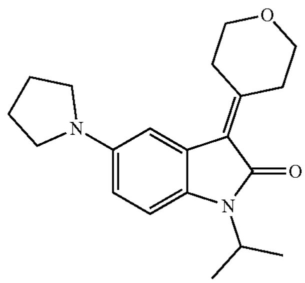 [SMILES: CC(C)N1C(=O)C(=C2CCOCC2)c2cc(N3CCCC3)ccc21] | Example 1177 | I–(CH2)4–I | (M + H)$^+$ = 327 | 1.58 min (Method A) |
| 1140 | 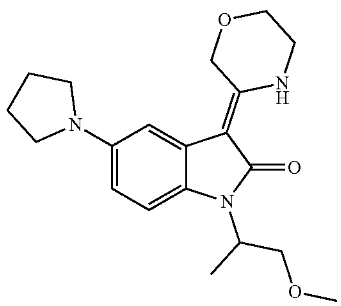 [SMILES: COCC(C)N1C(=O)/C(=C2/COCCN2)c2cc(N3CCCC3)ccc21] | D25 | I–(CH2)4–I | (M + H)$^+$ = 358 | 0.81 min (Method B) |
| 1141 | 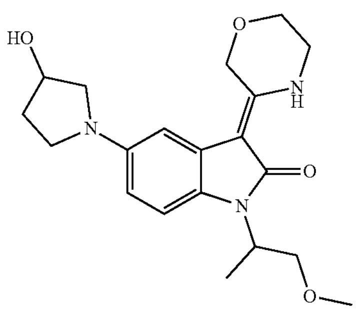 [SMILES: COCC(C)N1C(=O)/C(=C2/COCCN2)c2cc(N3CCC(O)C3)ccc21] | D25 | Br-CH2-CH2-CH(O)-CH2-Br | (M + H)$^+$ = 374 | 0.8 min (Method B) |
| 1142 | 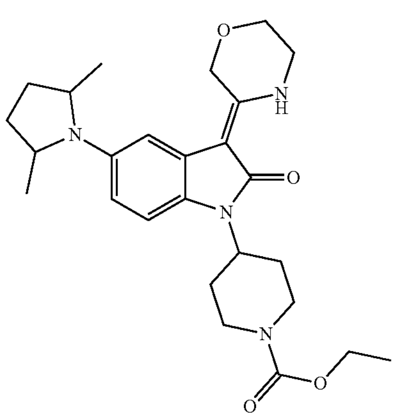 | D18 | Br-CH(CH3)-CH2-CH(CH3)-Br | (M + H)$^+$ = 442 | 1.05 min (Method B) |

US 11,795,147 B2

217                                                                                                                 218

-continued

| Nr. | Structure | Educt 1 | Educt 2 | Mass signal(s) | R$_t$ |
|---|---|---|---|---|---|
| 1143 | 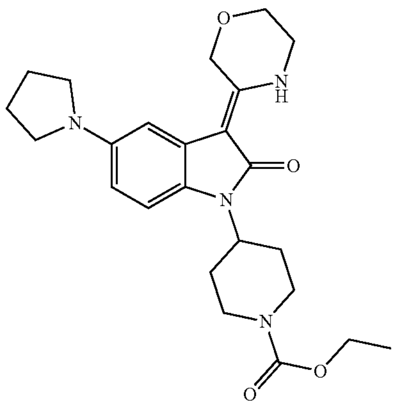 [SMILES: CCOC(=O)N1CCC(N2C(=O)/C(=C3/COCCN3)c3cc(N4CCCC4)ccc32)CC1] | D18 | I-(CH$_2$)$_4$-I | (M + H)$^+$ = 441 | 0.99 min (Method B) |
| 1144 | 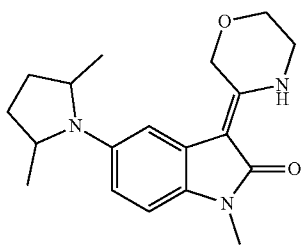 [SMILES: CC1CCC(C)N1c1ccc2c(c1)/C(=C1\COCCN1)C(=O)N2C] | D6 | Br-CH(CH$_3$)-CH$_2$-CH(CH$_3$)-Br | (M + H)$^+$ = 328 | 1.52 min (Method A) |
| 1145 | 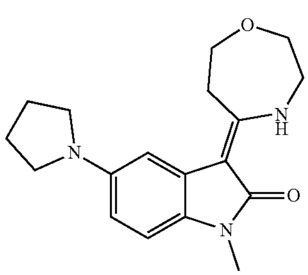 [SMILES: CN1C(=O)/C(=C2/CCOCCN2)c2cc(N3CCCC3)ccc21] | D21 | I-(CH$_2$)$_4$-I | (M + H)$^+$ = 314 | 0.92 min (Method F) |
| 1146 | 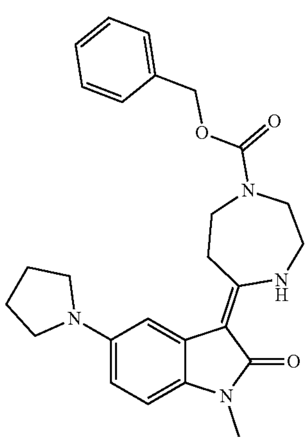 [SMILES: CN1C(=O)/C(=C2/CCN(C(=O)OCc3ccccc3)CCN2)c2cc(N3CCCC3)ccc21] | D19 | I-(CH$_2$)$_4$-I | (M + H)$^+$ = 447 | 1.17 min (Method F) |

| Nr. | Structure | Educt 1 | Educt 2 | Mass signal(s) | $R_t$ |
|---|---|---|---|---|---|
| 1147 | 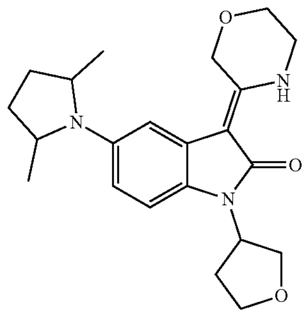 [SMILES: CC1CCC(C)N1c1ccc2c(c1)/C(=C1\COCCN1)C(=O)N2C1CCOC1] | D1 | Br, Br (dibromide) | $(M + H)^+$ = 384 | 0.87 min (Method B) |

Example 27

Synthesis of Compounds 1148 to 1151

Compound 1148:

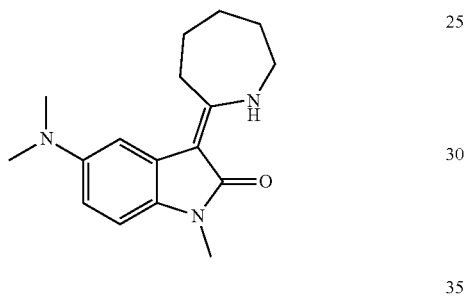

Intermediate E1 (200 mg; 1.05 mmol) and 7-methoxy-3,4,5,6-tetrahydro-2H-azepine (134 mg; 1.05 mmol) are stirred for 20 minutes in a microwave at 170° C. The residue is purified by preparative HPLC (eluent A: water+0.1% conc. Ammonia, eluent B: MeOH).

MS (ESI$^+$): m/z=286 [M+H]$^+$

HPLC (Method H): $R_t$=1.05 min

In analogy to the preparation of example 27 the following compounds are obtained:

| Nr. | Structure | Educt 1 | Educt 2 | Mass signal(s) | $R_t$ |
|---|---|---|---|---|---|
| 1149 | 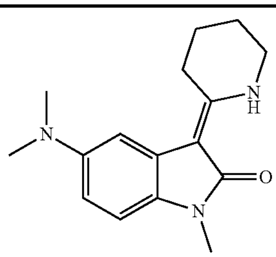 | E1 | | $(M + H)^+$ = 272 | 0.98 min (Method H) |
| 1150 | 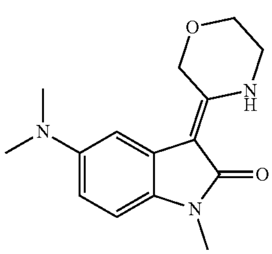 [SMILES: CN(C)c1ccc2c(c1)/C(=C1\COCCN1)C(=O)N2C] | E1 | | $(M + H)^+$ = 274 | 0.43 min (Method I) |

| Nr. | Structure | Educt 1 | Educt 2 | Mass signal(s) | $R_t$ |
|---|---|---|---|---|---|
| 1151 | 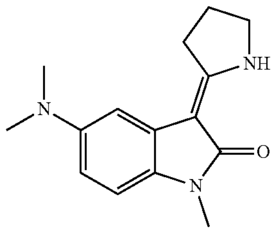 [SMILES: CN(C)c1ccc2c(c1)/C(=C1\CCCN1)C(=O)N2C] | E1 | | $(M + H)^+ = 258$ | 0.89 min (Method H) |

Example 28

Synthesis of Compounds 1152 to 1163

Compound 1152:

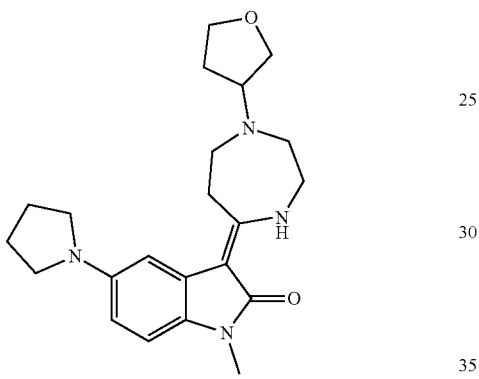

Intermediate F1 (30 mg; 0.10 mmol), 3-(2H)-furanone dihydrochloride (9 μL; 0.12 mmol) and glacial acetic acid (13 μL; 0.24 mmol) in MeOH (2 mL) are stirred at 50° C. for 1 h. Sodium cyanoborohydride (12 mg; 0.19 mmol) is added and stirred at room temperature over night. The mixture is diluted with $NaHCO_3$ (aq. solution; 9%) and extracted with DCM. The organic layer is separated, dried and evaporated. The residue is purified by preparative HPLC (eluent A: water+0.1% conc. Ammonia, eluent B: MeOH).

MS (ESI$^+$): m/z=383 [M+H]$^+$

HPLC (Method A): $R_t$=1.42 min

In analogy to the preparation of example 1152 the following compounds are obtained:

| Nr. | Structure | Educt 1 | Educt 2 | Mass signal(s) | $R_t$ |
|---|---|---|---|---|---|
| 1153 | 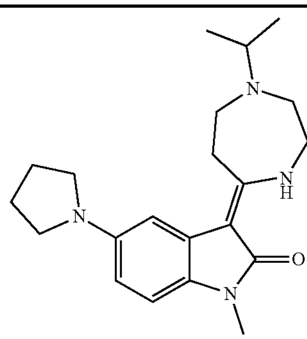 | F1 | | $(M + H)^+ = 355$ | 1.54 min (Method A) |

-continued
| Nr. | Structure | Educt 1 | Educt 2 | Mass signal(s) | $R_t$ |
|---|---|---|---|---|---|
| 1154 | 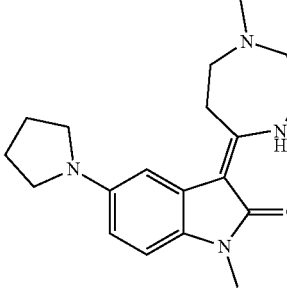 | F1 |  | $(M + H)^+$ = 369 | 1.38 min (Method A) |
| 1155 | 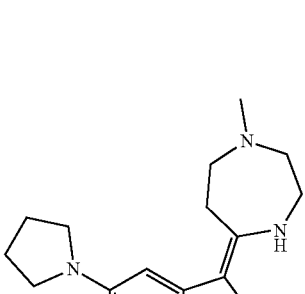 | F1 |  | $(M + H)^+$ = 327 | 1.42 min (Method A) |
| 1156 | 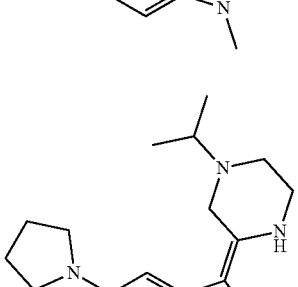 | F2 |  | $(M + H)^+$ = 341 | 1.53 min (Method A) |
| 1157 | 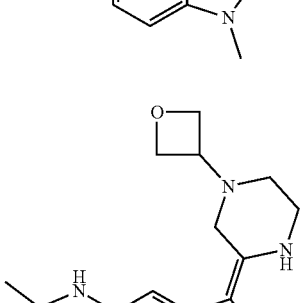 | F3 |  | $(M + H)^+$ = 413 | 1.24 min (Method A) |

-continued

| Nr. | Structure | Educt 1 | Educt 2 | Mass signal(s) | R$_t$ |
|---|---|---|---|---|---|
| 1158 | 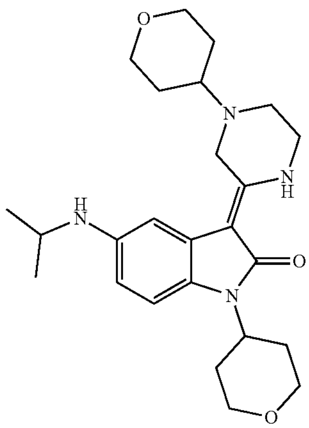 [SMILES: CC(C)Nc1ccc2c(c1)/C(=C1\CN(C3CCOCC3)CCN1)C(=O)N2C1CCOCC1] | F3 | | (M + H)$^+$ = 441 | 1.30 min (Method A) |
| 1159 | 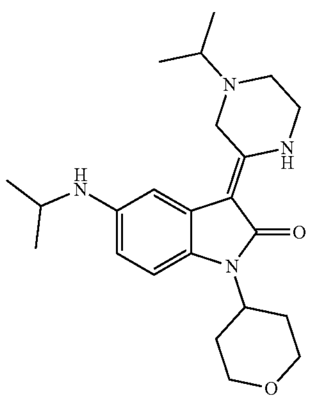 [SMILES: CC(C)Nc1ccc2c(c1)/C(=C1\CN(C(C)C)CCN1)C(=O)N2C1CCOCC1] | F3 | | (M + H)$^+$ = 399 | 1.38 min (Method A) |
| 1160 | 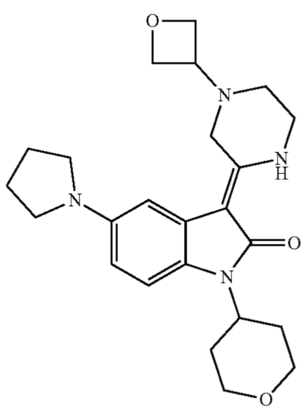 [SMILES: O=C1/C(=C2/CN(C3COC3)CCN2)c2cc(N3CCCC3)ccc2N1C1CCOCC1] | F4 | | (M + H)$^+$ = 439 | 0.67 min (Method A) |
| 1161 | 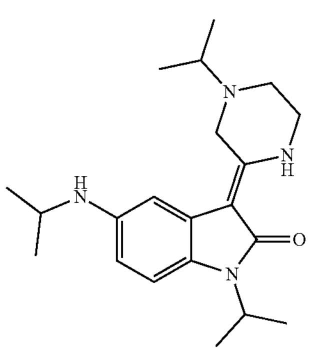 [SMILES: CC(C)Nc1ccc2c(c1)/C(=C1\CN(C(C)C)CCN1)C(=O)N2C(C)C] | F5 | | (M + H)$^+$ = 357 | 1.45 min (Method A) |

-continued

| Nr. | Structure | Educt 1 | Educt 2 | Mass signal(s) | $R_t$ |
|---|---|---|---|---|---|
| 1162 | 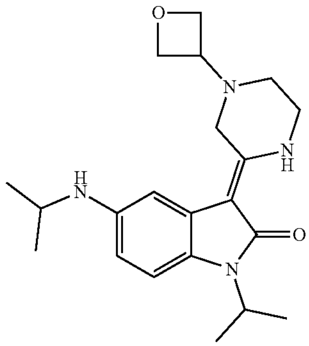 [SMILES: CC(C)Nc1ccc2c(c1)/C(=C1\CN(C3COC3)CCN1)C(=O)N2C(C)C] | F5 | | $(M + H)^+ = 371$ | 1.34 min (Method A) |
| 1163 | 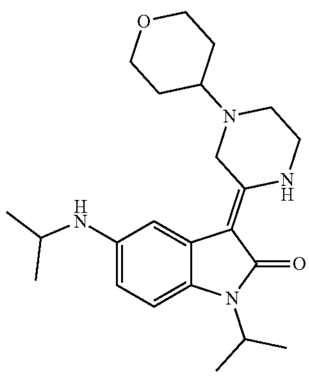 [SMILES: CC(C)Nc1ccc2c(c1)/C(=C1\CN(C3CCOCC3)CCN1)C(=O)N2C(C)C] | F5 | | $(M + H)^+ = 399$ | 1.38 min (Method A) |

Example 29

Synthesis of Compounds 1164

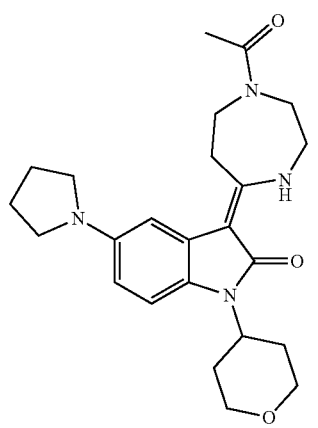 [SMILES: CC(=O)N1CCN/C(=C2\C(=O)N(C3CCOCC3)c3ccc(N4CCCC4)cc32)CC1]

Intermediate F4 (100 mg; 0.26 mmol), acetic anhydride (37 µL; 0.39 mmol) and DIPEA (134 µL; 0.78 mmol) in DCM (3 mL) are stirred at room temperature for 1 h. The mixture is diluted with NaHCO₃ (aq. solution; 9%) and extracted with DCM. The organic layer is separated, dried and evaporated. The residue is taken up in MeOH and the precipitate is filtered off. The precipitate is purified by preparative HPLC (eluent A: water+0.1% conc. ammonia, eluent B: MeOH).

MS (ESI⁺): m/z=425 [M+H]⁺

HPLC (Method B): $R_t$=0.84 min

Example 30

Synthesis of Compound 1165 to 1166

Compound 1165:

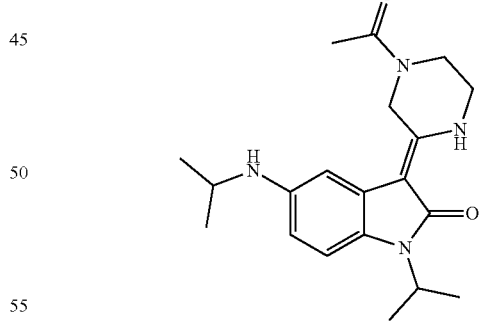

Intermediate F5 (30 mg; 0.10 mmol), acetyl chloride (6 µL; 0.09 mmol) and TEA (20 µL; 0.14 mmol) in THF (3 mL) are stirred at room temperature for 10 minutes. Additional acetyl chloride is added. The mixture is diluted with water and extracted with DCM. The organic layer is separated, dried and evaporated. The residue is purified by preparative HPLC (eluent A: water+0.1% TFA, eluent B: MeOH).

MS (ESI⁺): m/z=357 [M+H]⁺

HPLC (Method D): $R_t$=0.62 min

In analogy to the preparation of compound 1165 the following compound is obtained:

| Nr. | Structure | Educt 1 | Educt 2 | Mass signal(s) | $R_t$ |
|---|---|---|---|---|---|
| 1166 | 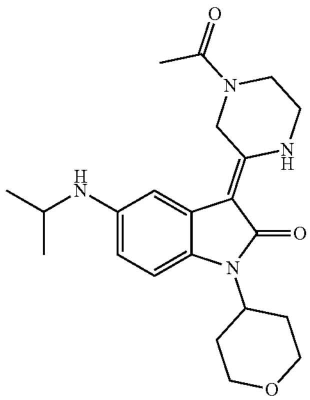 [SMILES: CC(=O)N1CCN/C(=C2\C(=O)N(C3CCOCC3)c3ccc(NC(C)C)cc32)C1] | F3 | | $(M + H)^+ =$ 399 | 0.88 min (Method J) |

Example 31

Synthesis of Compounds 1167 to 1168

Compound 1167:

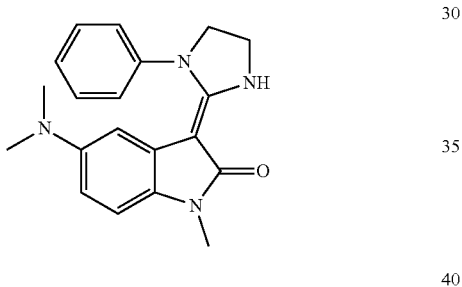

Intermediate G1 (90 mg; 0.31 mmol) and N1-phenyl-ethane-1,2-diamine (42 mg; 0.31 mmol) in n-butanol (2 mL) are stirred for 15 min in a microwave at 220° C. The solvent is evaporated and the residue is purified by preparative HPLC (eluent A: water+0.1% conc. ammonia, eluent B: MeOH).

MS (ESI⁺): m/z=335 [M+H]⁺
HPLC (Method H): $R_t$=1.02 min

In analogy to the preparation of example 1167 the following compounds are obtained:

| Nr. | Structure | Educt 1 | Educt 2 | Mass signal(s) | $R_t$ |
|---|---|---|---|---|---|
| 1168 | 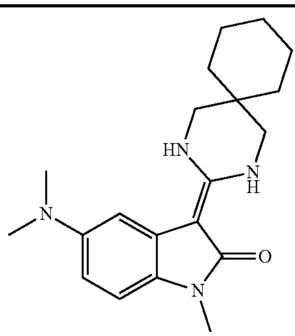 | G1 | | $(M + H)^+ =$ 341 | 1.16 min (Method J) |

Example 32

Synthesis of Compound 1169 to 1171

Compound 1169:

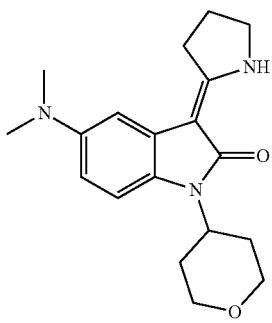 [SMILES: CN(C)c1ccc2c(c1)/C(=C1\CCCN1)C(=O)N2C1CCOCC1]

Intermediate C35 (100 mg; 0.26 mmol), formaldehyde (aq. solution; 37%; 0.19 mL; 2.58 mmol) and Raney-Nickel (50 mg) in MeOH (10 mL) are hydrogenated in a Parr apparatus (rt; 1.1 bar; 8 h). The catalyst is filtered off and the solvent is evaporated. The residue is stirred in MeOH, filtered off and dried.

MS (ESI$^+$): m/z=328 [M+H]+

HPLC (Method ?): $R_t$=0.72 min

In analogy to the preparation of example 1169 the following compounds are obtained:

| Nr. | Structure | Educt 1 | Mass signal(s) | $R_t$ |
|---|---|---|---|---|
| 1170 | 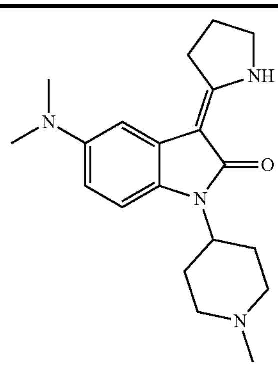 | C37 | (M + H)$^+$ = 341 | 0.75 min (Method K) |
| | 15 eq. of formaldehyde used, due triple alkylation | | | |
| 1171 | 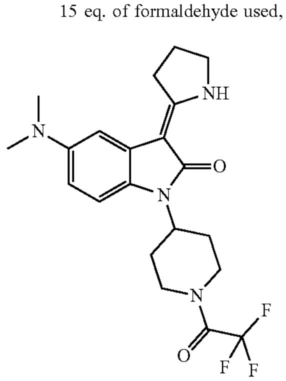 | C36 | (M + H)$^+$ = 423 | 1.06 min (Method K) |

Example 33

Synthesis of Compound 1172 to 1174

Compound 1172:

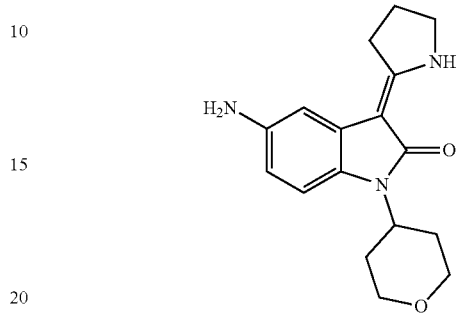

Intermediate C35 (200 mg; 0.52 mmol) and Raney-Nickel (50 mg) in MeOH (10 mL) are hydrogenated in a Parr apparatus (rt; 1.1 bar; 8 h). The catalyst is filtered off and the solvent is evaporated. The residue is purified by preparative HPLC (eluent A: water+0.1% conc. ammonia, eluent B: MeOH).

MS (ESI$^+$): m/z=300 [M+H]$^+$

HPLC (Method L): $R_t$=0.63 min

In analogy to the preparation of example 1172 the following compounds are obtained:

| Nr. | Structure | Educt 1 | Mass signal(s) | $R_t$ |
|---|---|---|---|---|
| 1173 | 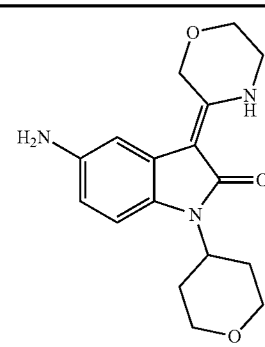 | C5 | (M + H)$^+$ = 316 | 0.69 min (Method B) |
| 1174 | 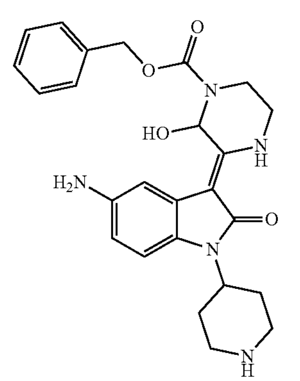 [SMILES: Nc1ccc2c(c1)/C(=C1/NCCN(C(=O)OCc3ccccc3)C1O)C(=O)N2C1CCNCC1] | C38 | (M + H)$^+$ = 464 | 1.24 min (Method A) |

Example 34

Synthesis of Compound 1175

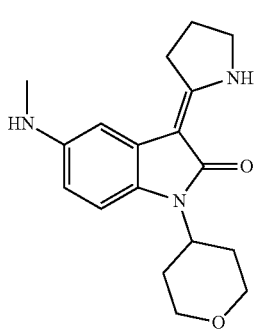 [SMILES: CNc1ccc2c(c1)/C(=C1\CCCN1)C(=O)N2C1CCOCC1]

Intermediate C35 (200 mg; 0.52 mmol) and Raney-Nickel (50 mg) in MeOH (10 mL) are hydrogenated in a Parr apparatus (rt; 1.1 bar; 8 h). The catalyst is filtered off and the solvent is evaporated. The residue is purified by preparative HPLC (eluent A: water+0.1% conc. ammonia, eluent B: MeOH).

MS (ESI$^+$): m/z=314 [M+H]$^+$
HPLC (Method M): $R_t$=1.12 min

Example 35

Synthesis of Compound 1176

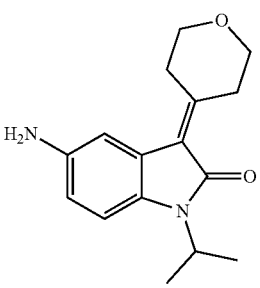

Intermediate C4 (1.78 g; 5.90 mmol) and powdered iron (1.78 g; 31.87 mmol) in water (56.5 mL) and ethanol (116 mL) are stirred at 80° C. Glacial acetic acid (3.58 mL; 62.55 mmol) are added drop wise and the mixture is stirred for 1 h at 80° C. The organic solvent is evaporated and the aq. layer is alkalised with NaOH (7 mL) and extracted with DCM. Iron is filtered off through celite. The organic layer is separated, dried and evaporated. The residue is purified by HPLC (eluent A: water+0.15% conc. ammonia, eluent B: MeOH).

MS (ESI$^+$): m/z=273 [M+H]$^+$
HPLC (Method A): $R_t$=1.16 min

Example 36

Synthesis of Compound 1177

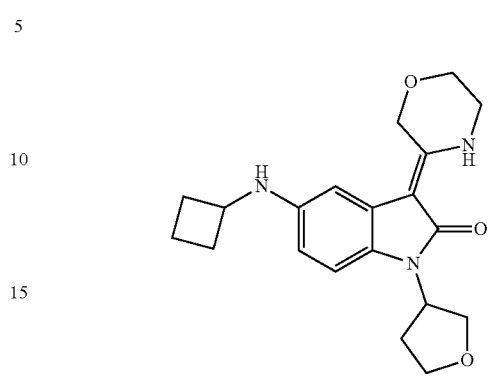

Intermediate D1 (150 mg; 0.50 mmol), bromo-cyclobutane (101 mg; 0.75 mmol) and potassium carbonate (138 mg; 1.00 mmol) in DMF (3 mL) are stirred at 70° C. for 4 h. Additional bromo-cyclobutane (101 mg; 0.75 mmol) is added and the mixture is stirred at 80° C. over night. Additional bromo-cyclobutane (101 mg; 0.75 mmol) is added. After stirring for 4 h at 90° C. the mixture is purified by preparative HPLC (eluent A: water+0.15% conc. ammonia, eluent B: MeOH).

MS (ESI$^+$): m/z=356 [M+H]$^+$
HPLC (Method B): $R_t$=0.89 min

Example 37

Synthesis of Compound 1178

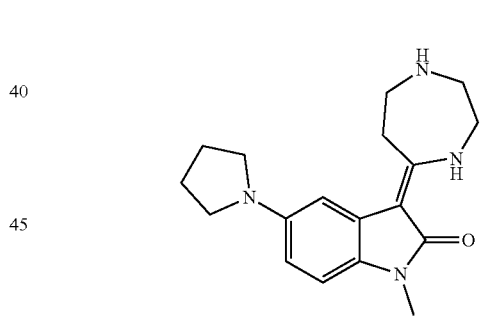

Example 146 (65 mg; 0.15 mmol) and Pd/C (10%; 10 mg) in MeOH (5 mL) is hydrogenated in a Parr apparatus (rt; 50 psi; 1 h). The catalyst is filtered off and the solvent is removed.

The residue is purified by preparative HPLC (eluent A: water+0.15% conc. ammonia, eluent B: MeOH).

MS (ESI$^+$): m/z=313 [M+H]$^+$
HPLC (Method A): $R_t$=1.34 min

Example 38

Biological Assays

The biological activity of compounds is determined by the following methods:
Assay A: Determination of Complex I mediated ROS-inhibition (CI)

Enzyme kinetic experiments permit the detection of ROS generated through Complex I. Herefore Complex I was purified from bovine heart (Sharpley et al. 2006 Biochemistry. 45(1):241-8. First a subcellular fractionation was conducted to obtain a crude mitochondria fraction, followed by a hypotonoc lysis and differential centrifugation, from which mitochondrial membranes were obtained. Solubilzation of mitochondrial membranes followed by an ion exchange chromatography and size exclusion chromatography resulted in enzyme preparations which contain Complex I with little contaminations of Complex IV. These preparations were used to study ROS-generation by Complex I, the substrate NADH (1 μM) and oxygen (ambient). The generated ROS are detected via the Oxidation of Amplex red in a coupled reaction containing Amplex Red and horse radish peroxidase IC50 of a compound of the invention was estimated by testing the compound using a 8 point concentration-response experiment.

In 384-well microtiter plates 5 μl of test compound (final concentrations ranging from 0.01 nM to 30 μM, diluted in assay buffer and 1% DMSO final) or control was mixed with 5 μl of substrate mix (3 μM NADH, 10 μM AmplexRed, 1 mM Fructose 1,6 bis-phopshate and 1 mM AsO4). The enzymatic reaction was started by addition of 15 μl of enzyme mix (containing 20 μg/ml Complex I, 2 U/ml horse radish peroxidase, 1 U/ml Aldolase, 1 U/ml Triosei-somerase, 1 U/ml Glycerinaldehyd-3-phosphat-Dehydrogenase) and the generation of ROS was followed by measuring the increase in absorption at 557 nm every 53 seconds at room temperature for 12 minutes, followed by linear regression (slope analysis). To assess the potency of Compounds IC50 values are calculated as 50% activity of Complex I by nonlinear regression curve fitting, using a 4-parameter sigmoidal dose-response model.

Assay B: Determination of Cellular Protection (HT22)

To show selective pathway engagement in a cellular context, a mice neuroblastoma cells (HT-22) were depleted of the endogenous antioxidant glutathione resulting on oxidative stress on the mitochondrial and cellular level and cell death (Tan S, Sagara Y, Liu Y, Maher P, Schubert D. The regulation of reactive oxygen species production during programmed cell death. J Cell Biol. 1998; 141:1423-1432). By incubation with high concentrations of Glutamate (5 mM) these cells are depleted of intracellular glutathione do to a inhibition of cystine uptake, which results in an accumulation of mitochondrial derived ROS and ultimately cell death.

In 384-well plates, 2000 HT-22 cells were seeded in 50 ul cell culture medium (DMEM containing 10% fetal calf serum and 1% penicillin/streptomycin) and were cultured for 24 hours, followed by the incubation with glutamate (to induce cell death) or vehicle (viable cells (100%) in presence of test compound (0.01-30 uM final) for 16 hours. Viability of the cells were assessed by adding 10% Alamar Blue reagent and incubation for 1 h at 37° C., followed by measuring Fluorescence (excitation 530 nm, emission 590 nm.

To assess the potency of compounds, EC50 values were calculated by nonlinear regression curve fitting, using a 4-parameter sigmoidal dose-response model (see Complex I assay).

The invention claimed is:
1. A compound having formula (I) or a salt thereof

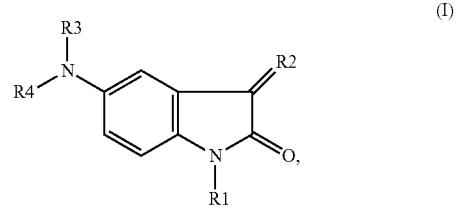

wherein:
R1 is $C_{1-4}$-alkyl unsubstituted or substituted with MeO; tetrahydropyranyl, tetrahydrofuranyl, oxetanyl, dioxepanyl, pyrrolidinyl or piperidinyl; or
pyrrolidinyl or piperidinyl with the nitrogen substituted by methyl, isopropyl, oxetanyl, ethoxycarbonyl, acetyl, or trifluoroacetyl;
R2 is a 5-, 6- or 7-membered ring containing 1 or 2 heteroatoms selected from O or N bound in formula (I) by a C=C double bond,
in which one or both N-atoms can be substituted by methyl, isopropyl, acetyl, benzyloxycarbonyl, phenyl, oxetanyl or tetrahydropyranyl, and
in which one or more C-atoms can be substituted by -methyl or —OH;
R3 and R4 are independently from one another
hydrogen; $C_{1-6}$-alkyl, unsubstituted or substituted with one or more F, methoxy, $C_{3-8}$-cycloalkyl unsubstituted or substituted with one or more F; aryl; heteroaryl consisting of 5 to 6 ring atoms; or heterocyclyl selected from the group consisting of oxetanyl, tetrahydropyranyl and pyrrolidinyl, said heterocyclyl being unsubstituted or substituted with $C_{1-6}$-alkyl, acetyl, tetrahydrofuranyl, oxetanyl or hydroxyethylacetyl;
or R3 and R4 together with the attached N form a heterocyclyl ring selected from the group consisting of morpholinyl and pyrrolidinyl both unsubstituted or substituted with $C_{1-6}$-alkyl, F, or hydroxyl;
or R3 and R4 together represent one of the following groups:

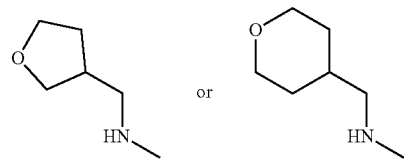

2. A compound selected from the group consisting of the following compounds 1 to 175, or a salt thereof:

| # | Structure |
|---|-----------|
| 1 | 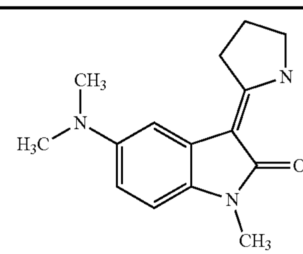 |

-continued
| # | Structure |
|---|---|
| 2 | 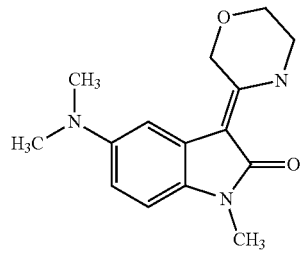 |
| 3 | 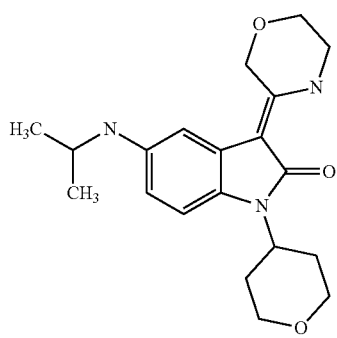 [SMILES: CC(C)Nc1ccc2c(c1)/C(=C1\COCCN1)C(=O)N2C1CCOCC1] |
| 4 | 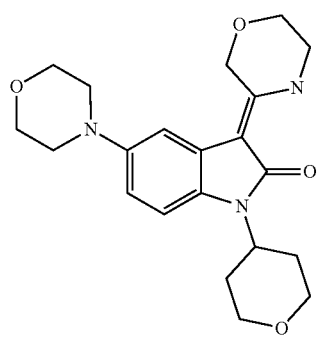 [SMILES: O=C1/C(=C2/COCCN2)c2cc(N3CCOCC3)ccc2N1C1CCOCC1] |
| 5 | 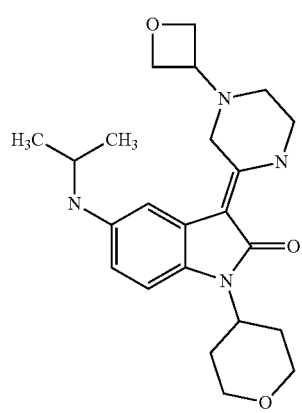 |
-continued
| # | Structure |
|---|---|
| 6 | 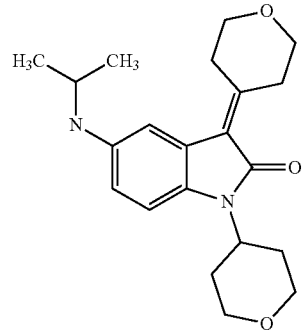 [SMILES: CC(C)Nc1ccc2c(c1)C(=C1CCOCC1)C(=O)N2C1CCOCC1] |
| 7 | 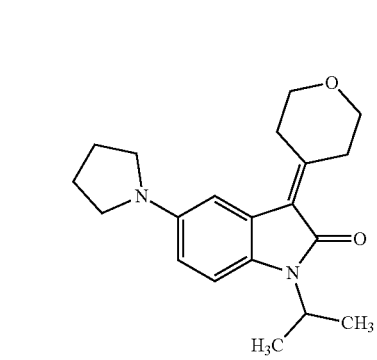 [SMILES: CC(C)N1C(=O)C(=C2CCOCC2)c2cc(N3CCCC3)ccc21] |
| 8 | 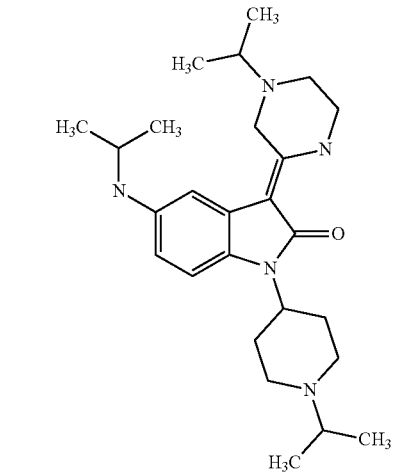 [SMILES: CC(C)Nc1ccc2c(c1)/C(=C1\CN(C(C)C)CCN1)C(=O)N2C1CCN(C(C)C)CC1] |
| 9 | 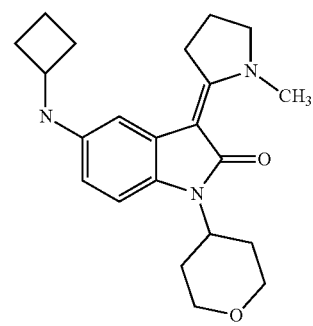 |

| # | Structure |
|---|---|
| 10 | 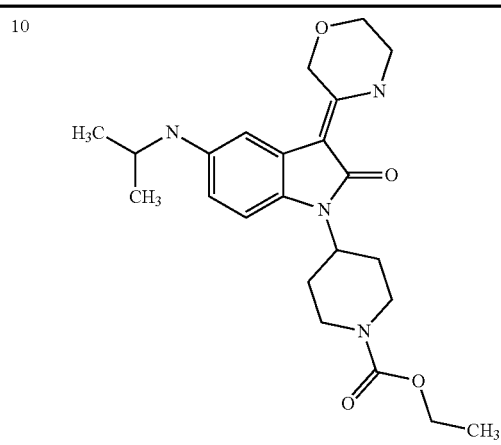 |
| 11 | 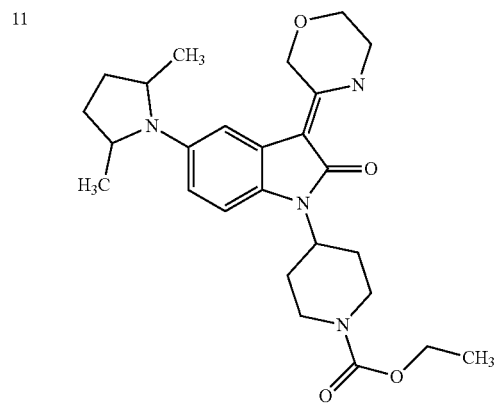 |
| 12 | 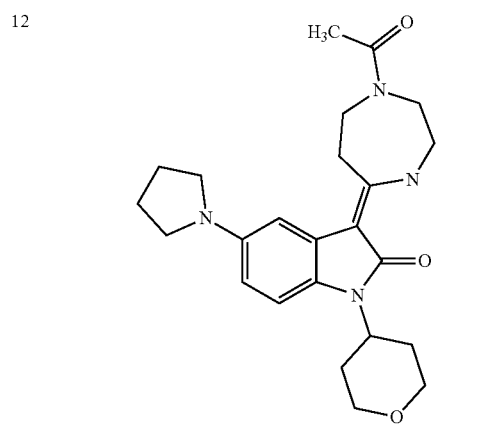 |
| 13 | 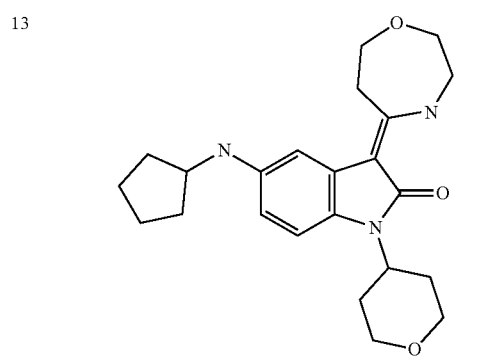 |
| # | Structure |
|---|---|
| 14 | 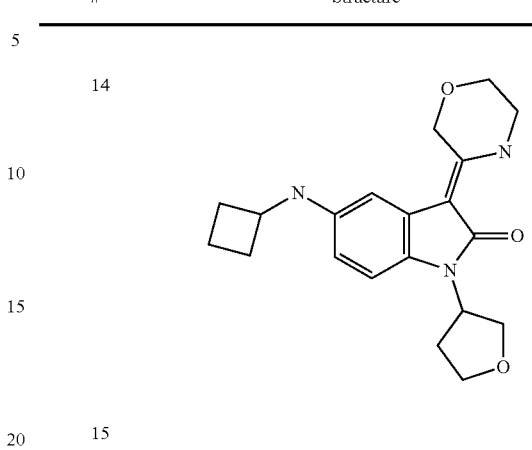 |
| 15 | 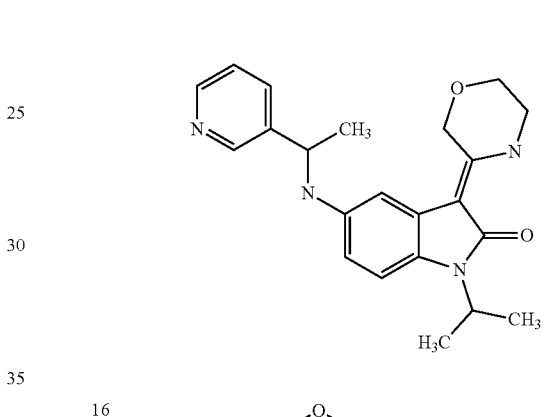 |
| 16 | 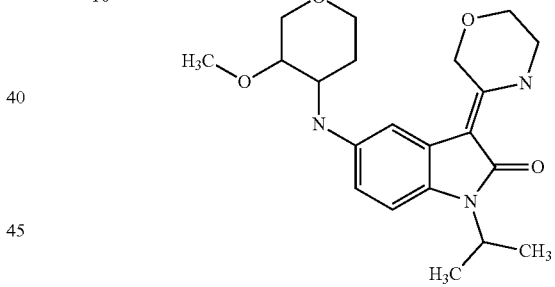 |
| 17 | 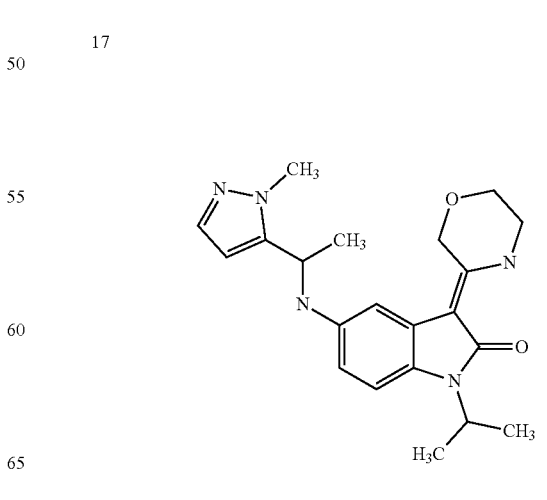 |

| # | Structure |
|---|---|
| 18 | 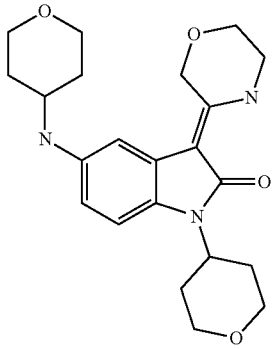 |
| 19 | 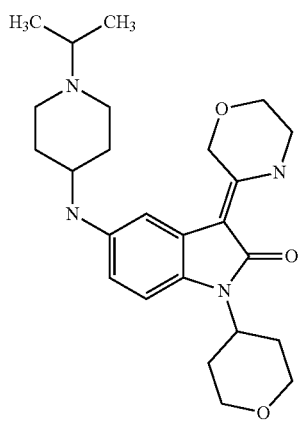 |
| 20 | 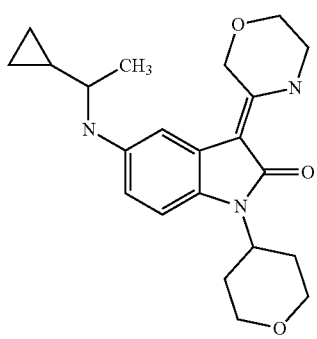 |
| 21 | 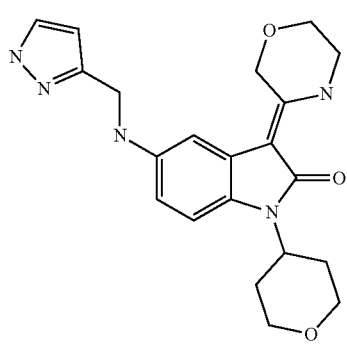 |
| # | Structure |
|---|---|
| 22 | 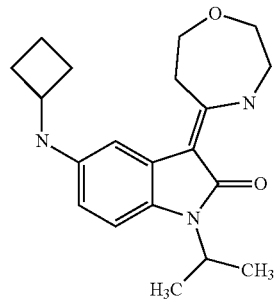 |
| 23 | 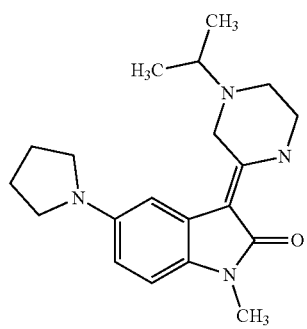 |
| 24 | |
| 25 | 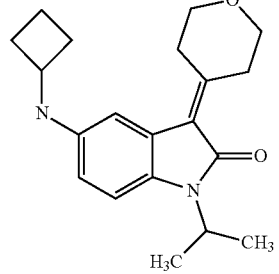 |

| # | Structure |
|---|---|
| 26 | 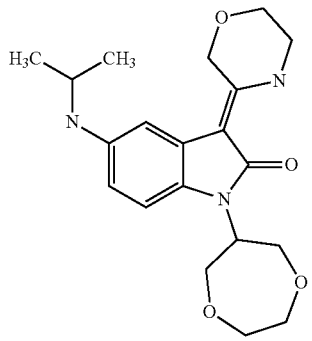 |
| 27 | 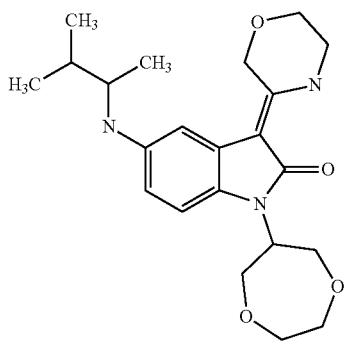 |
| 28 | 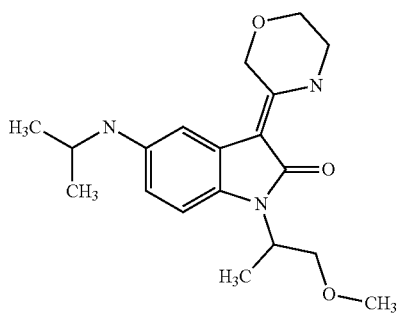 |
| 29 | 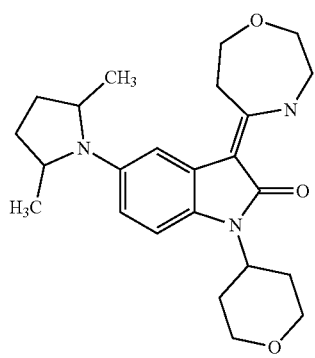 |
| # | Structure |
|---|---|
| 30 | 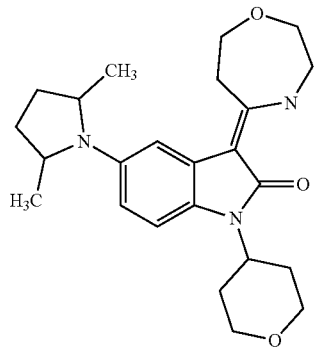 |
| 31 | 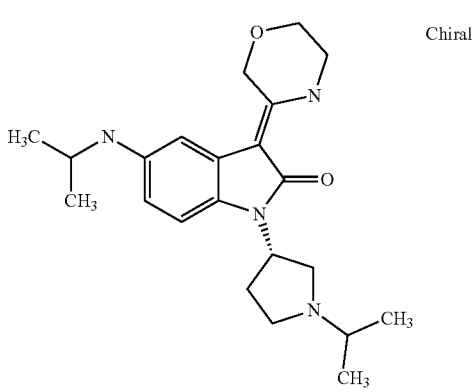 Chiral |
| 32 | 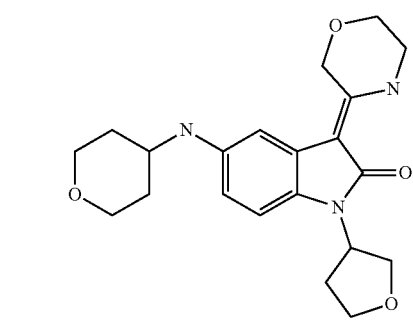 |
| 33 | 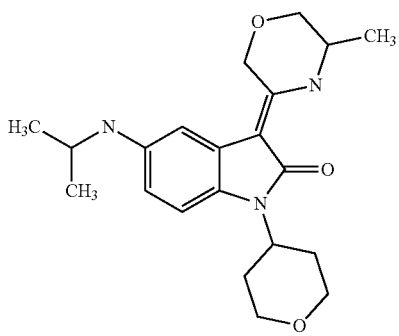 |

-continued
| # | Structure |
|---|---|
| 34 | 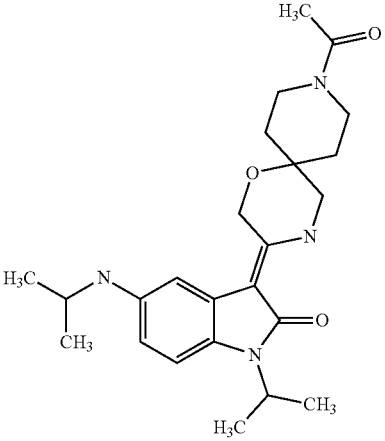 |
| 35 | 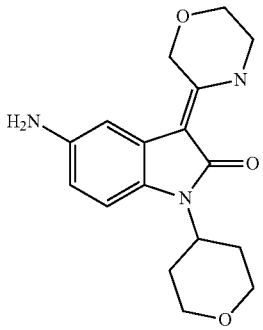 |
| 36 | 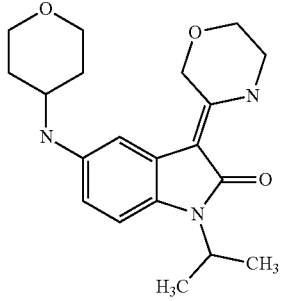 |
| 37 | 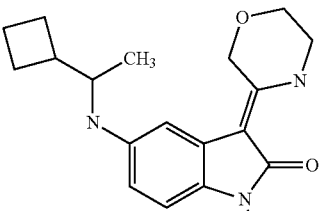 |
-continued
| # | Structure |
|---|---|
| 38 | 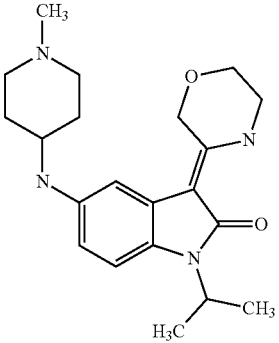 |
| 39 | 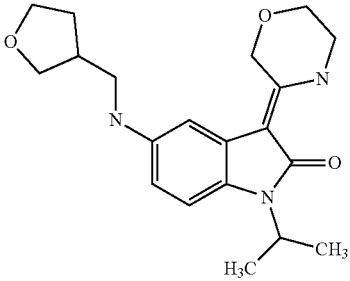 |
| 40 | 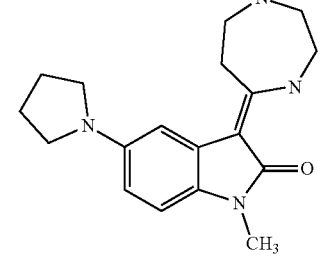 |
| 41 | 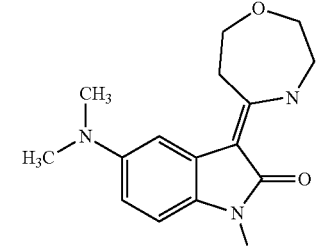 |
| 42 | 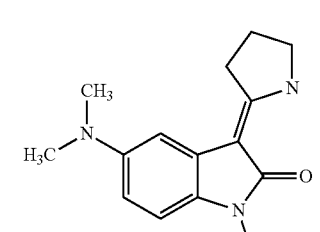 |

| # | Structure |
|---|---|
| 43 | 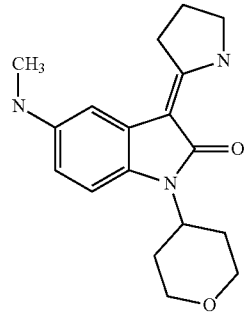 |
| 44 | 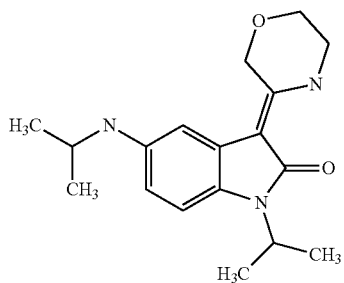 |
| 45 | 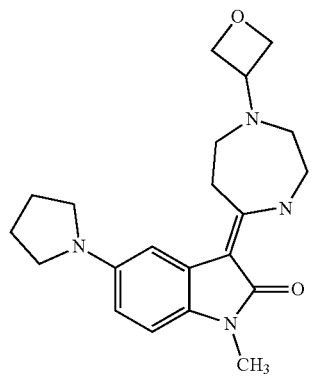 |
| 46 | 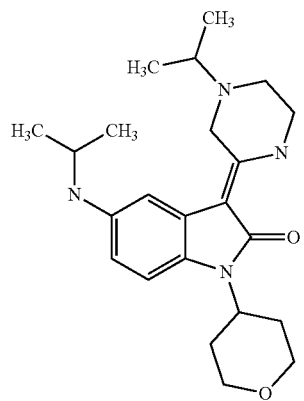 |
| # | Structure |
|---|---|
| 47 | 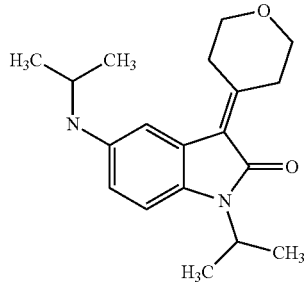 |
| 48 | 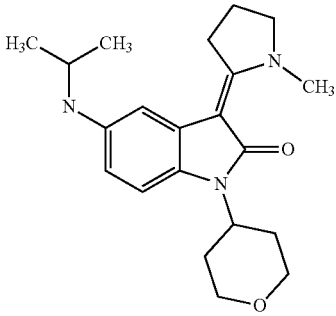 |
| 49 | 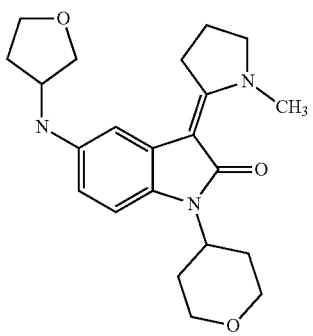 |
| 50 | 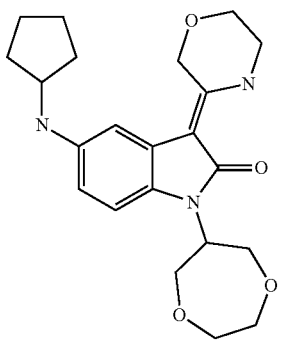 |
| 51 | 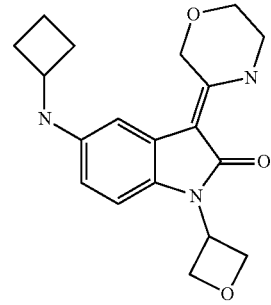 |

| # | Structure |
|---|---|
| 52 | 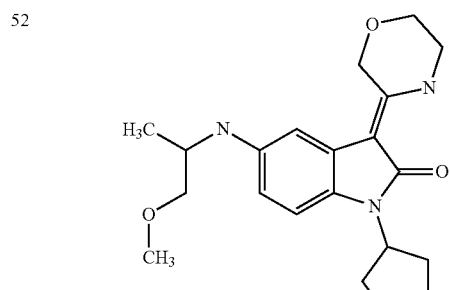 |
| 53 | 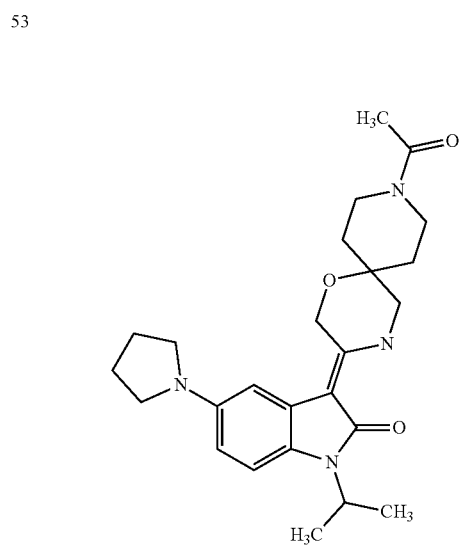 |
| 54 | 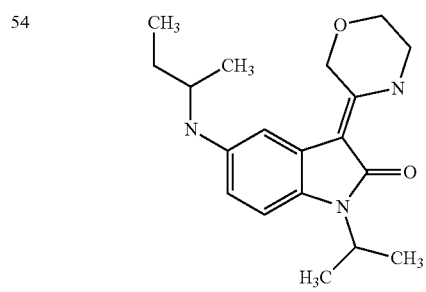 |
| 55 | 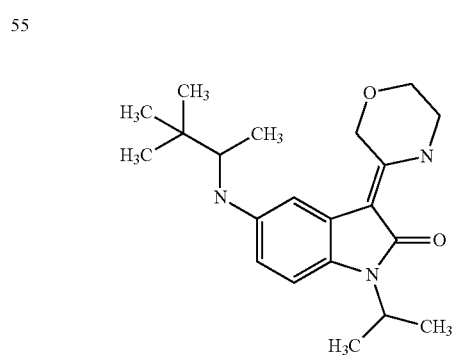 |
| # | Structure |
|---|---|
| 56 | 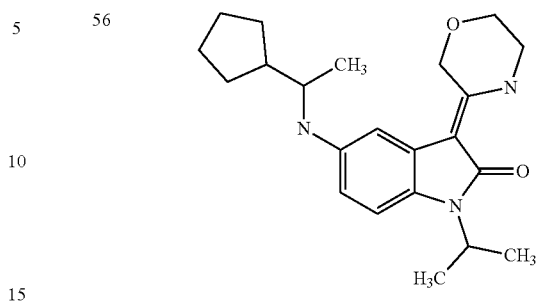 |
| 57 | 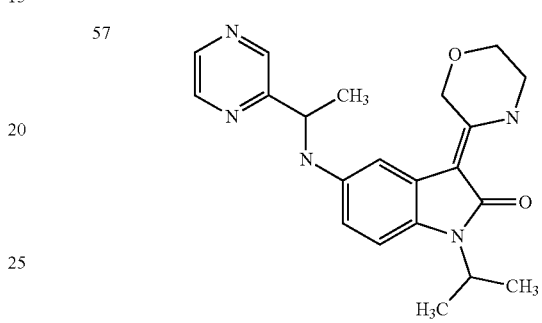 |
| 58 | 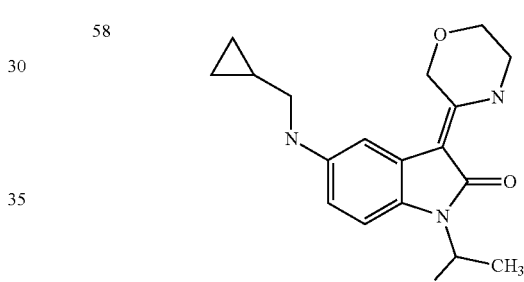 |
| 59 | 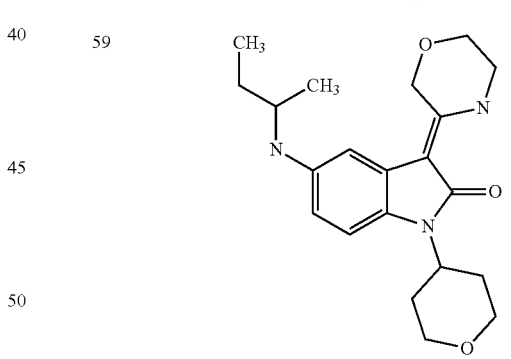 |
| 60 | 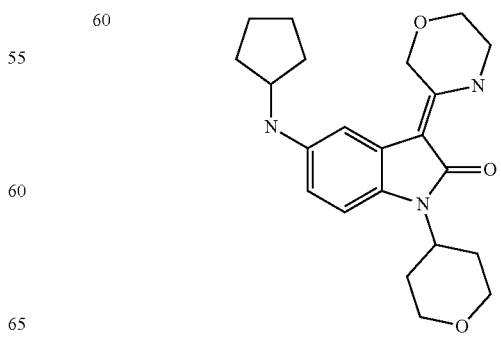 |

-continued

| # | Structure |
|---|---|
| 61 | 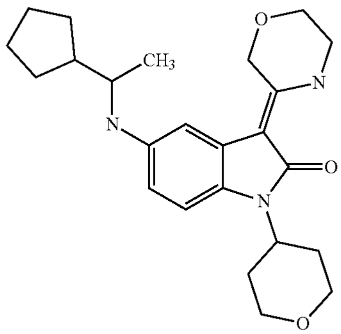 |
| 62 | 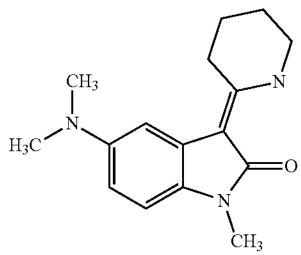 |
| 63 | 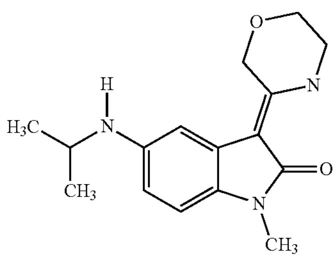 |
| 64 | 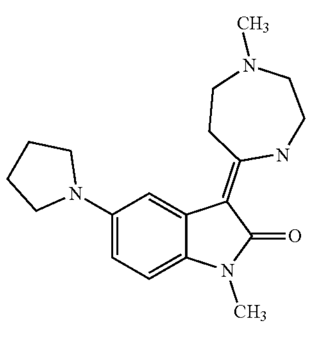 [SMILES: CN1CCN/C(=C2\C(=O)N(C)c3ccc(N4CCCC4)cc32)CC1] |
| 65 | 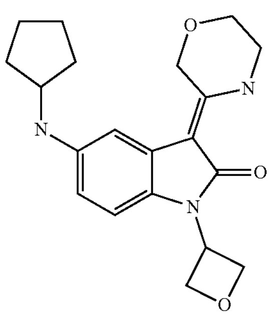 [SMILES: O=C1/C(=C2/COCCN2)c2cc(NC3CCCC3)ccc2N1C1COC1] |

-continued

| # | Structure |
|---|---|
| 66 | 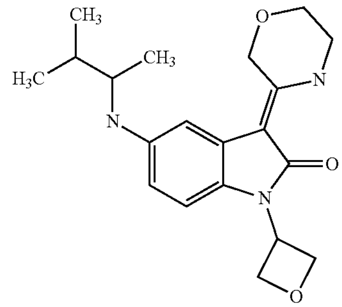 [SMILES: CC(C)C(C)Nc1ccc2c(c1)/C(=C1\COCCN1)C(=O)N2C1COC1] |
| 67 | 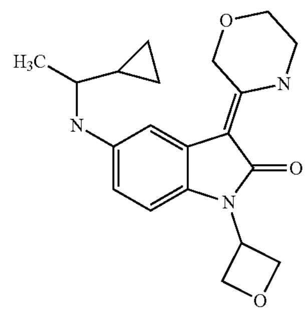 [SMILES: CC(Nc1ccc2c(c1)/C(=C1\COCCN1)C(=O)N2C1COC1)C1CC1] |
| 68 | 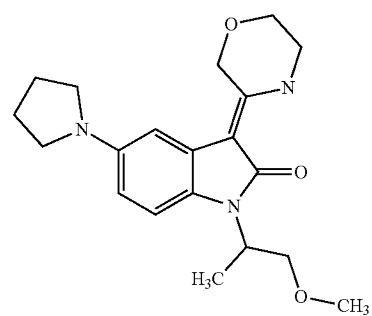 |
| 69 | Chiral |

-continued
| # | Structure |
|---|---|
| 70 | 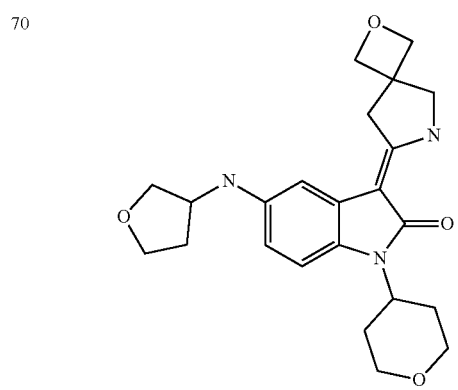 |
| 71 | 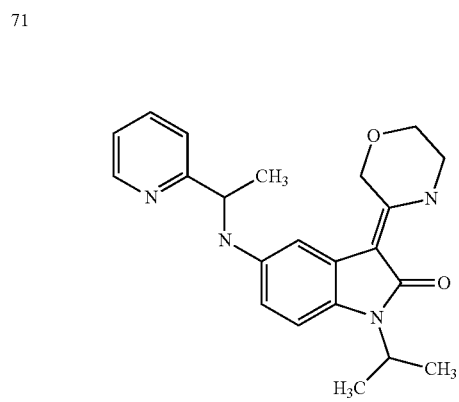 |
| 72 | 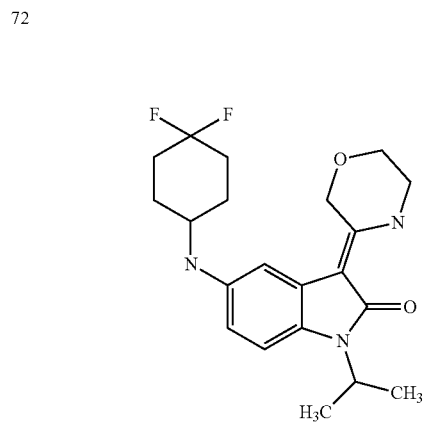 |
| 73 | 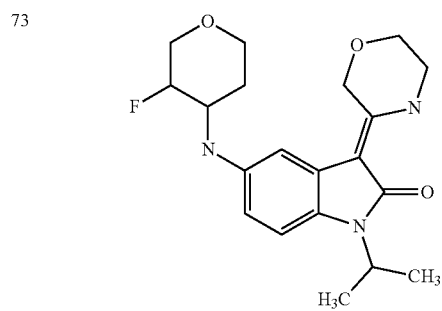 |
-continued
| # | Structure |
|---|---|
| 74 | 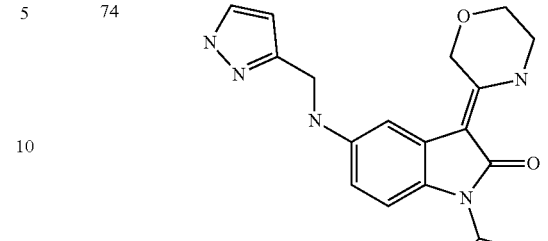 |
| 75 | 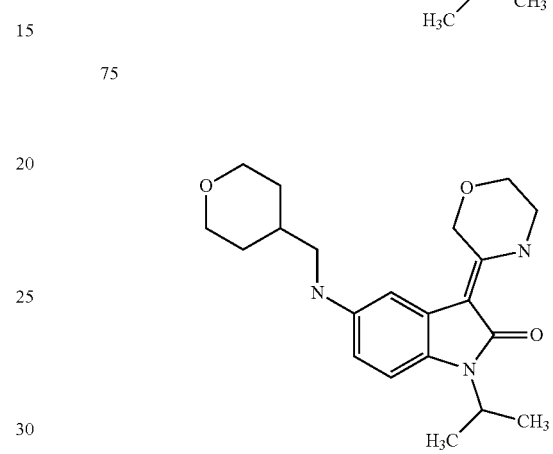 |
| 76 | 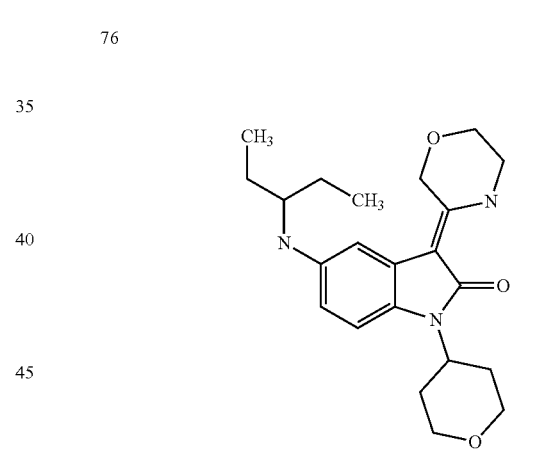 |
| 77 | 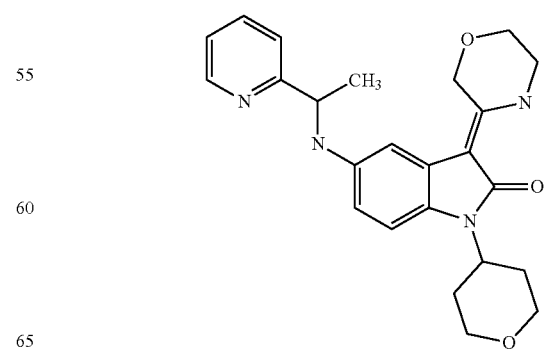 |

255
-continued
| # | Structure |
|---|---|
| 78 | 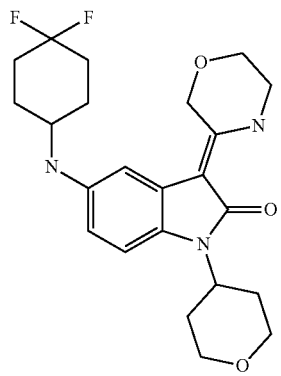 |
| 79 | 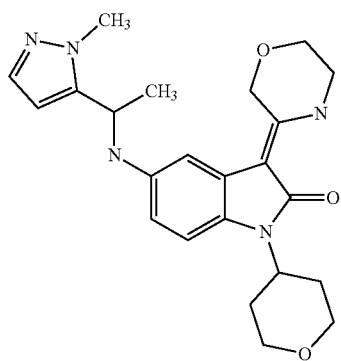 |
| 80 | 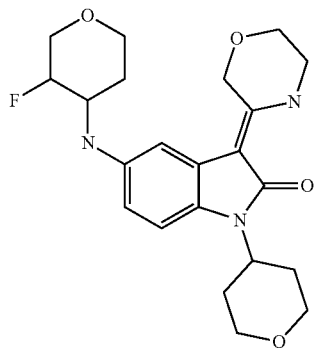 |
| 81 | 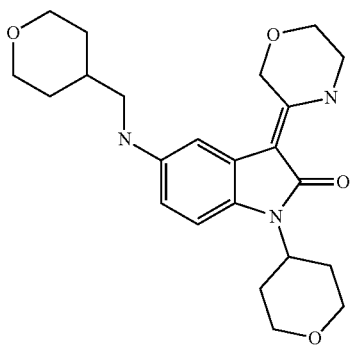 |
256
-continued
| # | Structure |
|---|---|
| 82 | 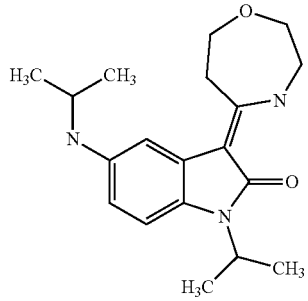 |
| 83 | 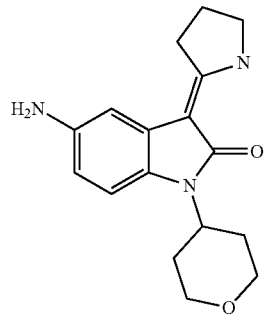 |
| 84 | 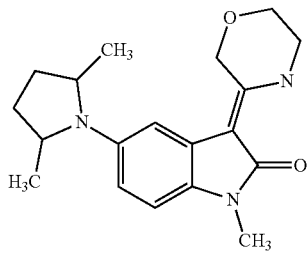 |
| 85 | 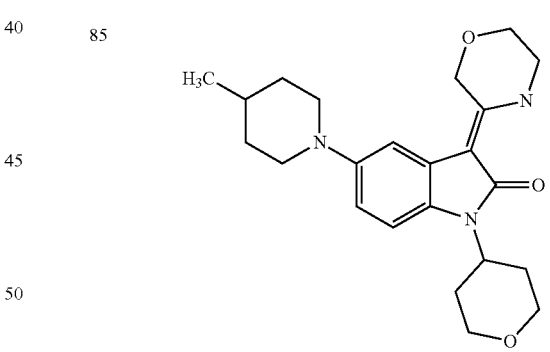 |
| 86 | 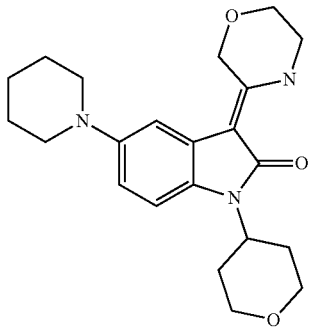 |

| # | Structure |
|---|---|
| 87 | 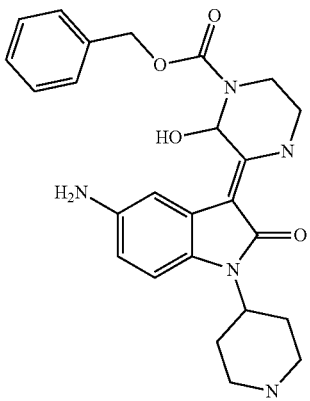 [SMILES: Nc1ccc2c(c1)/C(=C1/NCCN(C(=O)OCc3ccccc3)C1O)C(=O)N2C1CCNCC1] |
| 88 | 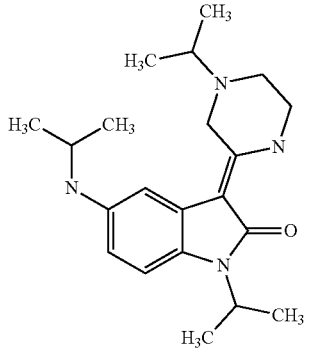 [SMILES: CC(C)Nc1ccc2c(c1)/C(=C1\CN(C(C)C)CCN1)C(=O)N2C(C)C] |
| 89 | 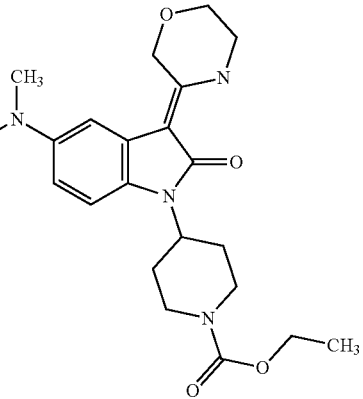 |
| 90 | 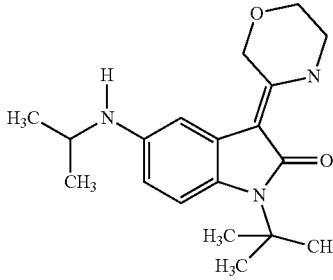 |
| # | Structure |
|---|---|
| 91 | 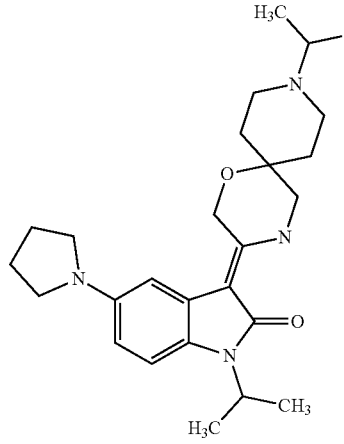 |
| 92 | 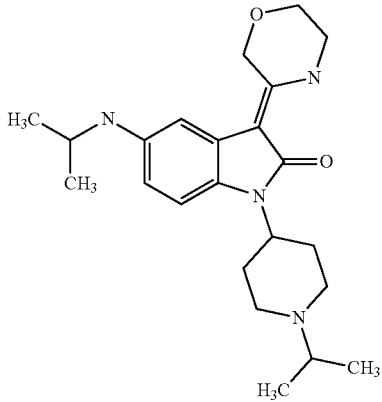 [SMILES: CC(C)Nc1ccc2c(c1)/C(=C1\COCCN1)C(=O)N2C1CCN(C(C)C)CC1] |
| 93 | 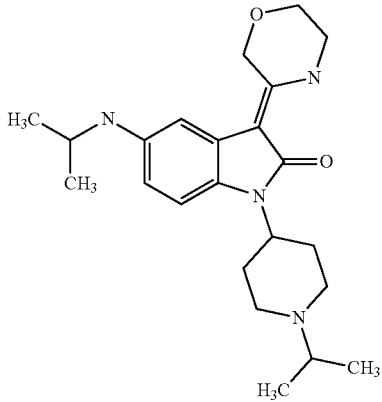 [SMILES: CC(C)Nc1ccc2c(c1)/C(=C1\COCCN1)C(=O)N2C1CCN(C(C)C)CC1] |
| 94 | 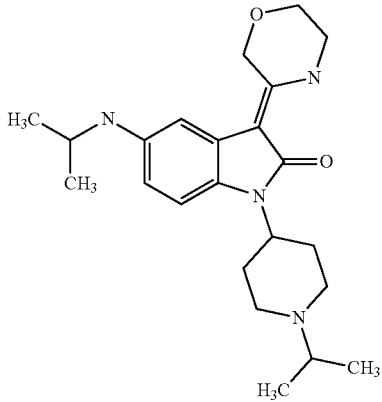 [SMILES: CC(C)Nc1ccc2c(c1)/C(=C1\COCCN1)C(=O)N2C1CCN(C(C)C)CC1] |

| # | Structure |
|---|---|
| 95 | 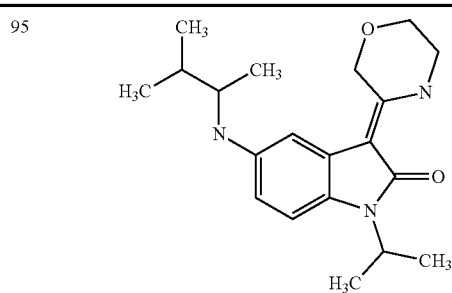 |
| 96 | 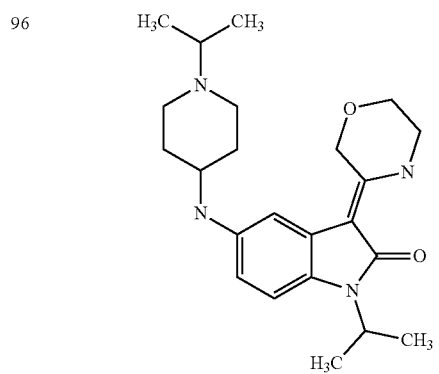 |
| 97 | 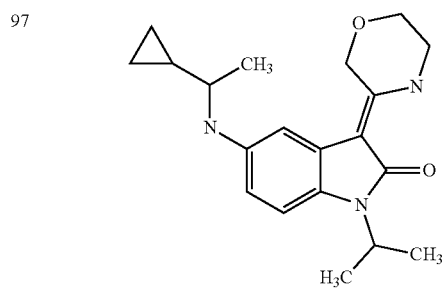 |
| 98 | 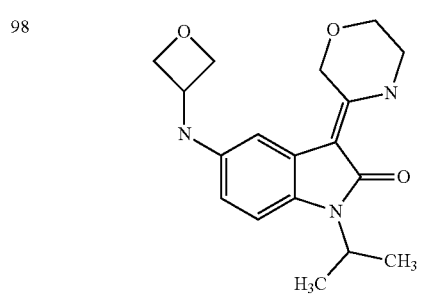 |
| 99 | 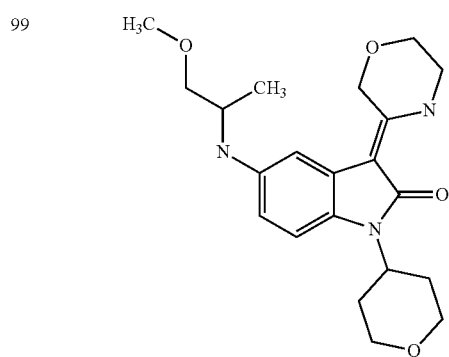 |
| # | Structure |
|---|---|
| 100 | 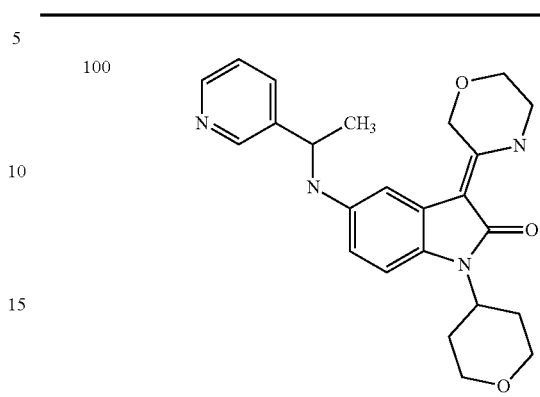 |
| 101 | 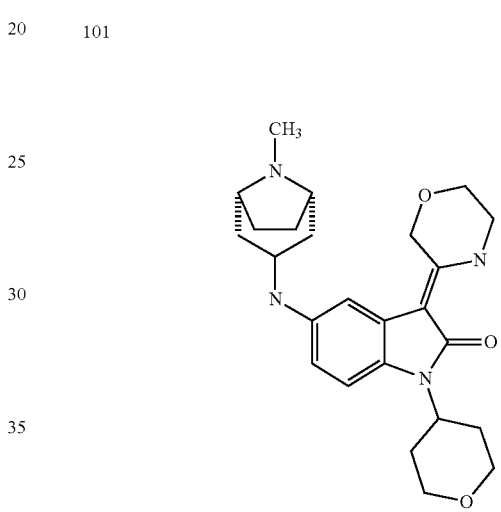 |
| 102 | 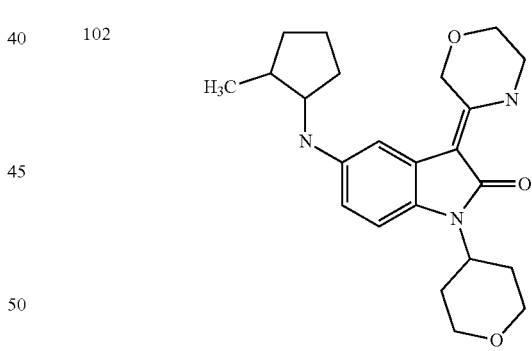 |
| 103 | 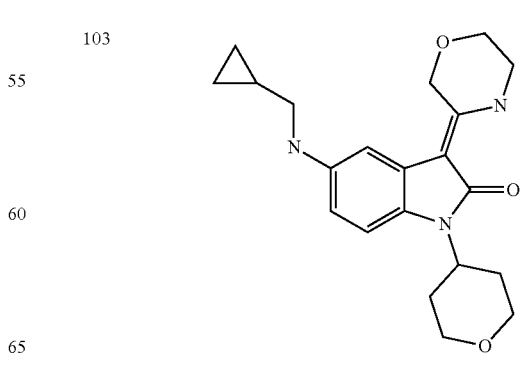 |

261
-continued
| # | Structure |
|---|---|
| 104 | 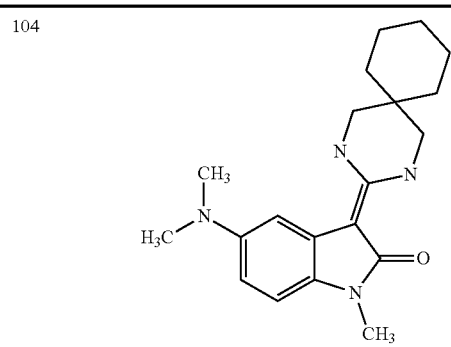 |
| 105 | 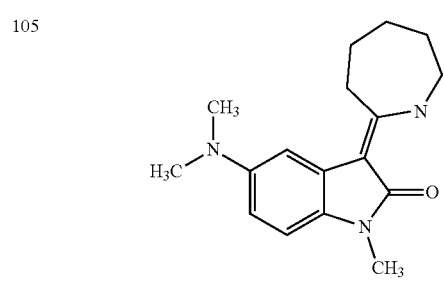 |
| 106 | 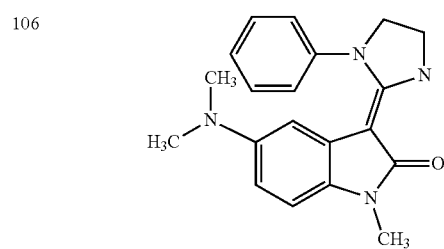 |
| 107 | 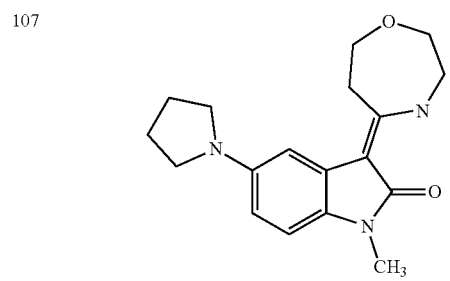 |
| 108 | 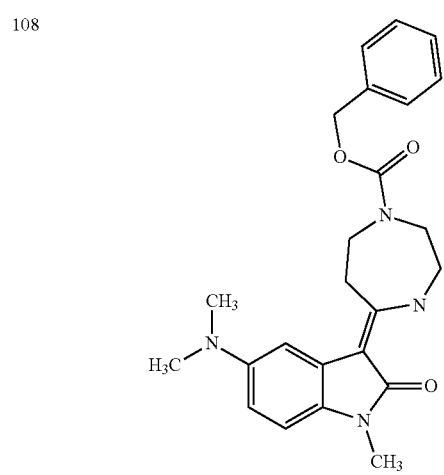 |
262
-continued
| # | Structure |
|---|---|
| 109 | 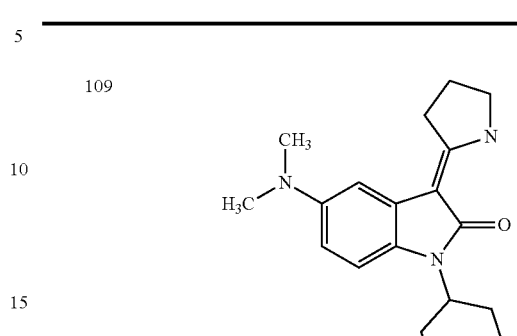 |
| 110 | 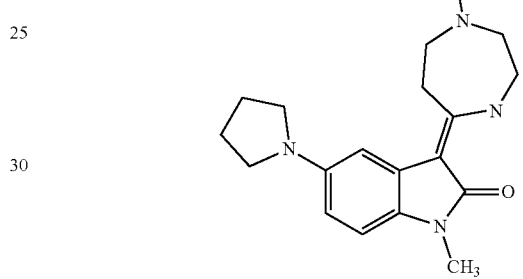 |
| 111 | 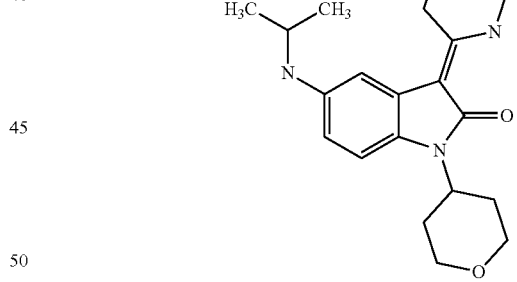 |
| 112 | 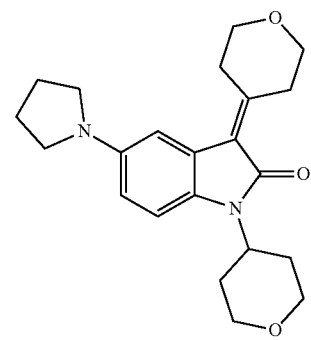 [SMILES: O=C1C(=C2CCOCC2)c2cc(N3CCCC3)ccc2N1C1CCOCC1] |

-continued

| # | Structure |
|---|---|
| 113 | 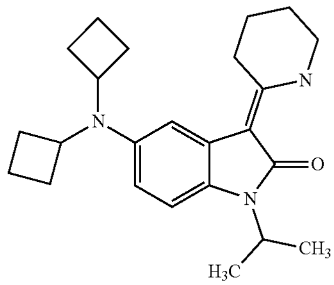 |
| 114 | 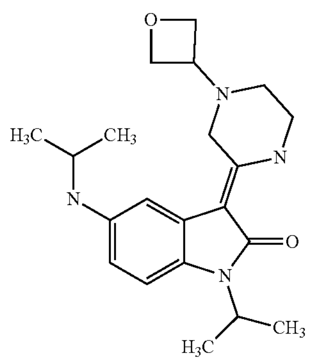 |
| 115 | 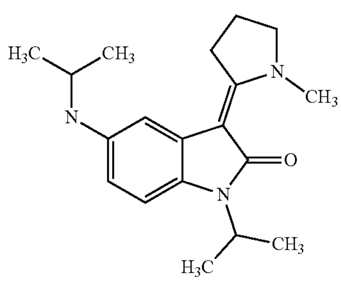 |
| 116 | 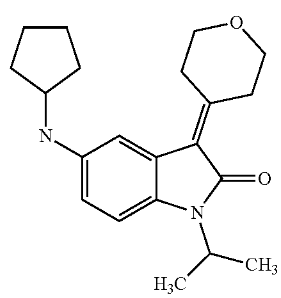 |
| 117 | 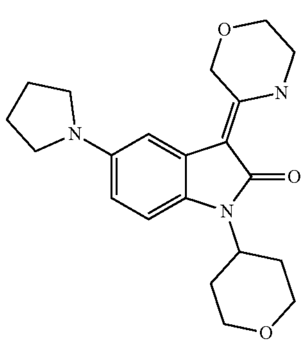 |

-continued

| # | Structure |
|---|---|
| 118 | 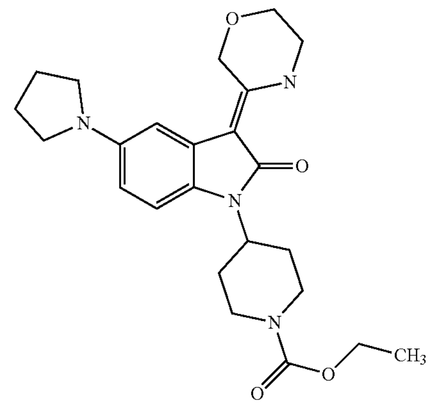 |
| 119 | 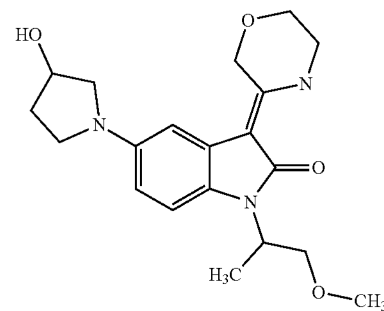 |
| 120 | 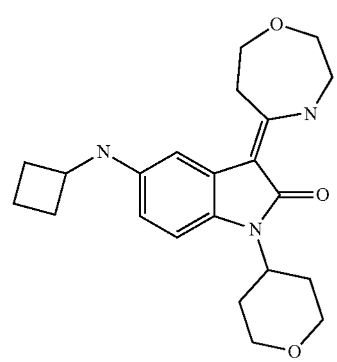 |
| 121 | 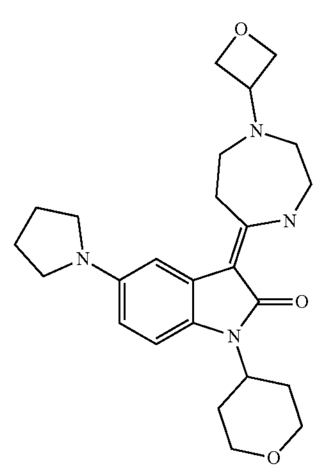 |

265
-continued
| # | Structure |
|---|---|
| 122 | 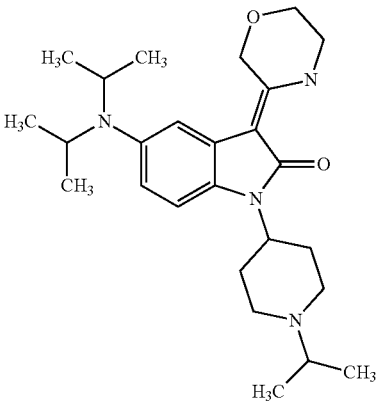 |
| 123 | 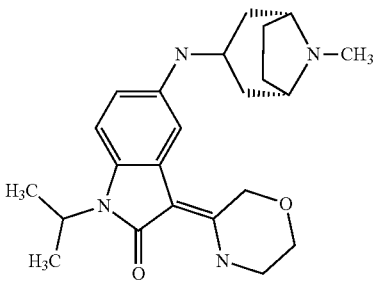 |
| 124 | 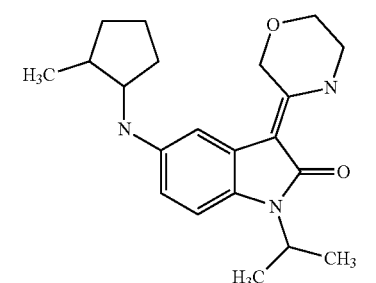 |
| 125 | 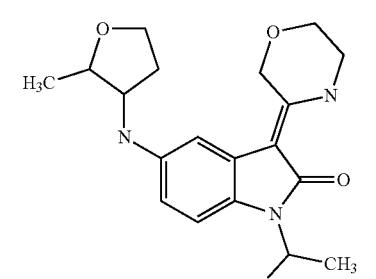 |
| 126 | 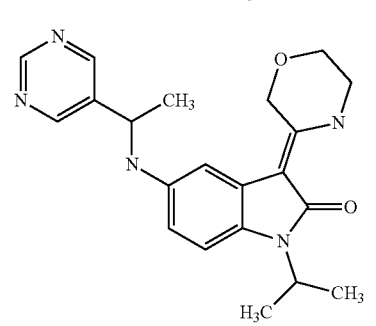 |
266
-continued
| # | Structure |
|---|---|
| 127 | 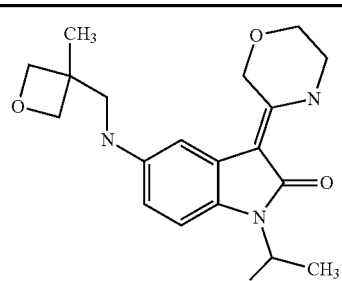 |
| 128 | 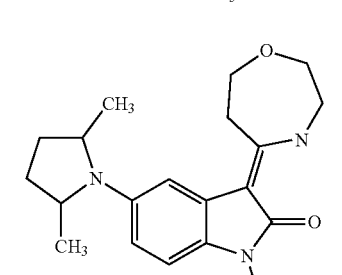 |
| 129 | 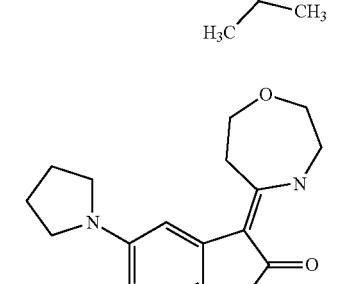 |
| 130 | 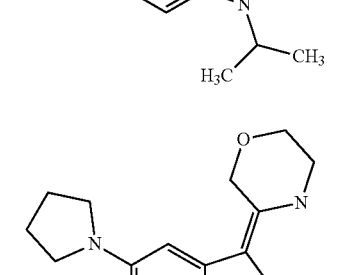 |
| 131 | 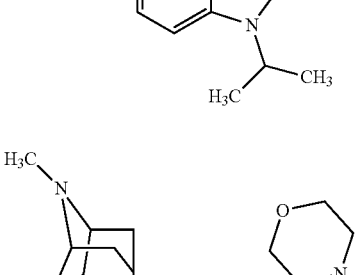 |

| # | Structure |
|---|---|
| 132 | 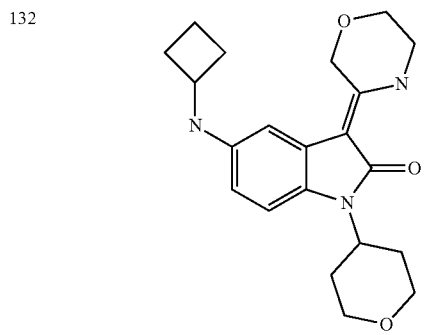 |
| 133 | 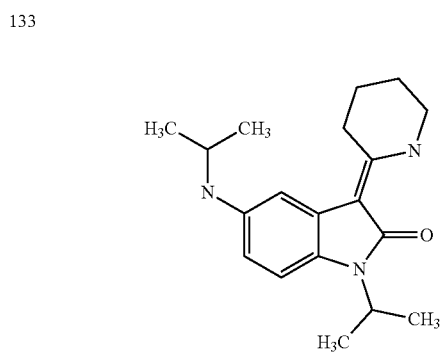 |
| 134 | 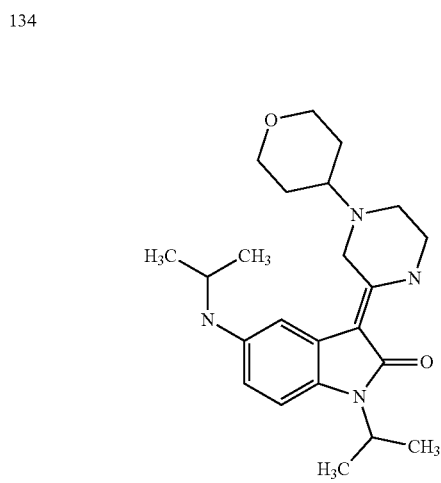 |
| 135 | 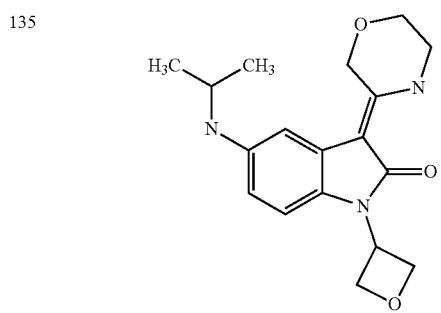 |
| # | Structure |
|---|---|
| 136 | 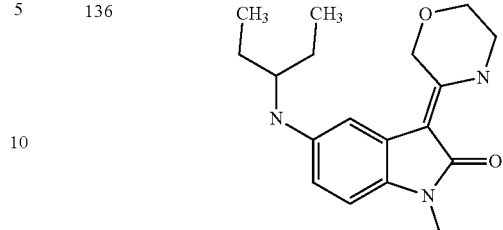 |
| 137 | 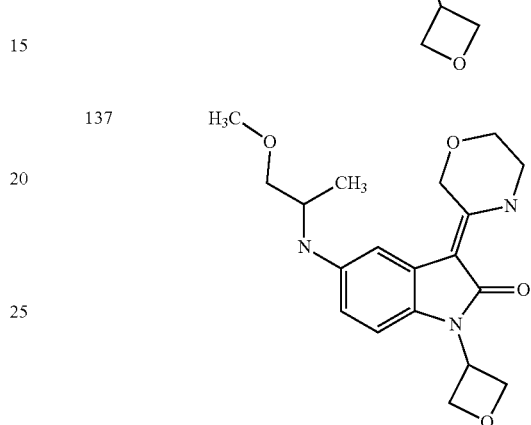 |
| 138 | 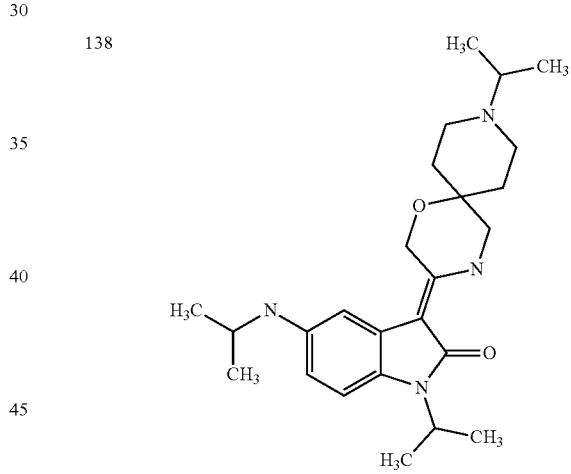 |
| 139 | 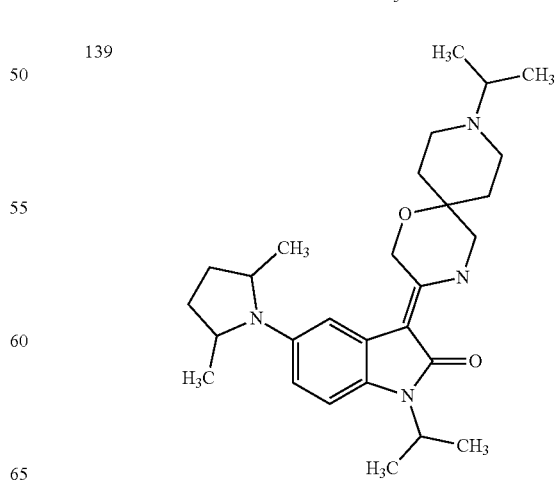 |

269
-continued
| # | Structure |
|---|---|
| 140 | 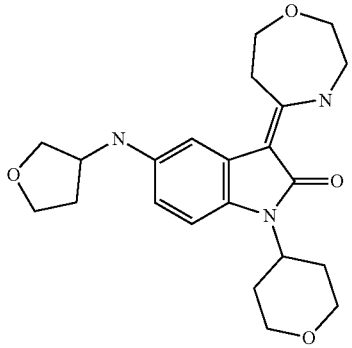 |
| 141 | 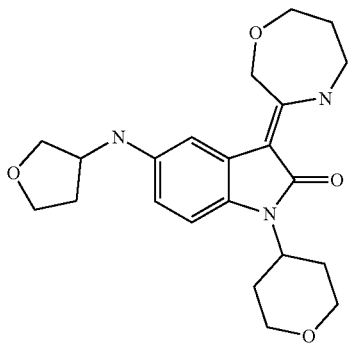 |
| 142 | 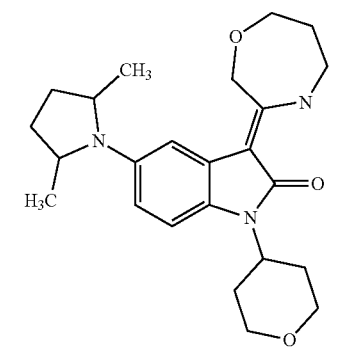 |
| 143 | 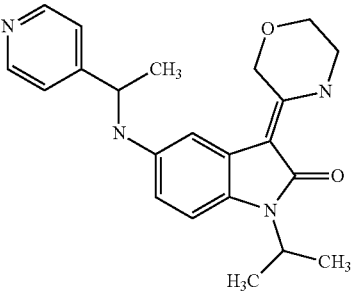 |
270
-continued
| # | Structure |
|---|---|
| 144 | 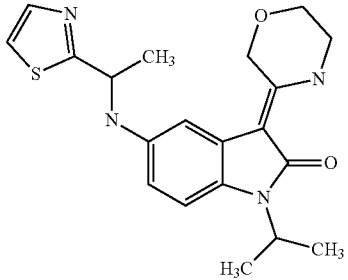 |
| 145 | 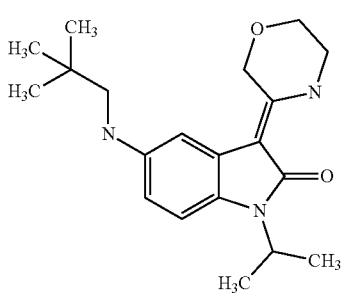 |
| 146 | 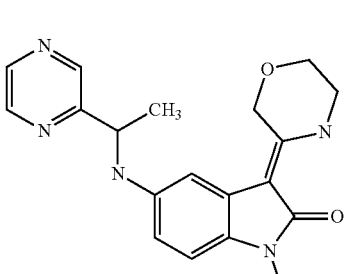 |
| 147 | 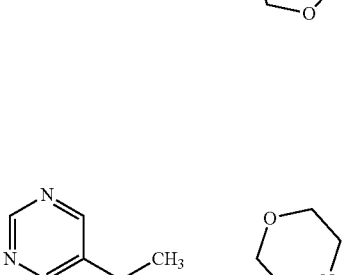 |

-continued
| # | Structure |
|---|---|
| 148 | 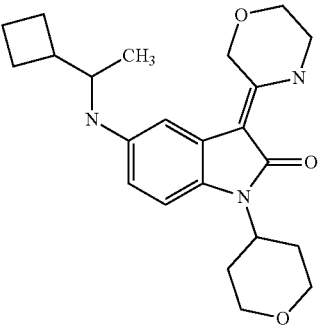 |
| 149 | 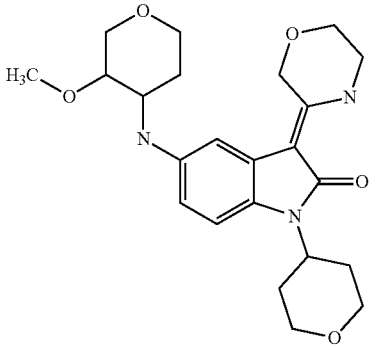 |
| 150 | 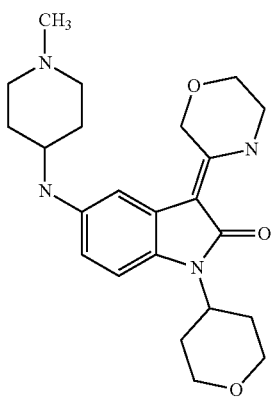 |
| 151 | 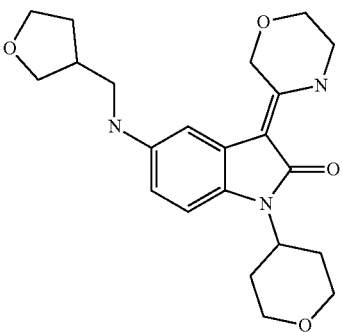 |
-continued
| # | Structure |
|---|---|
| 152 | 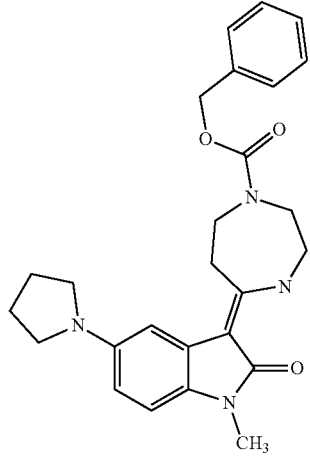 |
| 153 | 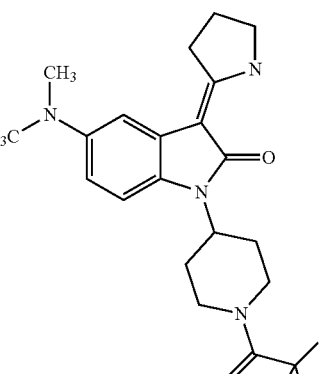 |
| 154 | 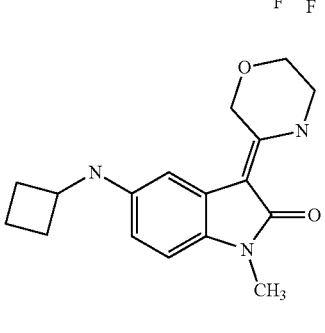 |
| 155 | 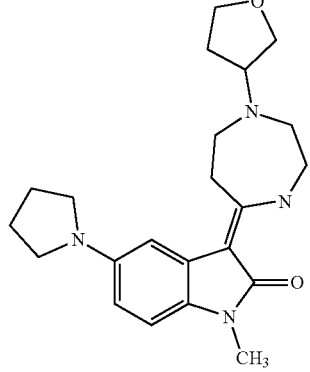 |

273
-continued

| # | Structure |
|---|---|
| 156 | 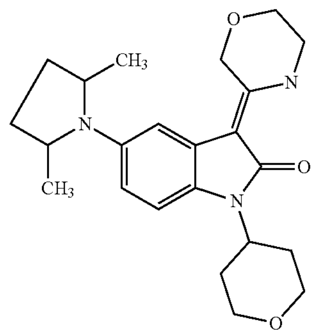 |
| 157 | 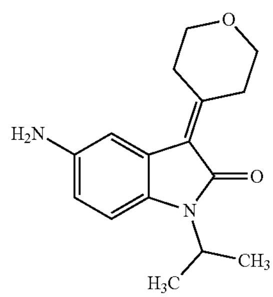 [SMILES: CC(C)N1C(=O)C(=C2CCOCC2)c2cc(N)ccc21] |
| 158 | 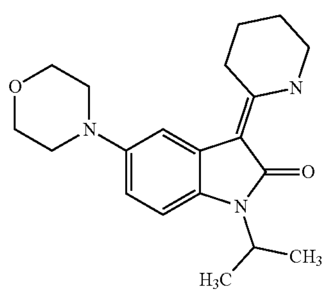 |
| 159 | 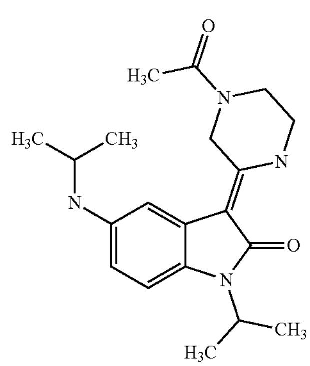 [SMILES: CC(=O)N1CCN/C(=C2\C(=O)N(C(C)C)c3ccc(NC(C)C)cc32)C1] |
| 160 | 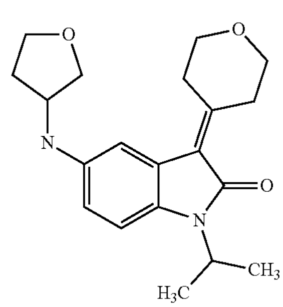 |

274
-continued

| # | Structure |
|---|---|
| 161 | 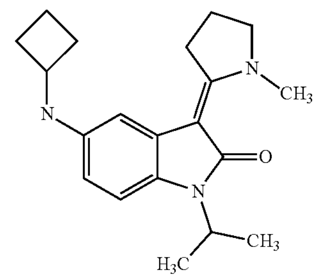 |
| 162 | 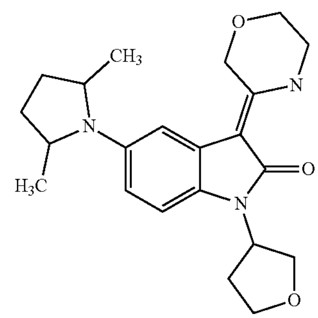 |
| 163 | 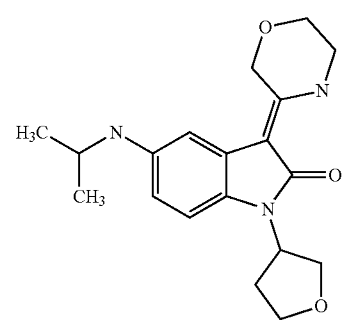 |
| 164 | 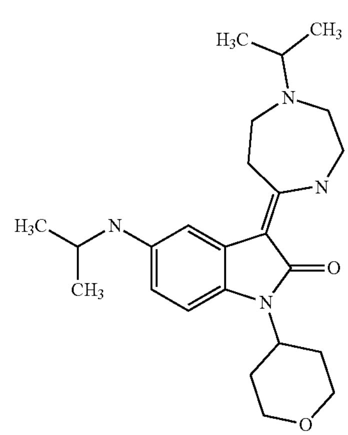 |

| # | Structure |
|---|---|
| 165 | 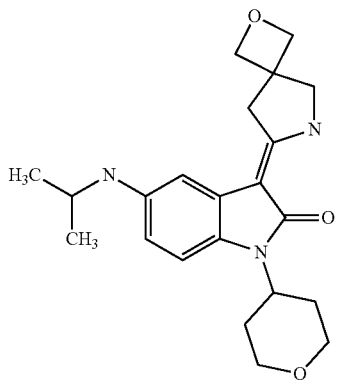 |
| 166 | 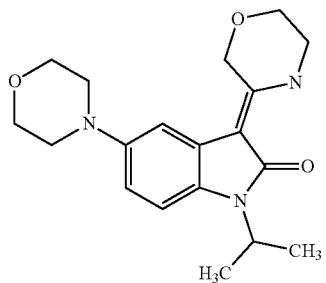 |
| 167 | 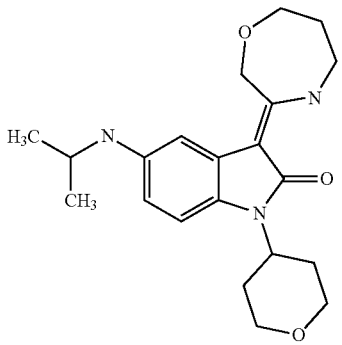 |
| 168 | 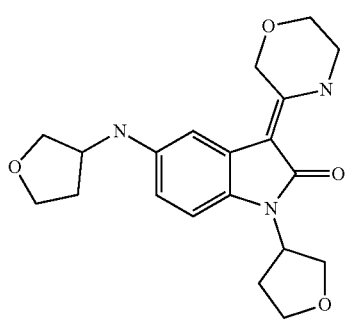 |
| # | Structure |
|---|---|
| 169 | 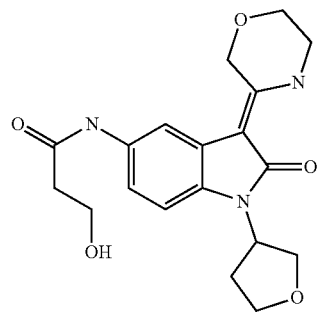 |
| 170 | 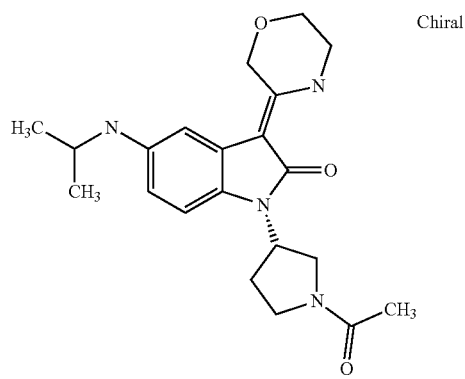 Chiral |
| 171 | |
| 172 | 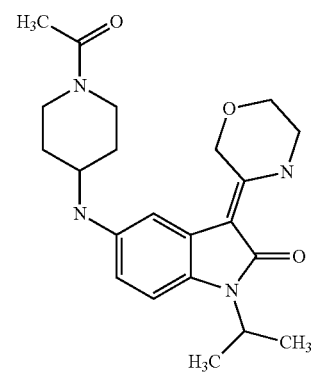 |

| # | Structure |
|---|---|
| 173 | 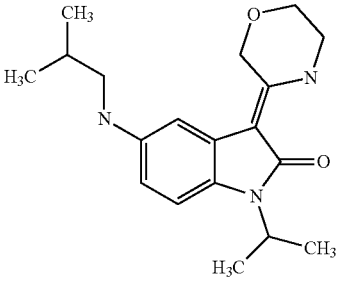 |
| 174 | 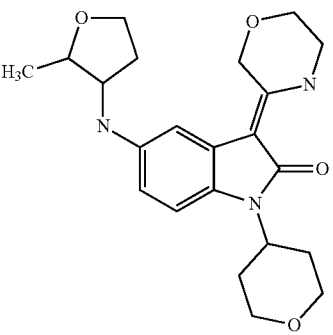 |
| 175 | 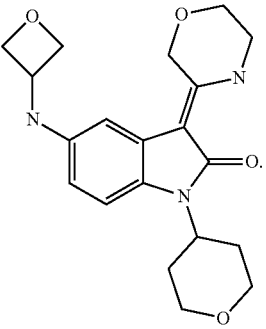 |
3. A compound selected from the group consisting of the following compounds 1001-1178, or a salt thereof:
| # | Structure |
|---|---|
| 1001 | 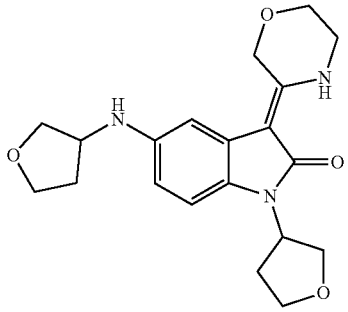 |
| 1002 | 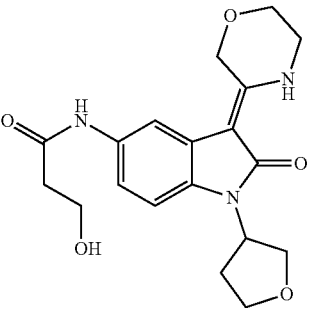 |
| 1003 | 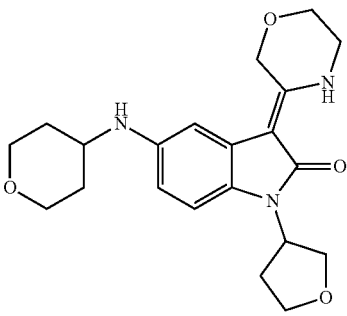 |
| 1004 | 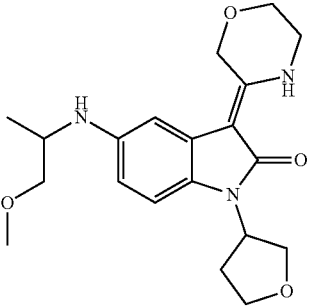 [SMILES: COCC(C)Nc1ccc2c(c1)/C(=C1\COCCN1)C(=O)N2C1CCOC1] |
| 1005 | 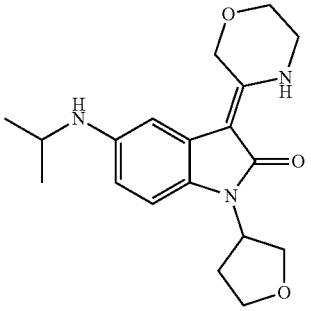 [SMILES: CC(C)Nc1ccc2c(c1)/C(=C1\COCCN1)C(=O)N2C1CCOC1] |

| # | Structure |
|---|---|
| 1006 | 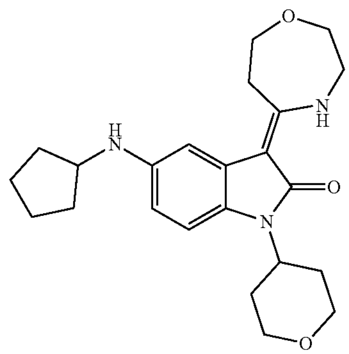 [SMILES: O=C1/C(=C2/CCOCCN2)c2cc(NC3CCCC3)ccc2N1C1CCOCC1] |
| 1007 | 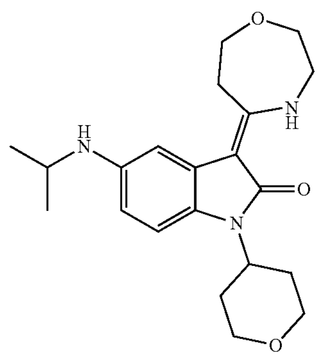 [SMILES: CC(C)Nc1ccc2c(c1)/C(=C1\CCOCCN1)C(=O)N2C1CCOCC1] |
| 1008 | 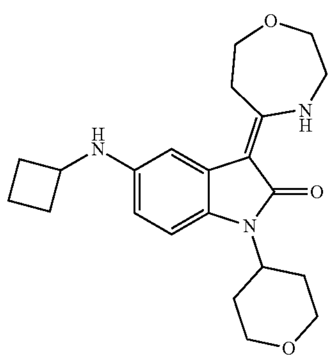 [SMILES: O=C1/C(=C2/CCOCCN2)c2cc(NC3CCC3)ccc2N1C1CCOCC1] |
| 1009 | 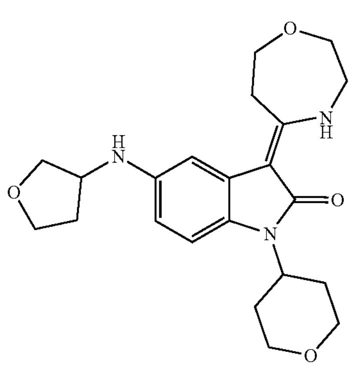 [SMILES: O=C1/C(=C2/CCOCCN2)c2cc(NC3CCOC3)ccc2N1C1CCOCC1] |

| # | Structure |
|---|---|
| 1010 | 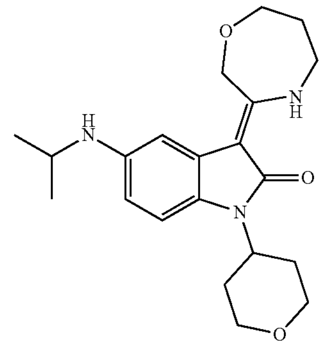 [SMILES: CC(C)Nc1ccc2c(c1)/C(=C1\COCCCN1)C(=O)N2C1CCOCC1] |
| 1011 | 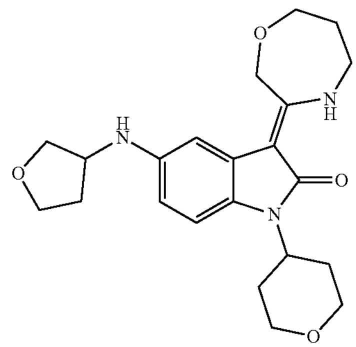 [SMILES: O=C1/C(=C2/COCCCN2)c2cc(NC3CCOC3)ccc2N1C1CCOCC1] |
| 1012 | 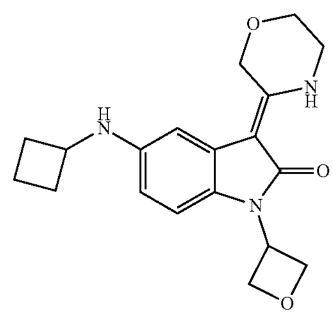 [SMILES: O=C1/C(=C2/COCCN2)c2cc(NC3CCC3)ccc2N1C1COC1] |
| 1013 | 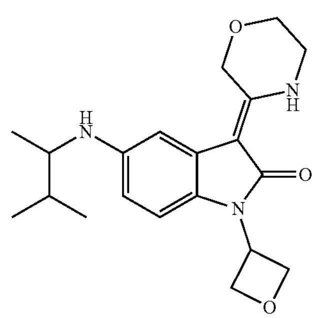 [SMILES: CC(C)C(C)Nc1ccc2c(c1)/C(=C1\COCCN1)C(=O)N2C1COC1] |

| # | Structure |
|---|---|
| 1014 | 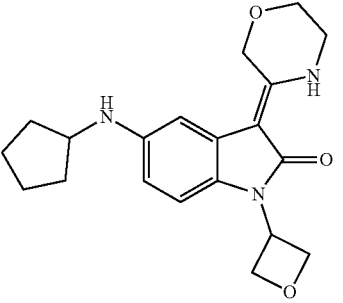 [SMILES: O=C1/C(=C2/COCCN2)c2cc(NC3CCCC3)ccc2N1C1COC1] |
| 1015 | 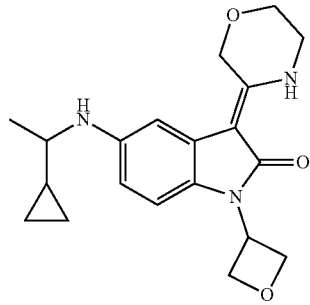 [SMILES: CC(Nc1ccc2c(c1)/C(=C1\COCCN1)C(=O)N2C1COC1)C1CC1] |
| 1016 | 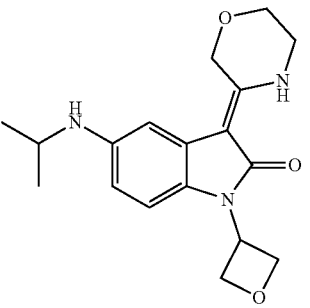 [SMILES: CC(C)Nc1ccc2c(c1)/C(=C1\COCCN1)C(=O)N2C1COC1] |
| 1017 | 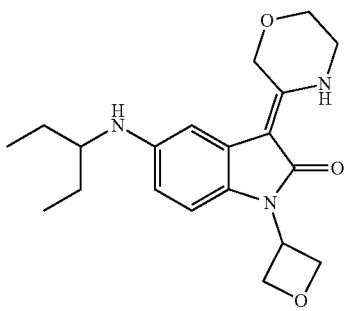 [SMILES: CCC(CC)Nc1ccc2c(c1)/C(=C1\COCCN1)C(=O)N2C1COC1] |
| 1018 | 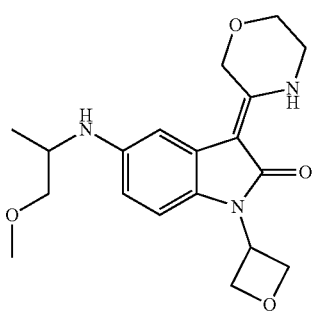 [SMILES: COCC(C)Nc1ccc2c(c1)/C(=C1\COCCN1)C(=O)N2C1COC1] |
| # | Structure |
|---|---|
| 1019 | 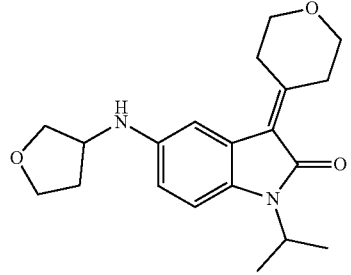 [SMILES: CC(C)N1C(=O)C(=C2CCOCC2)c2cc(NC3CCOC3)ccc21] |
| 1020 | 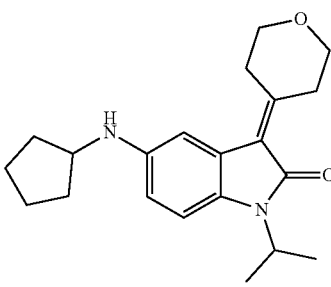 |
| 1021 | 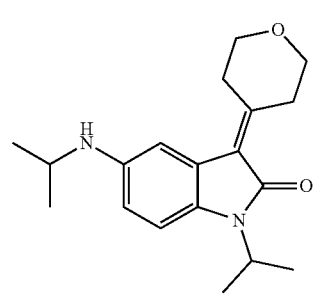 [SMILES: CC(C)Nc1ccc2c(c1)C(=C1CCOCC1)C(=O)N2C(C)C] |
| 1022 | 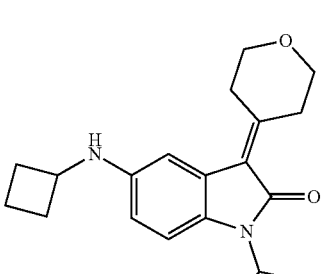 |
| 1023 | 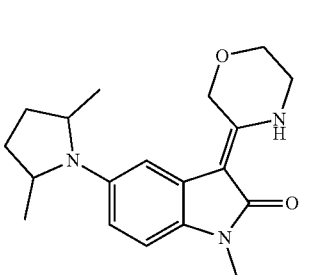 |

283
-continued

| # | Structure |
|---|---|
| 1024 | 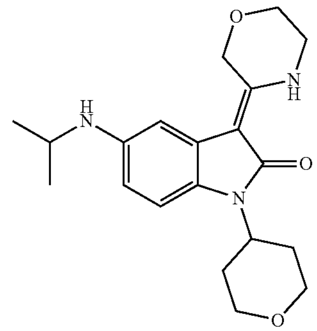 [SMILES: CC(C)Nc1ccc2c(c1)/C(=C1\COCCN1)C(=O)N2C1CCOCC1] |
| 1025 | 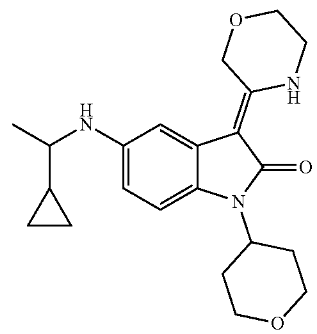 [SMILES: CC(Nc1ccc2c(c1)/C(=C1\COCCN1)C(=O)N2C1CCOCC1)C1CC1] |
| 1026 | 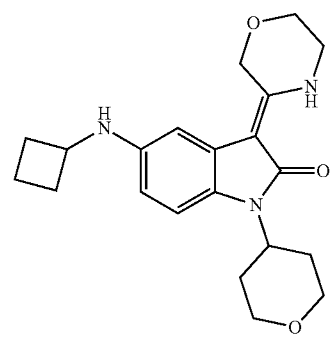 [SMILES: O=C1/C(=C2/COCCN2)c2cc(NC3CCC3)ccc2N1C1CCOCC1] |
| 1027 | 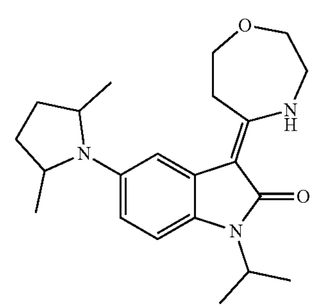 [SMILES: CC(C)N1C(=O)/C(=C2/CCOCCN2)c2cc(N3C(C)CCC3C)ccc21] |
| 1028 | 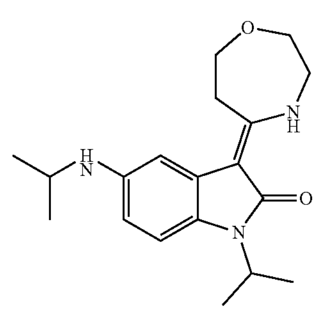 [SMILES: CC(C)Nc1ccc2c(c1)/C(=C1\CCOCCN1)C(=O)N2C(C)C] |

284
-continued

| # | Structure |
|---|---|
| 1029 | |
| 1030 | |
| 1031 | |
| 1032 | |
| 1033 | |

| # | Structure |
|---|---|
| 1034 | 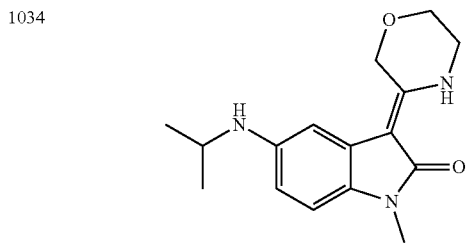 |
| 1035 | 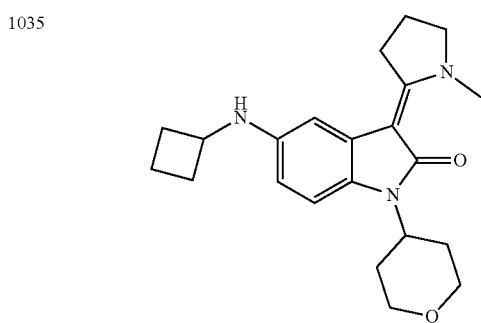 |
| 1036 | 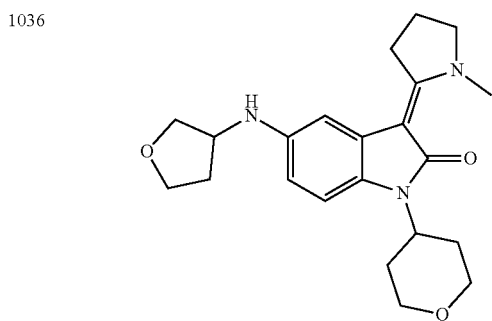 |
| 1037 | 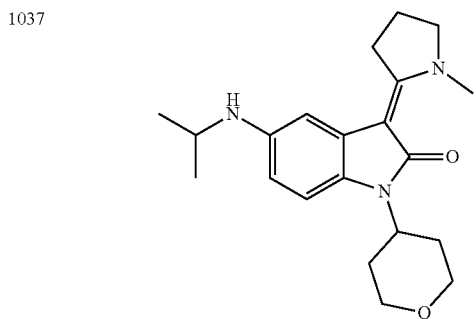 |
| 1038 | 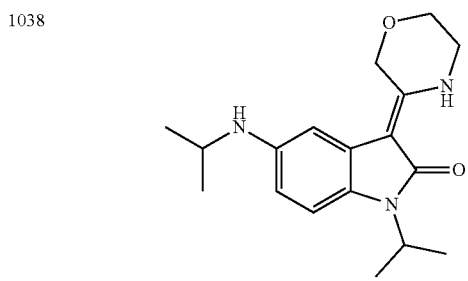 |
| # | Structure |
|---|---|
| 1039 | 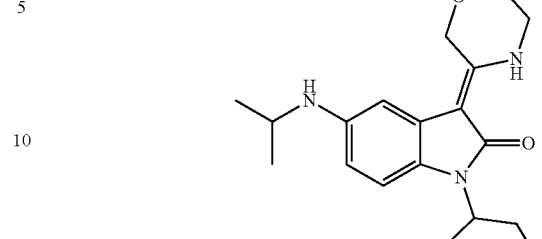 |
| 1040 | 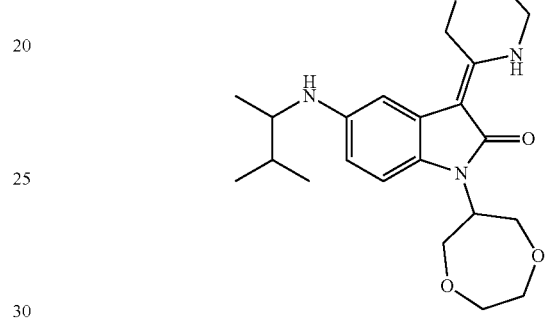 |
| 1041 | 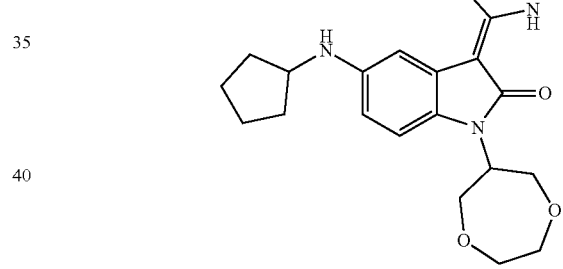 |
| 1042 | 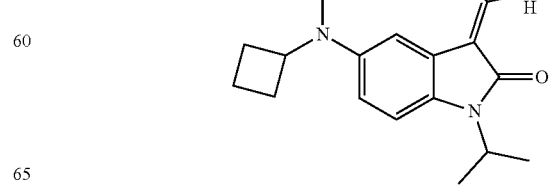 |
| 1043 |  |

| # | Structure |
|---|---|
| 1044 | 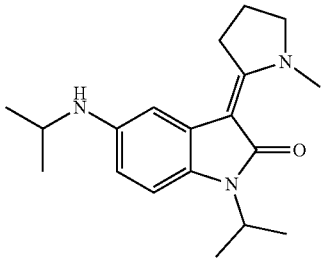 [SMILES: CC(C)Nc1ccc2c(c1)/C(=C1\CCCN1C)C(=O)N2C(C)C] |
| 1045 | 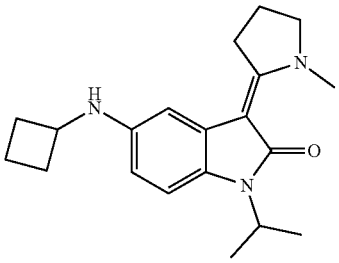 [SMILES: CC(C)N1C(=O)/C(=C2/CCCN2C)c2cc(NC3CCC3)ccc21] |
| 1046 | 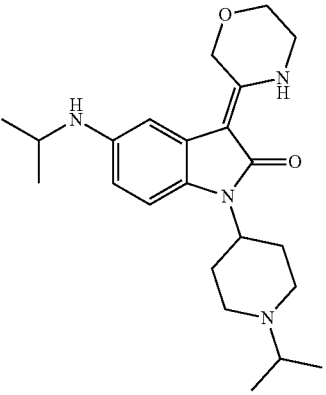 [SMILES: CC(C)Nc1ccc2c(c1)/C(=C1\COCCN1)C(=O)N2C1CCN(C(C)C)CC1] |
| 1047 | 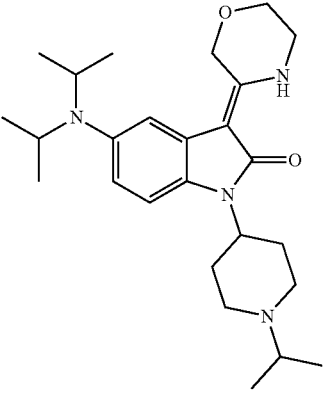 [SMILES: CC(C)N1CCC(N2C(=O)/C(=C3/COCCN3)c3cc(N(C(C)C)C(C)C)ccc32)CC1] |
| # | Structure |
|---|---|
| 1048 | 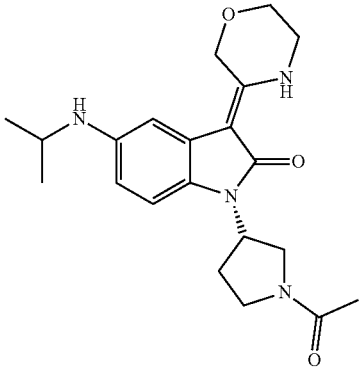 |
| 1049 | 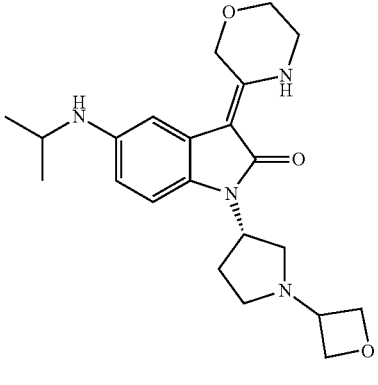 [SMILES: CC(C)Nc1ccc2c(c1)/C(=C1\COCCN1)C(=O)N2[C@H]1CCN(C2COC2)C1] |
| 1050 | 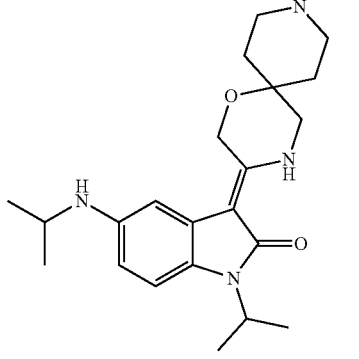 |
| 1051 | 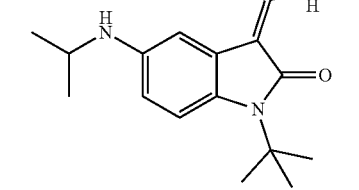 |

| # | Structure |
|---|---|
| 1052 | 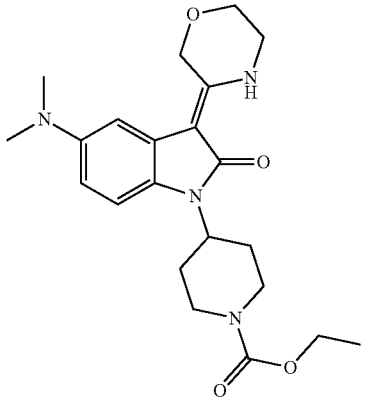 [SMILES: CCOC(=O)N1CCC(N2C(=O)/C(=C3/COCCN3)c3cc(N(C)C)ccc32)CC1] |
| 1053 | 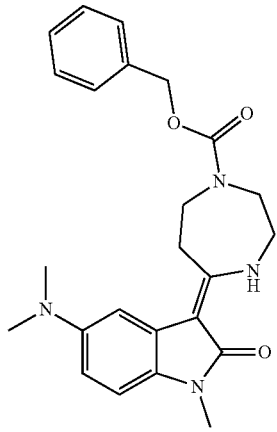 [SMILES: CN(C)c1ccc2c(c1)/C(=C1\CCN(C(=O)OCc3ccccc3)CCN1)C(=O)N2C] |
| 1054 | 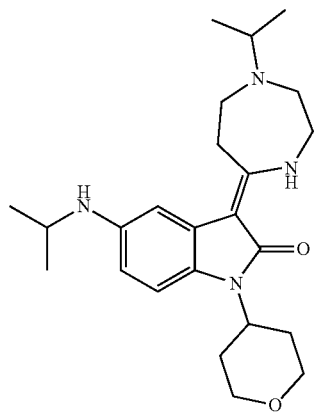 [SMILES: CC(C)Nc1ccc2c(c1)/C(=C1\CCN(C(C)C)CCN1)C(=O)N2C1CCOCC1] |
| 1055 | 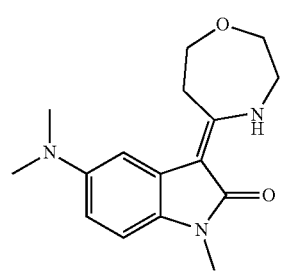 [SMILES: CN(C)c1ccc2c(c1)/C(=C1\CCOCCN1)C(=O)N2C] |
| # | Structure |
|---|---|
| 1056 | 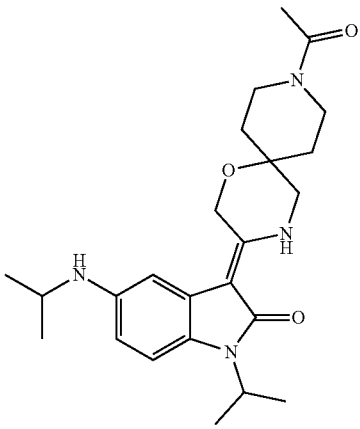 [SMILES: CC(=O)N1CCC2(CC1)CN/C(=C1\C(=O)N(C(C)C)c3ccc(NC(C)C)cc31)CO2] |
| 1057 | 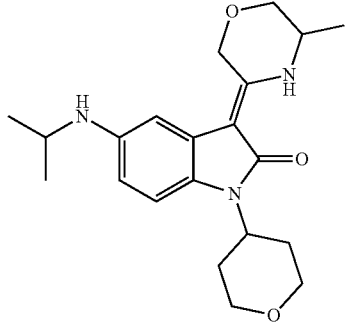 [SMILES: CC(C)Nc1ccc2c(c1)/C(=C1\COCC(C)N1)C(=O)N2C1CCOCC1] |
| 1058 | |
| 1059 | |

| # | Structure |
|---|---|
| 1060 | 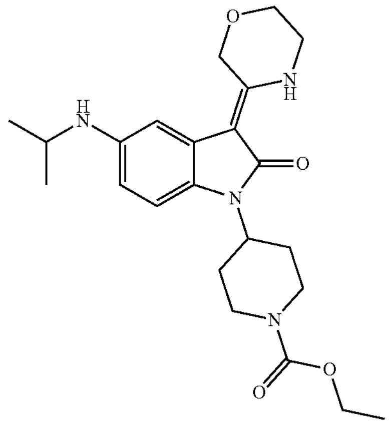 [SMILES: CCOC(=O)N1CCC(N2C(=O)/C(=C3/COCCN3)c3cc(NC(C)C)ccc32)CC1] |
| 1061 | 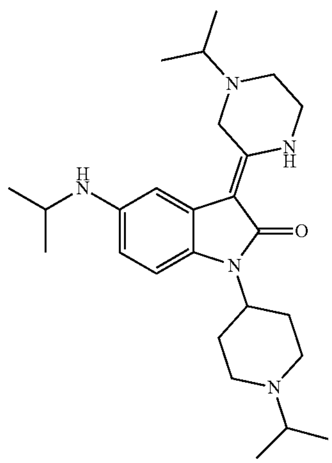 [SMILES: CC(C)Nc1ccc2c(c1)/C(=C1\CN(C(C)C)CCN1)C(=O)N2C1CCN(C(C)C)CC1] |
| 1062 | 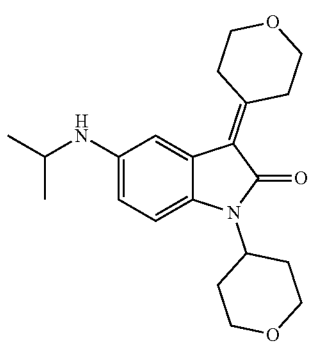 [SMILES: CC(C)Nc1ccc2c(c1)C(=C1CCOCC1)C(=O)N2C1CCOCC1] |
| 1063 | 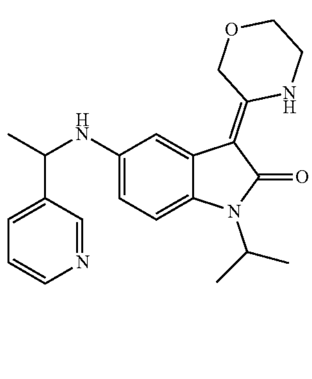 |

| # | Structure |
|---|---|
| 1064 | 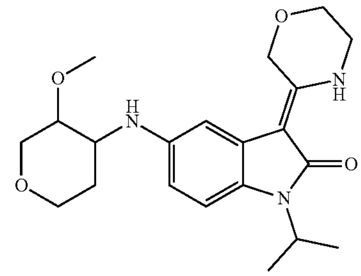 [SMILES: COC1COCCC1Nc1ccc2c(c1)/C(=C1\COCCN1)C(=O)N2C(C)C] |
| 1065 | 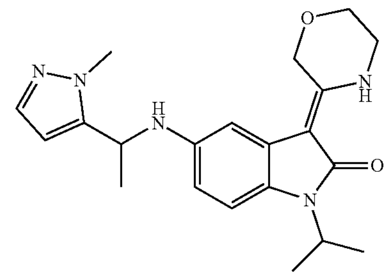 [SMILES: CC(Nc1ccc2c(c1)/C(=C1\COCCN1)C(=O)N2C(C)C)c1ccnn1C] |
| 1066 | 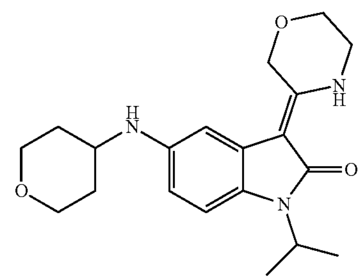 [SMILES: CC(C)N1C(=O)/C(=C2/COCCN2)c2cc(NC3CCOCC3)ccc21] |
| 1067 | 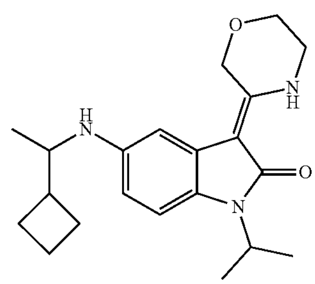 [SMILES: CC(Nc1ccc2c(c1)/C(=C1\COCCN1)C(=O)N2C(C)C)C1CCC1] |
| 1068 | 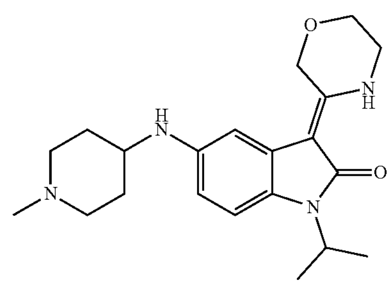 [SMILES: CC(C)N1C(=O)/C(=C2/COCCN2)c2cc(NC3CCN(C)CC3)ccc21] |

| # | Structure |
|---|---|
| 1069 | 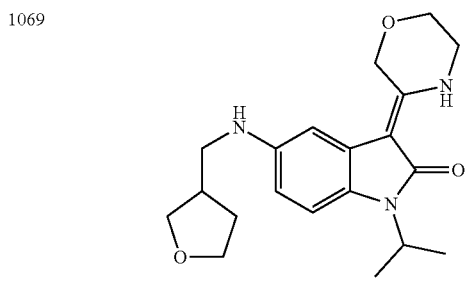 |
| 1070 | 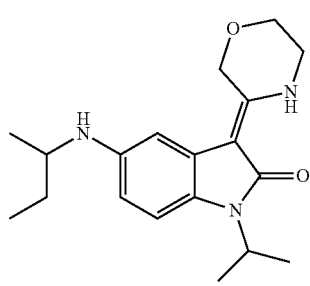 [SMILES: CCC(C)Nc1ccc2c(c1)/C(=C1\COCCN1)C(=O)N2C(C)C] |
| 1071 | 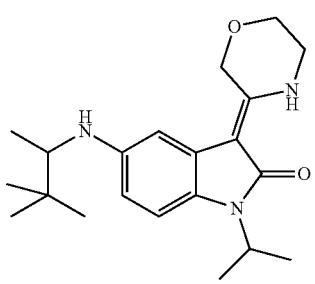 [SMILES: CC(C)N1C(=O)/C(=C2/COCCN2)c2cc(NC(C)C(C)(C)C)ccc21] |
| 1072 | 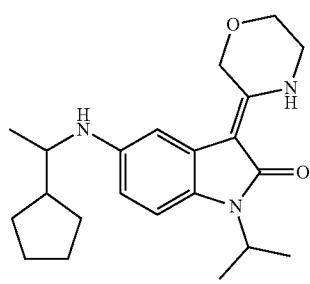 [SMILES: CC(Nc1ccc2c(c1)/C(=C1\COCCN1)C(=O)N2C(C)C)C1CCCC1] |
| 1073 | 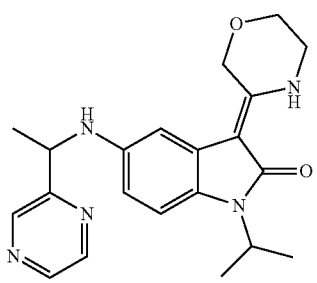 [SMILES: CC(Nc1ccc2c(c1)/C(=C1\COCCN1)C(=O)N2C(C)C)c1cnccn1] |
| # | Structure |
|---|---|
| 1074 | 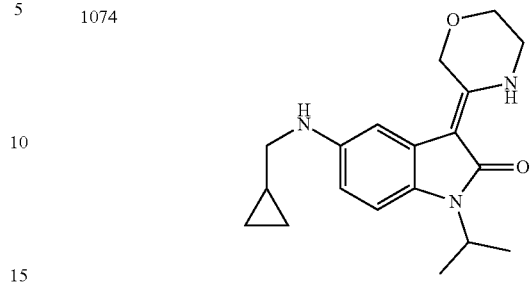 |
| 1075 | 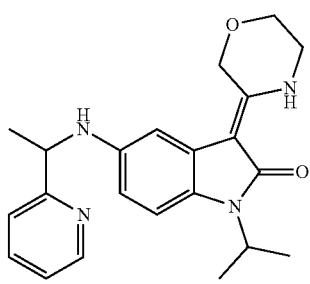 [SMILES: CC(Nc1ccc2c(c1)/C(=C1\COCCN1)C(=O)N2C(C)C)c1ccccn1] |
| 1076 | 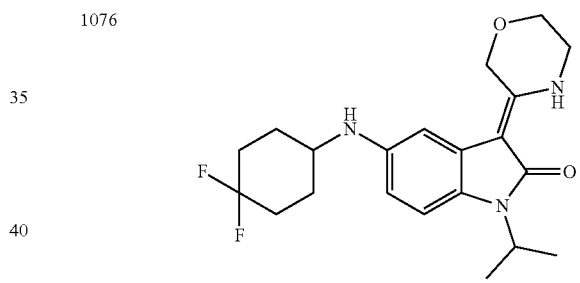 |
| 1077 | 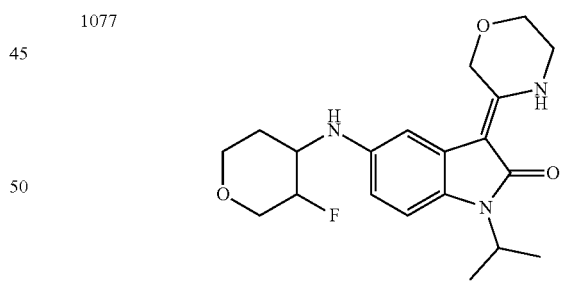 |
| 1078 | 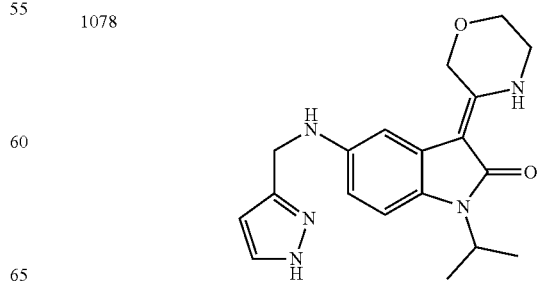 |

| # | Structure | | # | Structure |
|---|---|---|---|---|
| 1079 | 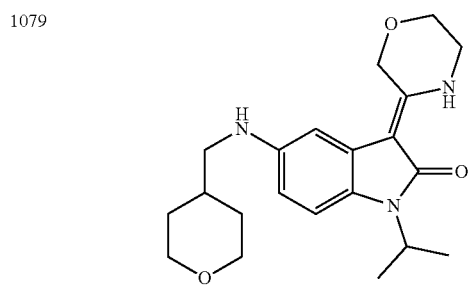 | | 1084 | 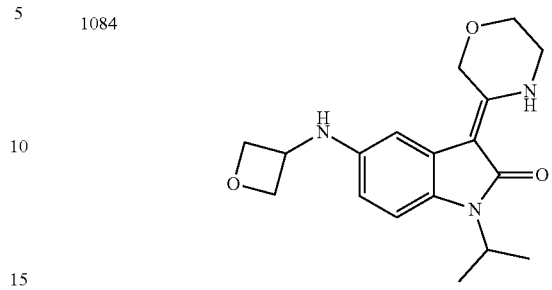 |
| 1080 | 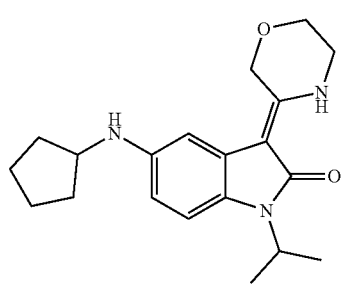 [SMILES: CC(C)N1C(=O)/C(=C2/COCCN2)c2cc(NC3CCCC3)ccc21] | | 1085 | 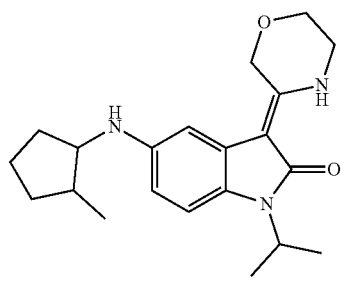 |
| 1081 | 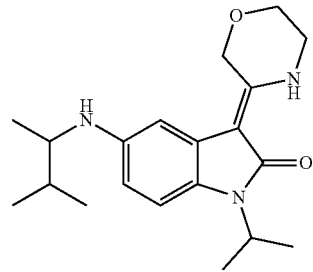 [SMILES: CC(C)C(C)Nc1ccc2c(c1)/C(=C1\COCCN1)C(=O)N2C(C)C] | | 1086 | 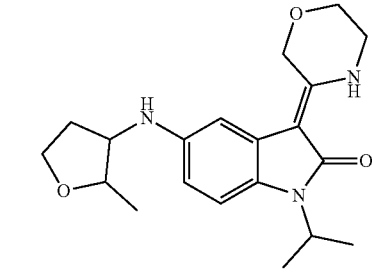 |
| 1082 | 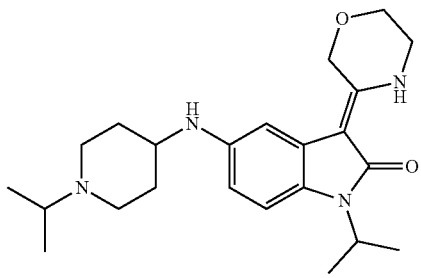 [SMILES: CC(C)N1CCC(Nc2ccc3c(c2)/C(=C2\COCCN2)C(=O)N3C(C)C)CC1] | | 1087 | 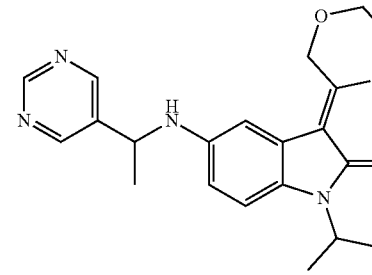 |
| 1083 | 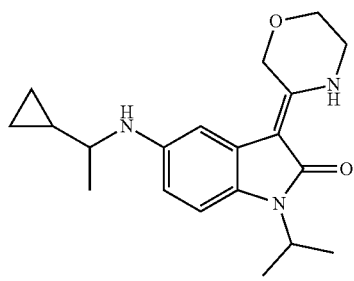 [SMILES: CC(Nc1ccc2c(c1)/C(=C1\COCCN1)C(=O)N2C(C)C)C1CC1] | | 1088 | 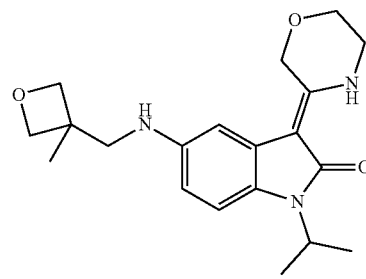 |

297
-continued

| # | Structure |
|---|---|
| 1089 | 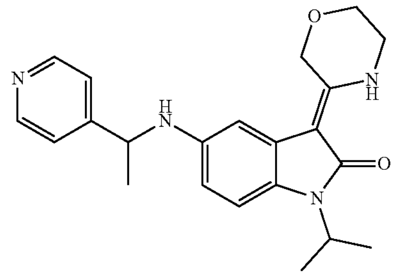 [SMILES: CC(Nc1ccc2c(c1)/C(=C1\COCCN1)C(=O)N2C(C)C)c1ccncc1] |
| 1090 | 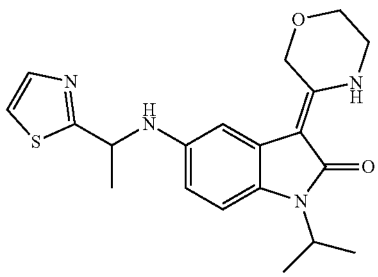 [SMILES: CC(Nc1ccc2c(c1)/C(=C1\COCCN1)C(=O)N2C(C)C)c1nccs1] |
| 1091 | 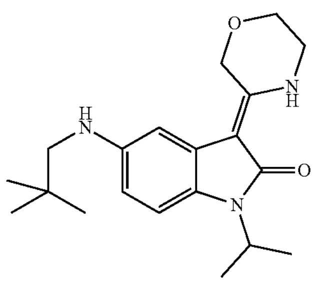 [SMILES: CC(C)N1C(=O)/C(=C2/COCCN2)c2cc(NCC(C)(C)C)ccc21] |
| 1092 | 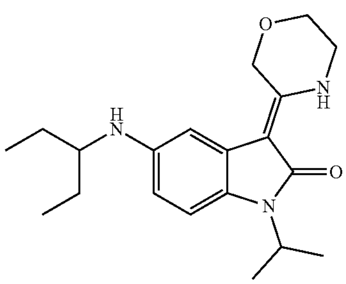 [SMILES: CCC(CC)Nc1ccc2c(c1)/C(=C1\COCCN1)C(=O)N2C(C)C] |
| 1093 | 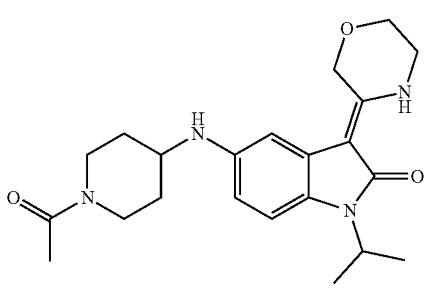 [SMILES: CC(=O)N1CCC(Nc2ccc3c(c2)/C(=C2\COCCN2)C(=O)N3C(C)C)CC1] |

298
-continued

| # | Structure |
|---|---|
| 1094 | 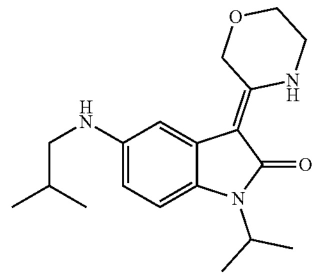 [SMILES: CC(C)CNc1ccc2c(c1)/C(=C1\COCCN1)C(=O)N2C(C)C] |
| 1095 | 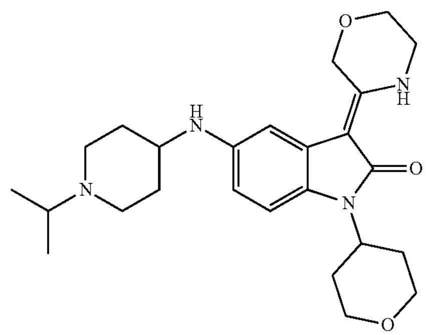 [SMILES: CC(C)N1CCC(Nc2ccc3c(c2)/C(=C2\COCCN2)C(=O)N3C2CCOCC2)CC1] |
| 1096 | 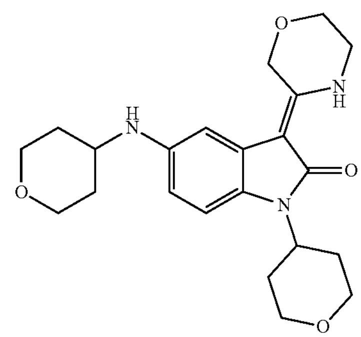 [SMILES: O=C1/C(=C2/COCCN2)c2cc(NC3CCOCC3)ccc2N1C1CCOCC1] |
| 1097 | 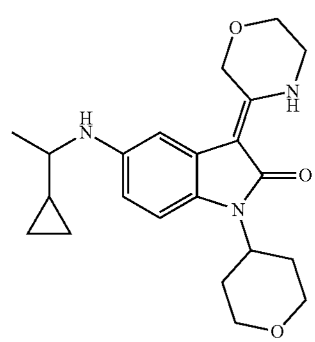 [SMILES: CC(Nc1ccc2c(c1)/C(=C1\COCCN1)C(=O)N2C1CCOCC1)C1CC1] |

| # | Structure |
|---|---|
| 1098 | 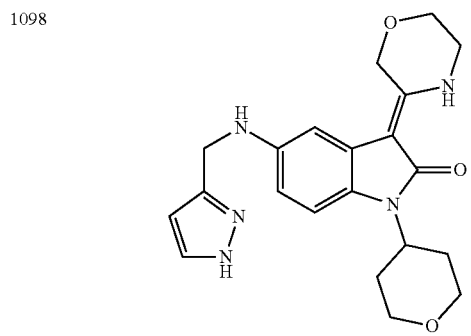 |
| 1099 | 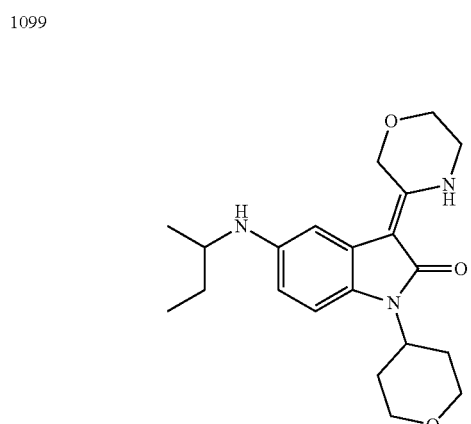 |
| 1100 | 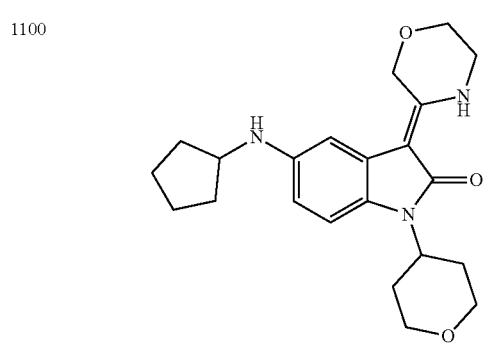 |
| 1101 | 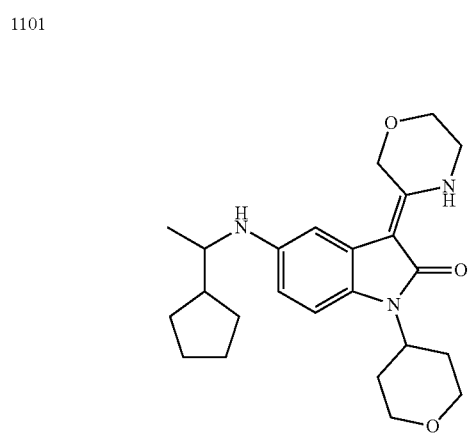 |
| # | Structure |
|---|---|
| 1102 | 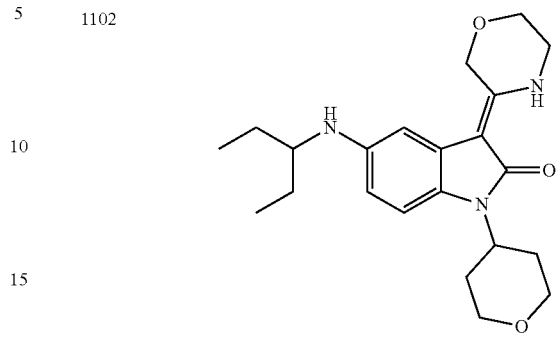 |
| 1103 | 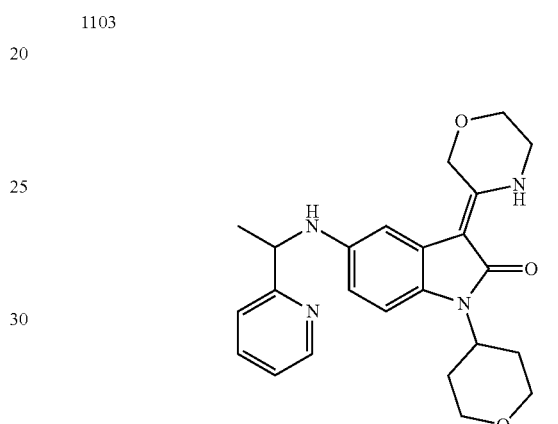 |
| 1104 | 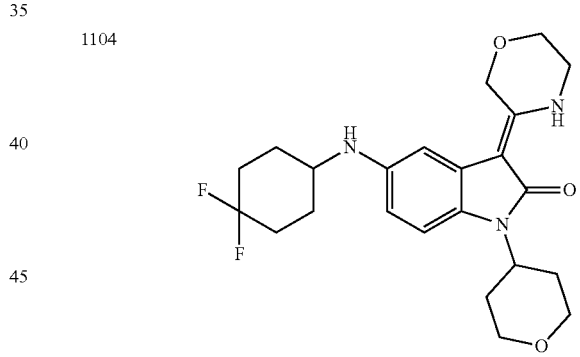 |
| 1105 | 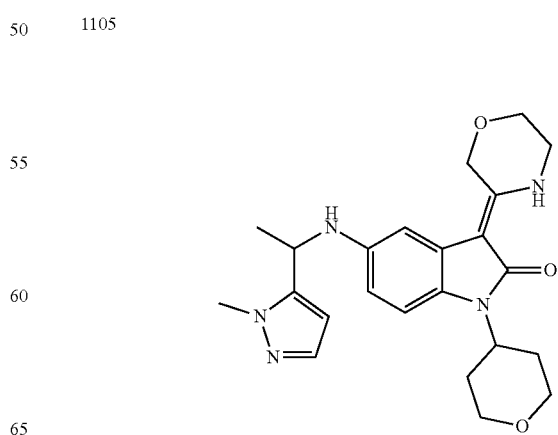 |

TABLE 301-continued
| # | Structure |
|---|---|
| 1106 | 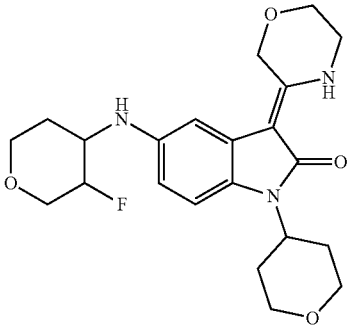 [SMILES: O=C1/C(=C2/COCCN2)c2cc(NC3CCOCC3F)ccc2N1C1CCOCC1] |
| 1107 | 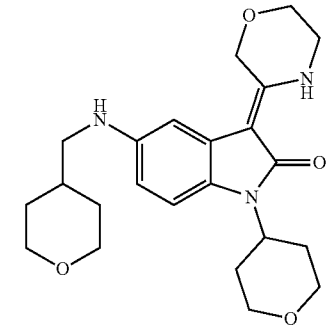 [SMILES: O=C1/C(=C2/COCCN2)c2cc(NCC3CCOCC3)ccc2N1C1CCOCC1] |
| 1108 | 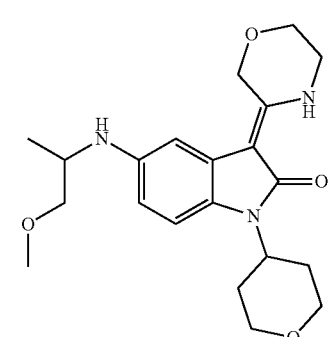 |
| 1109 | 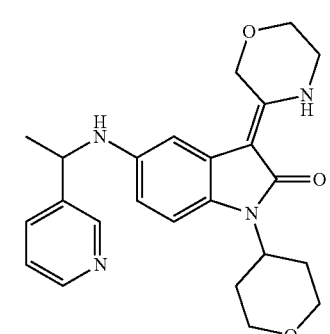 |
TABLE 302-continued
| # | Structure |
|---|---|
| 1110 | 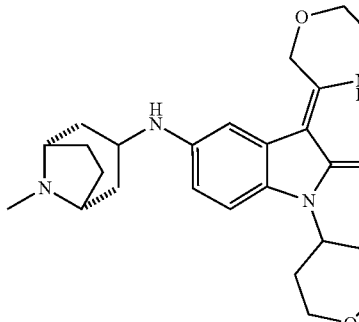 |
| 1111 | 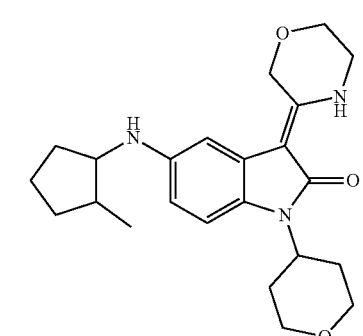 |
| 1112 | 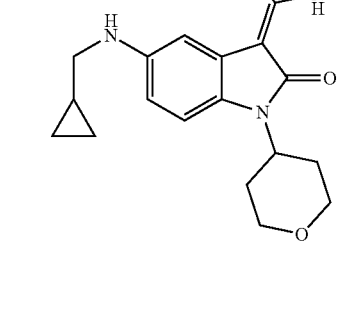 |
| 1113 | 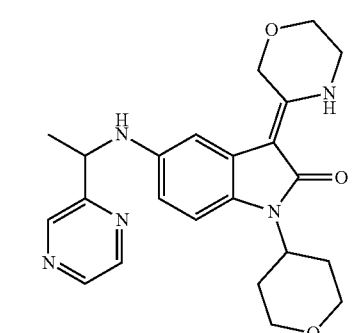 |

| # | Structure |
|---|---|
| 1114 | 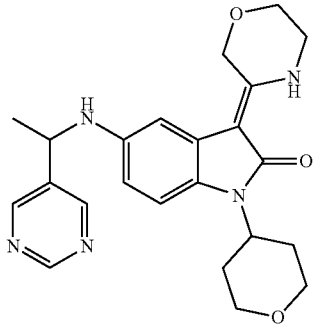 [SMILES: CC(Nc1ccc2c(c1)/C(=C1\COCCN1)C(=O)N2C1CCOCC1)c1cncnc1] |
| 1115 | 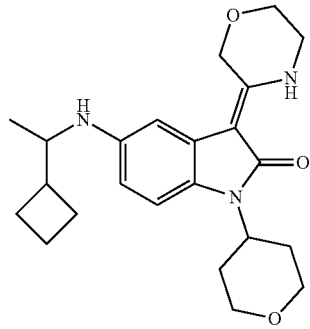 [SMILES: CC(Nc1ccc2c(c1)/C(=C1\COCCN1)C(=O)N2C1CCOCC1)C1CCC1] |
| 1116 | 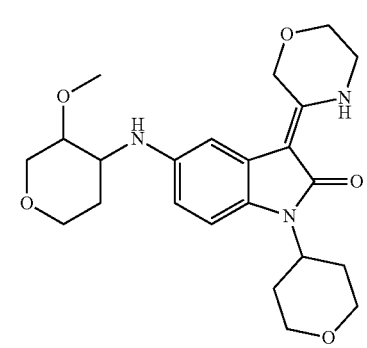 [SMILES: COC1COCCC1Nc1ccc2c(c1)/C(=C1\COCCN1)C(=O)N2C1CCOCC1] |
| 1117 | 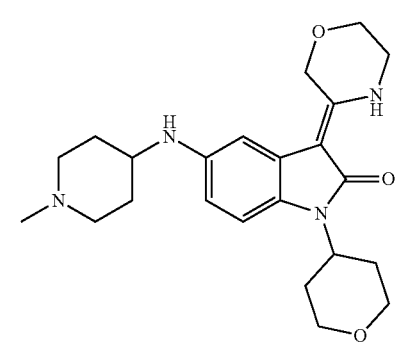 [SMILES: CN1CCC(Nc2ccc3c(c2)/C(=C2\COCCN2)C(=O)N3C2CCOCC2)CC1] |
| # | Structure |
|---|---|
| 1118 | 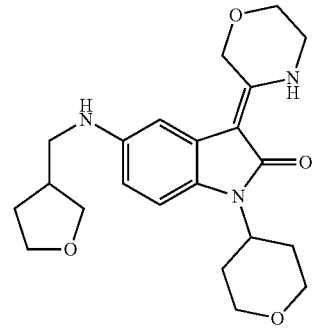 |
| 1119 | 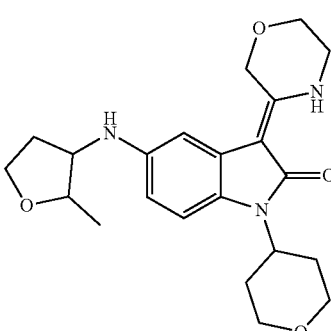 |
| 1120 | 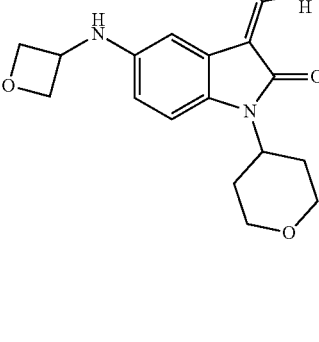 |
| 1121 | 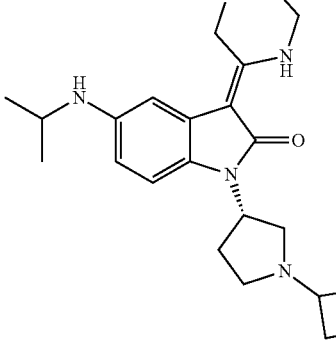 |

-continued

| # | Structure |
|---|---|
| 1122 | 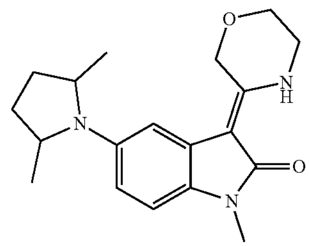 [SMILES: CC1CCC(C)N1c1ccc2c(c1)/C(=C1\COCCN1)C(=O)N2C] |
| 1123 | 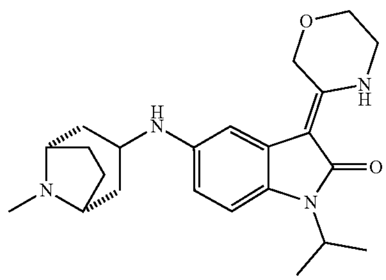 |
| 1124 | 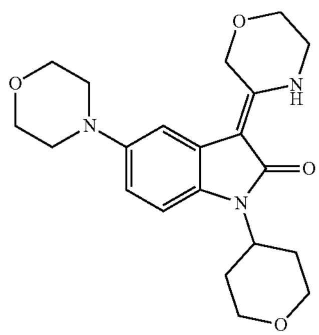 |
| 1125 | 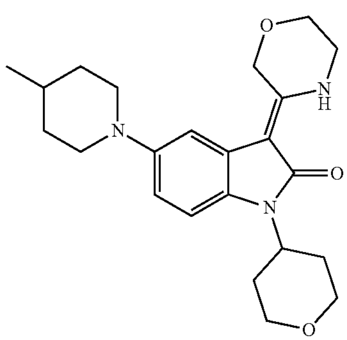 [SMILES: CC1CCN(c2ccc3c(c2)/C(=C2\COCCN2)C(=O)N3C2CCOCC2)CC1] |
| 1126 | 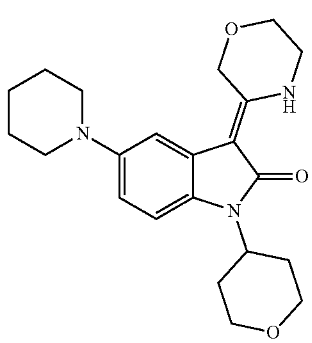 |

-continued

| # | Structure |
|---|---|
| 1127 | 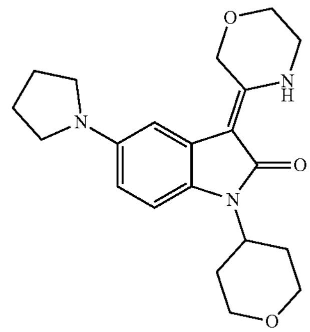 |
| 1128 | 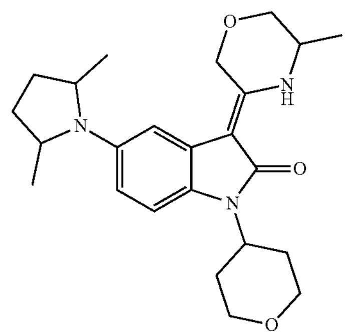 [SMILES: CC1COC/C(=C2/C(=O)N(C3CCOCC3)c3ccc(N4C(C)CCC4C)cc32)N1] |
| 1129 | 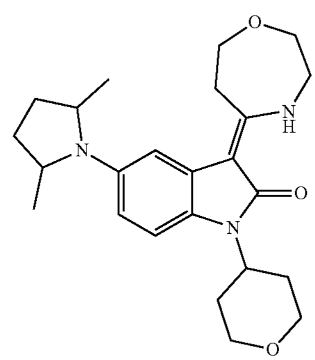 [SMILES: CC1CCC(C)N1c1ccc2c(c1)/C(=C1\CCOCCN1)C(=O)N2C1CCOCC1] |
| 1130 | 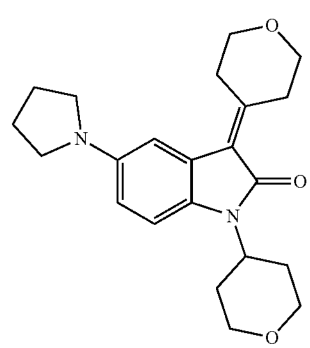 [SMILES: O=C1C(=C2CCOCC2)c2cc(N3CCCC3)ccc2N1C1CCOCC1] |

| # | Structure |
|---|---|
| 1131 | 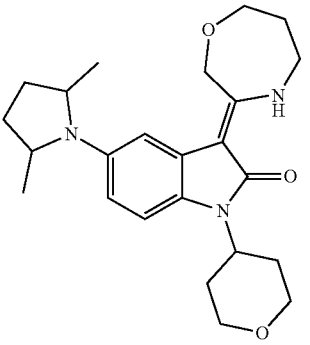 [SMILES: CC1CCC(C)N1c1ccc2c(c1)/C(=C1\COCCCN1)C(=O)N2C1CCOCC1] |
| 1132 | 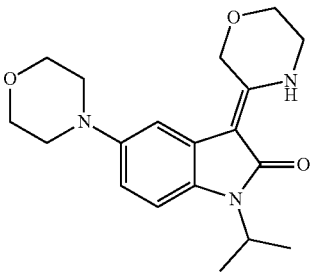 |
| 1133 | 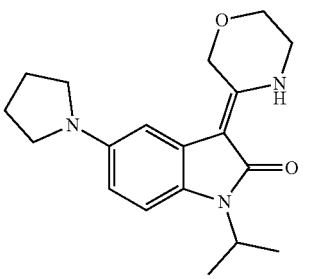 [SMILES: CC(C)N1C(=O)/C(=C2/COCCN2)c2cc(N3CCCC3)ccc21] |
| 1134 | 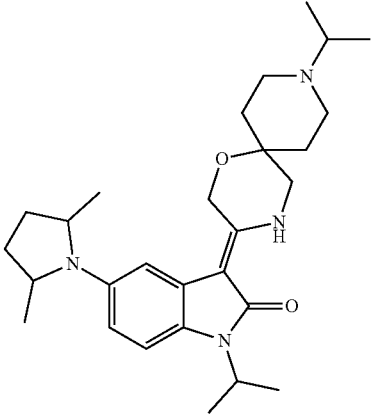 [SMILES: CC(C)N1CCC2(CC1)CN/C(=C1\C(=O)N(C(C)C)c3ccc(N4C(C)CCC4C)cc31)CO2] |
| # | Structure |
|---|---|
| 1135 | 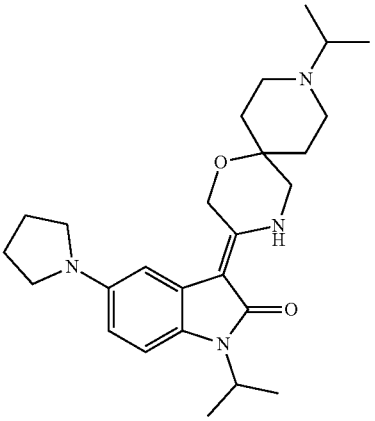 [SMILES: CC(C)N1CCC2(CC1)CN/C(=C1\C(=O)N(C(C)C)c3ccc(N4CCCC4)cc31)CO2] |
| 1136 | 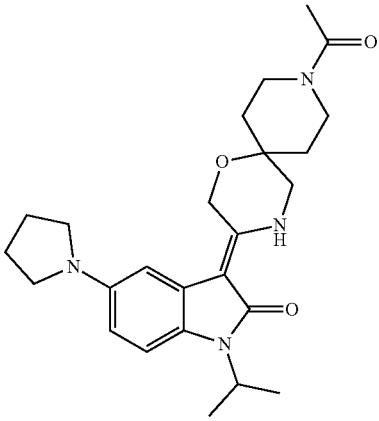 [SMILES: CC(=O)N1CCC2(CC1)CN/C(=C1\C(=O)N(C(C)C)c3ccc(N4CCCC4)cc31)CO2] |
| 1137 | 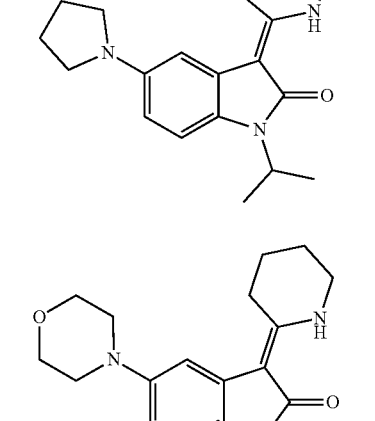 |
| 1138 |  |

309
-continued

| # | Structure |
|---|---|
| 1139 | 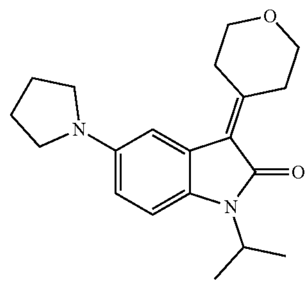 [SMILES: CC(C)N1C(=O)C(=C2CCOCC2)c2cc(N3CCCC3)ccc21] |
| 1140 | 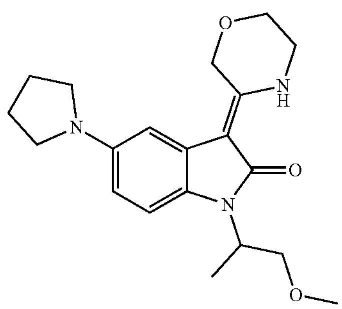 [SMILES: COCC(C)N1C(=O)/C(=C2/COCCN2)c2cc(N3CCCC3)ccc21] |
| 1141 | 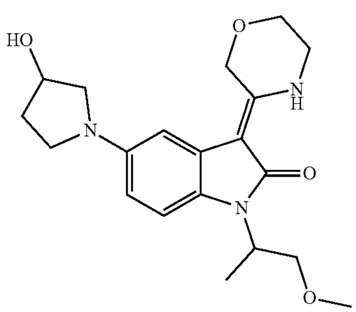 [SMILES: COCC(C)N1C(=O)/C(=C2/COCCN2)c2cc(N3CCC(O)C3)ccc21] |
| 1142 | 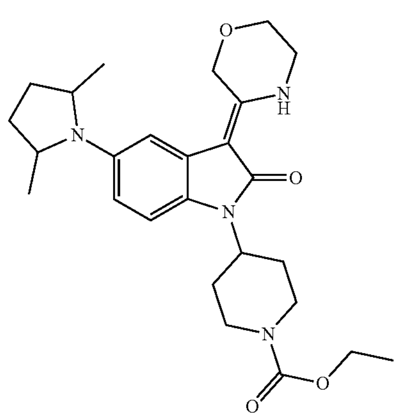 [SMILES: CCOC(=O)N1CCC(N2C(=O)/C(=C3/COCCN3)c3cc(N4C(C)CCC4C)ccc32)CC1] |

310
-continued

| # | Structure |
|---|---|
| 1143 | 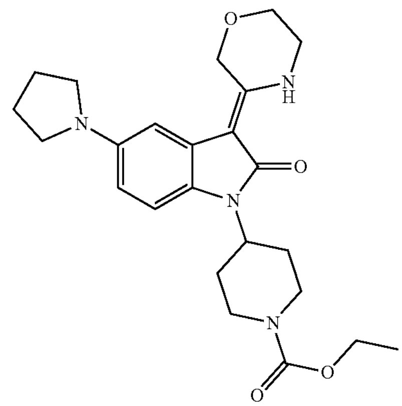 [SMILES: CCOC(=O)N1CCC(N2C(=O)/C(=C3/COCCN3)c3cc(N4CCCC4)ccc32)CC1] |
| 1144 | 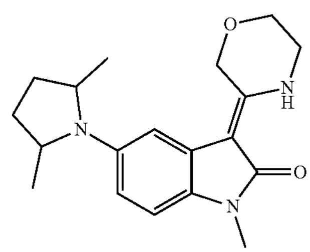 [SMILES: CC1CCC(C)N1c1ccc2c(c1)/C(=C1\COCCN1)C(=O)N2C] |
| 1145 | 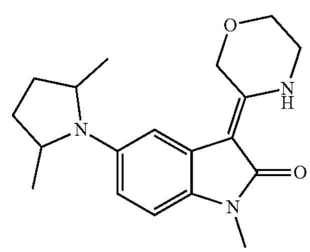 [SMILES: CC1CCC(C)N1c1ccc2c(c1)/C(=C1\COCCN1)C(=O)N2C] |
| 1146 | 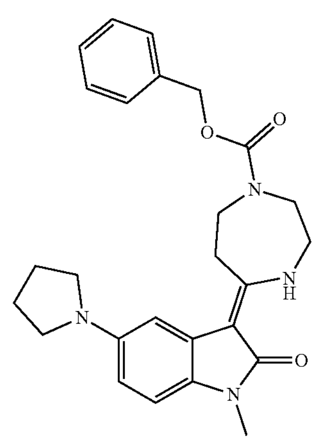 [SMILES: CN1C(=O)/C(=C2/CCN(C(=O)OCc3ccccc3)CCN2)c2cc(N3CCCC3)ccc21] |

| # | Structure |
|---|---|
| 1147 | 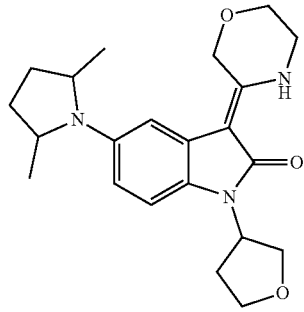 [SMILES: CC1CCC(C)N1c1ccc2c(c1)/C(=C1\COCCN1)C(=O)N2C1CCOC1] |
| 1148 | 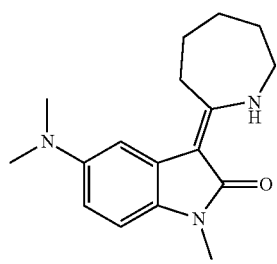 [SMILES: CN(C)c1ccc2c(c1)/C(=C1\CCCCCN1)C(=O)N2C] |
| 1149 | 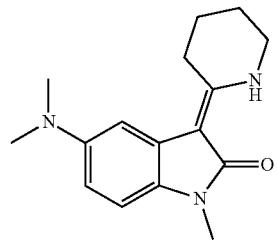 |
| 1150 | 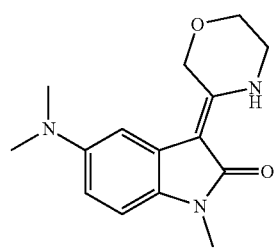 |
| 1151 | 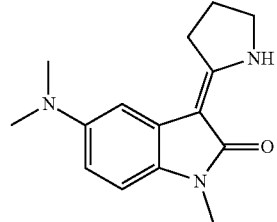 |
| # | Structure |
|---|---|
| 1152 | 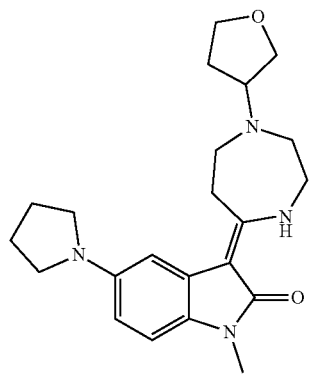 [SMILES: CN1C(=O)/C(=C2/CCN(C3CCOC3)CCN2)c2cc(N3CCCC3)ccc21] |
| 1153 | 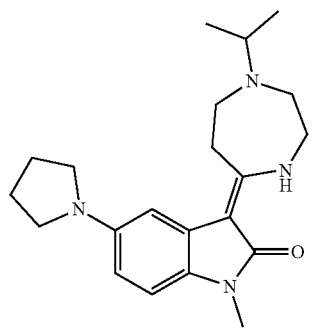 [SMILES: CC(C)N1CCN/C(=C2\C(=O)N(C)c3ccc(N4CCCC4)cc32)CC1] |
| 1154 | 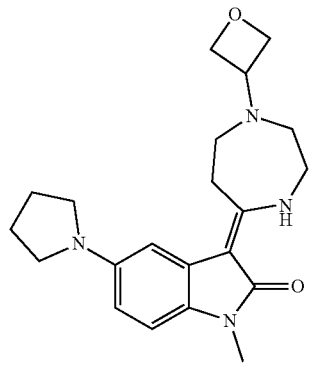 [SMILES: CN1C(=O)/C(=C2/CCN(C3COC3)CCN2)c2cc(N3CCCC3)ccc21] |
| 1155 | 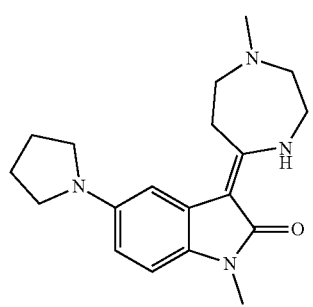 [SMILES: CN1CCN/C(=C2\C(=O)N(C)c3ccc(N4CCCC4)cc32)CC1] |

| # | Structure |
|---|---|
| 1156 | 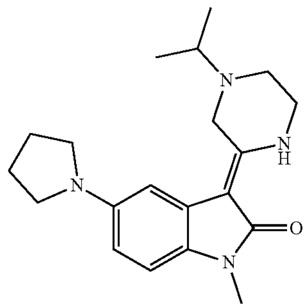 [SMILES: CC(C)N1CCN/C(=C2\C(=O)N(C)c3ccc(N4CCCC4)cc32)C1] |
| 1157 | 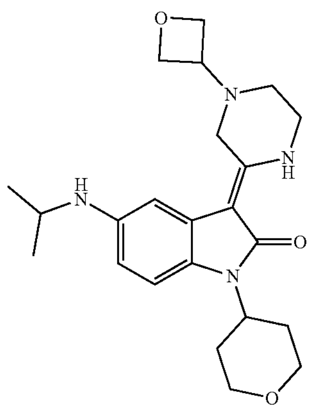 [SMILES: CC(C)Nc1ccc2c(c1)/C(=C1\CN(C3COC3)CCN1)C(=O)N2C1CCOCC1] |
| 1158 | 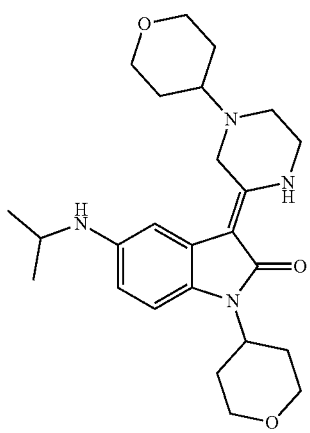 [SMILES: CC(C)Nc1ccc2c(c1)/C(=C1\CN(C3CCOCC3)CCN1)C(=O)N2C1CCOCC1] |
| 1159 | 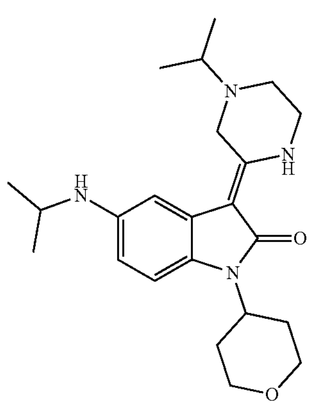 [SMILES: CC(C)Nc1ccc2c(c1)/C(=C1\CN(C(C)C)CCN1)C(=O)N2C1CCOCC1] |
| 1160 | |
| 1161 | |
| 1162 | |
| 1163 | |

-continued

| # | Structure |
|---|---|
| 1164 | 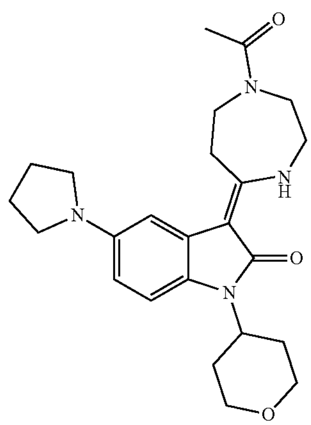 [SMILES: CC(=O)N1CCN/C(=C2\C(=O)N(C3CCOCC3)c3ccc(N4CCCC4)cc32)CC1] |
| 1165 | 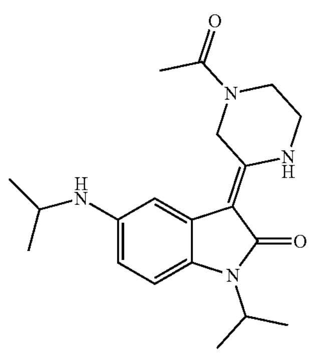 [SMILES: CC(=O)N1CCN/C(=C2\C(=O)N(C(C)C)c3ccc(NC(C)C)cc32)C1] |
| 1166 | 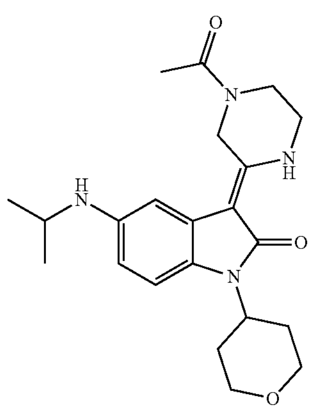 [SMILES: CC(=O)N1CCN/C(=C2\C(=O)N(C3CCOCC3)c3ccc(NC(C)C)cc32)C1] |
| 1167 | 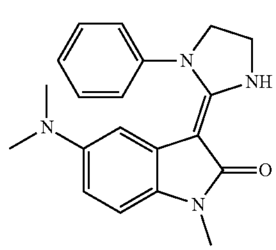 [SMILES: CN(C)c1ccc2c(c1)/C(=C1/NCCN1c1ccccc1)C(=O)N2C] |

-continued

| # | Structure |
|---|---|
| 1168 | 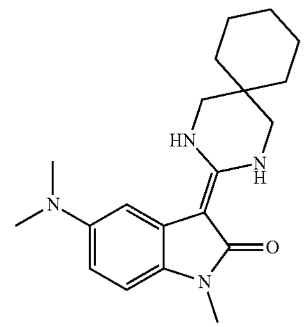 [SMILES: CN(C)c1ccc2c(c1)C(=C1NCC3(CCCCC3)CN1)C(=O)N2C] |
| 1169 | 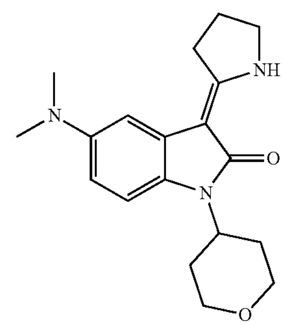 [SMILES: CN(C)c1ccc2c(c1)/C(=C1\CCCN1)C(=O)N2C1CCOCC1] |
| 1170 | 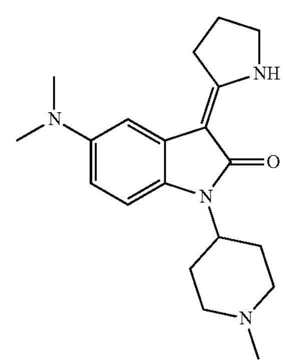 [SMILES: CN1CCC(N2C(=O)/C(=C3/CCCN3)c3cc(N(C)C)ccc32)CC1] |
| 1171 | 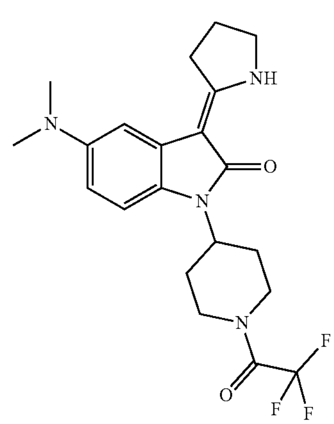 [SMILES: CN(C)c1ccc2c(c1)/C(=C1\CCCN1)C(=O)N2C1CCN(C(=O)C(F)(F)F)CC1] |

-continued

| # | Structure |
|---|---|
| 1172 | 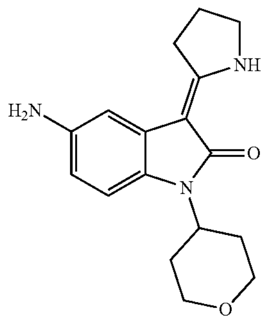 [SMILES: Nc1ccc2c(c1)/C(=C1\CCCN1)C(=O)N2C1CCOCC1] |
| 1173 | 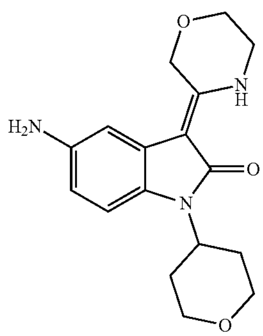 |
| 1174 | 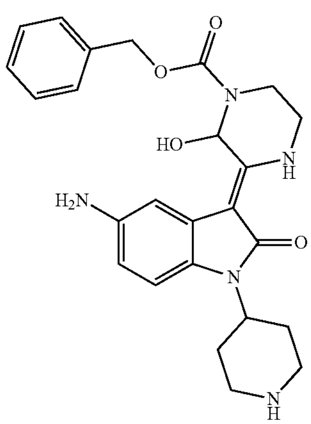 [SMILES: Nc1ccc2c(c1)/C(=C1/NCCN(C(=O)OCc3ccccc3)C1O)C(=O)N2C1CCNCC1] |

-continued

| # | Structure |
|---|---|
| 1175 | 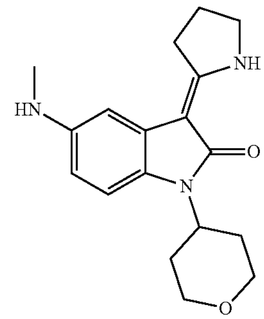 [SMILES: CNc1ccc2c(c1)/C(=C1\CCCN1)C(=O)N2C1CCOCC1] |
| 1176 | 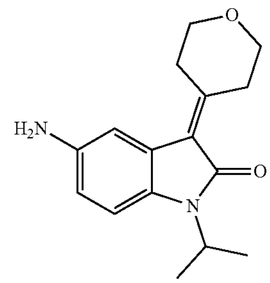 |
| 1177 | 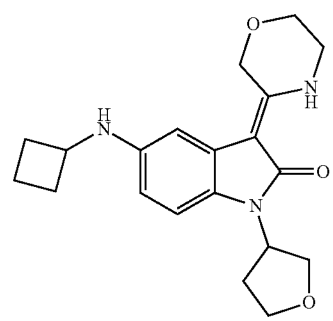 [SMILES: O=C1/C(=C2/COCCN2)c2cc(NC3CCC3)ccc2N1C1CCOC1] |
| 1178 | 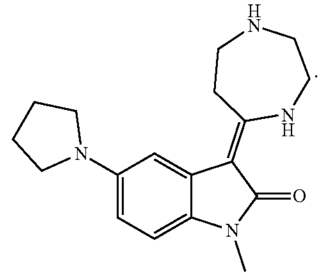 [SMILES: CN1C(=O)/C(=C2/CCNCCN2)c2cc(N3CCCC3)ccc21] |

4. The compound 26 according to claim 2 having the following formula or a salt thereof:
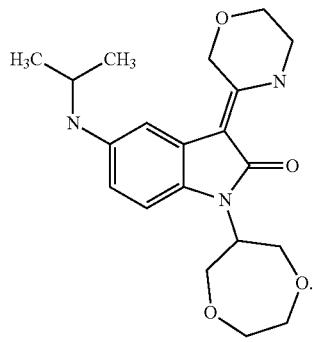
5. The compound 26 according to claim 2 having the following formula:
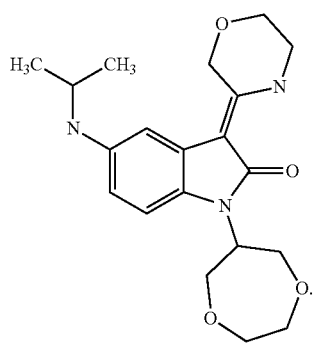
6. The compound 1024 according to claim 3 having the following formula or a salt thereof:
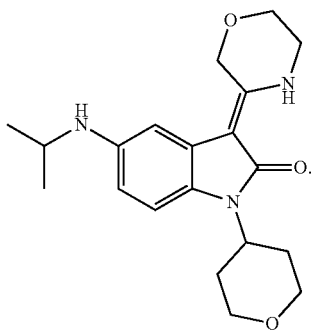 [SMILES: CC(C)Nc1ccc2c(c1)/C(=C1\COCCN1)C(=O)N2C1CCOCC1]
7. The compound 1024 according to claim 3 having the following formula:
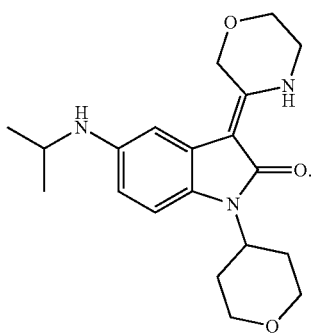 [SMILES: CC(C)Nc1ccc2c(c1)/C(=C1\COCCN1)C(=O)N2C1CCOCC1]
* * * * *